(12) United States Patent
Ingemarsson-Matzen

(10) Patent No.: US 9,687,383 B2
(45) Date of Patent: *Jun. 27, 2017

(54) INCREMENTAL AND/OR SUCCESSIVE ADJUSTABLE MANDIBULAR ADVANCEMENT DEVICE FOR PREVENTING AND TREATMENT OF SNORING AND OBSTRUCTIVE SLEEP APNEA

(71) Applicant: Petruska, LLC, Orlando, FL (US)

(72) Inventor: Natashia Ingemarsson-Matzen, Charlottenlund (DK)

(73) Assignee: Petruska, LLC, Orlando, FL (US)

( * ) Notice: Subject to any disclaimer, the term of this patent is extended or adjusted under 35 U.S.C. 154(b) by 304 days.

This patent is subject to a terminal disclaimer.

(21) Appl. No.: 14/308,636

(22) Filed: Jun. 18, 2014

(65) Prior Publication Data

US 2014/0352701 A1 Dec. 4, 2014

Related U.S. Application Data

(63) Continuation-in-part of application No. 14/011,117, filed on Aug. 27, 2013, now Pat. No. 9,545,331.

(30) Foreign Application Priority Data

Jun. 2, 2013 (DK) .................................. 2013 00338

(51) Int. Cl.
*A61F 5/56* (2006.01)

(52) U.S. Cl.
CPC ..................................... *A61F 5/566* (2013.01)

(58) Field of Classification Search
CPC ....................................................... A61F 5/566

USPC .................................................. 128/848, 846
See application file for complete search history.

(56) References Cited

U.S. PATENT DOCUMENTS

| D273,893 S | 5/1984 | Weitzman |
| D295,218 S | 4/1988 | Kwok |
| 5,313,960 A | 5/1994 | Tomasi |
| D358,889 S | 5/1995 | Wong |
| (Continued) |

FOREIGN PATENT DOCUMENTS

| AU | 1999 476 15 B2 | 1/2000 |
| CA | 223 650 3 A1 | 11/1998 |
| (Continued) |

OTHER PUBLICATIONS

Design U.S. Appl. No. 29/430,427, Applicant: Natashia Ingemarsson-Matzen.

(Continued)

*Primary Examiner* — Tarla Patel
(74) *Attorney, Agent, or Firm* — Frijouf, Rust & Pyle, P.A.

(57) ABSTRACT

The current invention relates to an adjustable mandibular advancement device with a unique combination of resilient hinging and adjustability to prevent or reduce snoring and/or obstructive sleep apnea syndrome. The adjustability is described by means of two concepts of adjustability for the relative enlargement or diminution of the members of the device, incremental and successive advancement mechanisms, in either combination or separately. By use of thermoplastic materials the device can be used in the outmost variability of the human dentition.

21 Claims, 78 Drawing Sheets

(56) References Cited

U.S. PATENT DOCUMENTS

| | | |
|---|---|---|
| 6,729,335 B1 | 5/2004 | Halstrom |
| D492,785 S | 7/2004 | Garabito |
| D529,615 S | 10/2006 | Atz |
| D554,260 S | 10/2007 | Diacopoulos |
| D604,854 S | 11/2009 | McDonald |
| D621,942 S | 8/2010 | Massad |
| 7,810,502 B1 | 10/2010 | Nguyen et al. |
| D632,395 S | 2/2011 | Massad |
| D642,277 S | 7/2011 | Farrell |
| D654,173 S | 2/2012 | Farrell |
| D710,506 S | 8/2014 | Tolentino |
| D717,449 S | 11/2014 | Farrell |
| D722,171 S | 2/2015 | Bergersen |
| D739,029 S | 9/2015 | Bergersen |
| 2005/0236003 A1 | 10/2005 | Meader |
| 2008/0099029 A1 | 5/2008 | Lamberg |
| 2008/0115791 A1 | 5/2008 | Heine |
| 2009/0014013 A1 | 1/2009 | Magnin |
| 2009/0036889 A1* | 2/2009 | Callender ............. A61F 5/566 606/55 |
| 2010/0043805 A1 | 2/2010 | Kelly |
| 2010/0300458 A1 | 12/2010 | Stubbs et al. |
| 2011/0017220 A1 | 1/2011 | Lindsay et al. |
| 2011/0226261 A1 | 9/2011 | Hernandez |
| 2012/0199136 A1* | 8/2012 | Urbano ............... A61F 5/566 128/848 |
| 2013/0014765 A1 | 1/2013 | Meads |
| 2013/0098372 A1 | 4/2013 | Webster et al. |
| 2013/0263865 A1* | 10/2013 | Khast ............... A61F 5/566 128/848 |
| 2014/0352700 A1* | 12/2014 | Ingemarsson-Matzen ............. A61F 5/566 128/848 |
| 2014/0352701 A1 | 12/2014 | Ingemarsson-Matzen |

FOREIGN PATENT DOCUMENTS

| | | |
|---|---|---|
| DE | 201 02 432 U1 | 5/2001 |
| EP | 0 312 368 | 4/1989 |
| EP | 0 337 201 B1 | 8/1992 |
| EP | 0 794 749 B1 | 6/2003 |
| EP | 1 719 481 A1 | 4/2009 |
| EP | 2 529 710 A1 | 12/2012 |
| EP | 2 491 901 A1 | 7/2014 |
| GB | 2 264 868 | 9/1993 |
| WO | WO 92/05752 | 4/1992 |
| WO | WO 92/11827 | 7/1992 |
| WO | WO 01 302 60 A1 | 5/2001 |
| WO | WO 2008 / 130 413 A1 | 10/2008 |
| WO | WO 2009 / 062 541 A1 | 5/2009 |
| WO | WO 2011 / 115 962 A1 | 9/2011 |
| WO | WO 2013 / 032 884 A1 | 3/2013 |
| WO | WO 2013 049 751 A2 | 4/2013 |
| WO | WO/2014/194910 | 12/2014 |

OTHER PUBLICATIONS

Design U.S. Appl. No. 29/536,338, Applicant: Natashia Ingemarsson-Matzen.

Industrial Design U.S. Appl. No. 35/500,086, Applicant: Natashia Ingemarsson-Matzen.

* cited by examiner

DETAIL A

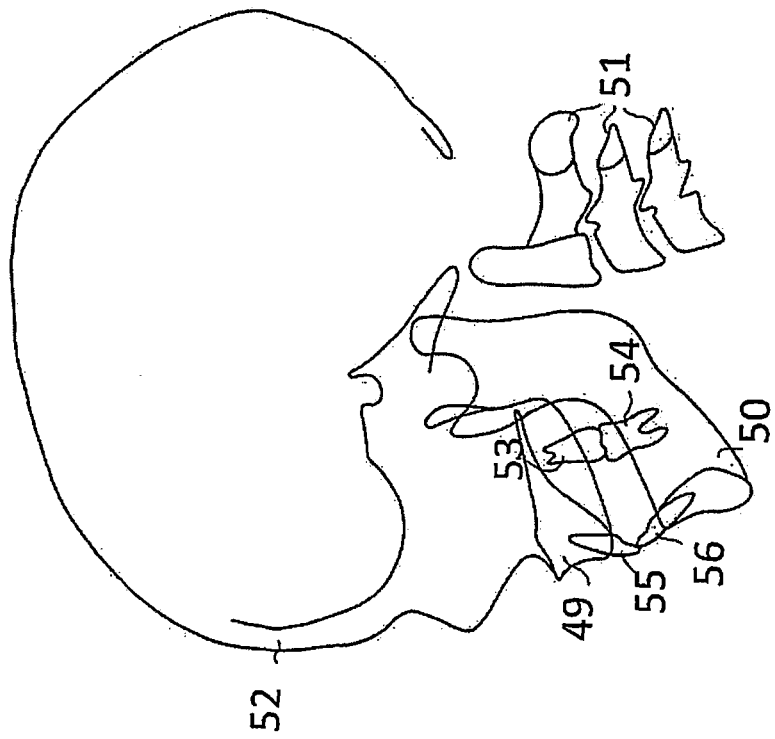

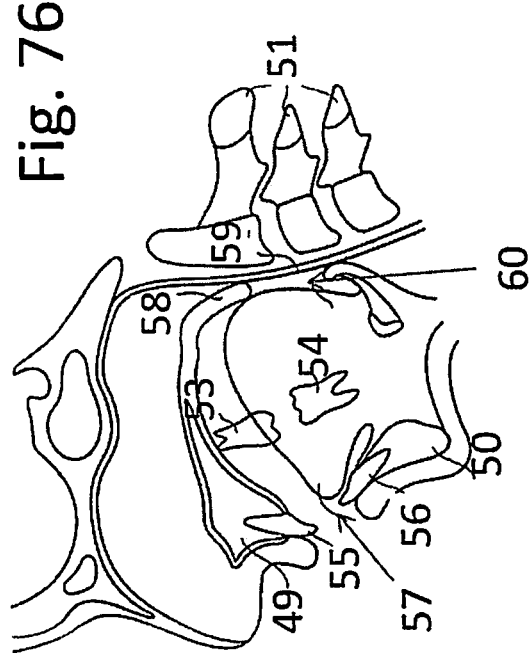

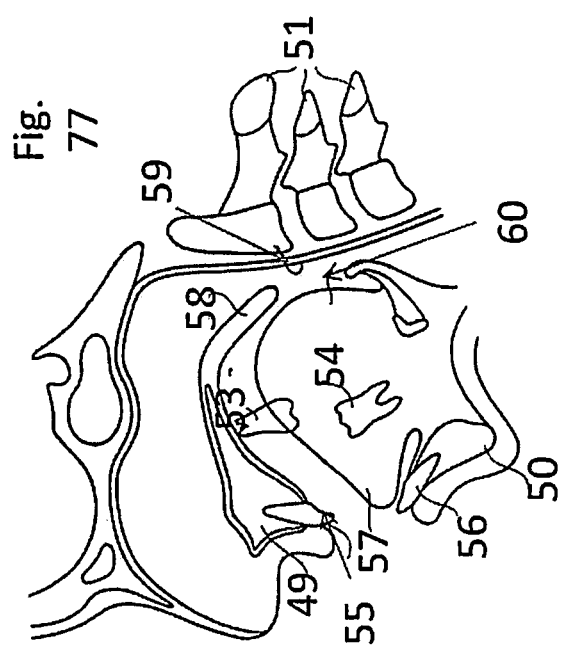

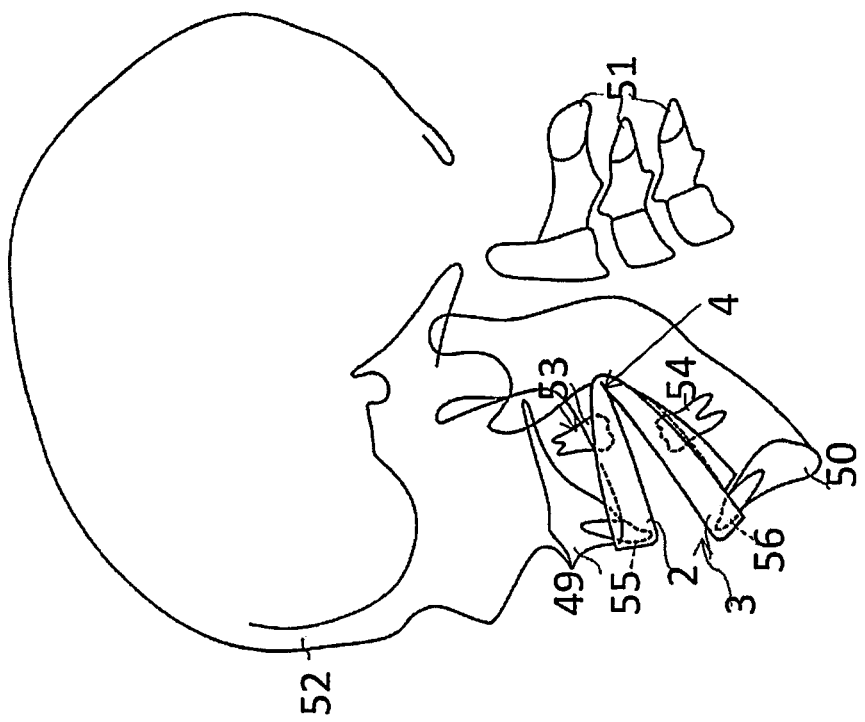

INCREMENTAL AND/OR SUCCESSIVE ADJUSTABLE MANDIBULAR ADVANCEMENT DEVICE FOR PREVENTING AND TREATMENT OF SNORING AND OBSTRUCTIVE SLEEP APNEA

CROSS-REFERENCE TO RELATED APPLICATIONS

This is a continuation-in-part of U.S. patent application Ser. No. 14/011,117 filed Aug. 27, 2013. All subject matter set forth in application Ser. No. 14/011,117 is hereby incorporated by reference into the present application as if fully set forth herein.

U.S. patent application Ser. No. 14/011,117 filed Aug. 27, 2013 claims benefit of Denmark Patent Application Number PA 2013 00338 filed Jun. 2, 2013. All subject matter set forth in Denmark Patent Application Number PA 2013 00338 is hereby incorporated by reference into the present application as if fully set forth herein.

BACKGROUND OF THE INVENTION

Field of the Invention

The current invention relates to an adjustable mandibular advancement device which by virtue of an incremental (stepwise) mechanism, advances or withdraws the mandibular relative to the maxilla in order to prevent or reduce Snoring and/or Obstructive Sleep Apnea Syndrome (OSAS) during sleep. The adjustability is accomplished by the intrinsic embedded mechanism in the two members in conjunction or separately in either of the members relative to the other.

Background of the Invention

Snoring and Obstructive Sleep Apnea are generally known today as the same disease on a continuum of the sleep disorder severity scale. Starting at the modest degree of snoring ending in the fulminate obstructive sleep apnea condition, is known as a fact.

As the disease is closely related to a large variety of physical and mental conditions, treatment is of outmost importance as soon as possible.

Whereas the snoring condition is characterized by the sounds developed by vibrating tissues in the most dorsal area of the pharynx, either the nasopharynx, or the oropharynx or the laryngopharynx, the obstructive sleep apnea is characterized by actual respiration arrest caused by occlusion of the pharyngeal airways.

Apnea appears when the upper airway passages are being sucked close to the rear part of the throat when the person is trying to breathe during sleep. The occlusion can be the result of suction or by the lapse of tonus in the oral soft tissues during the relaxed sleep condition.

When the occlusion is there, no air is passing through the pharynx and down to the lungs, and this is the situation called OSAS (Obstructive Sleep Apnea Syndrome).

The obstruction can happen as often as 1000 times during the night time sleep in which the body is depraved from oxygen uptake from the air into the blood stream, which eventually leads to the aggravated symptoms.

The severity of OSAS has been described in the medical literature numerous times giving cause to a number of symptoms and diseases:
General headache
High blood pressure
Diabetes
Hypoxic pulmonary vasoconstriction
Cardiomyopathy
Pulmonary hypertonia with cor pulmonale (increased pressure in the heart-lung circuits)
Heart failure, heart arrhythmia, heart attack
Day time melancholy or depression
Intelligence alterations
Acid Reflux (GERD—Gastro Esophageal Reflux Disease)
Potency disturbances
Worsening of ADHD (Attention deficit hyperactivity disorder), in addition to a large number of problems of a more social character, like, e.g., divorce, decreased labour activity, difficulties in keeping conversations in the track due to tiredness, etc.

Thus, compared to a normal control group without diseases, patients suffering from snoring and/or OSAS appear to have: three times as many cases of coronary heart diseases, four times as many cerebral illnesses, such as clots, twelve times as many incidents of car accidents and twice as many labour accidents due to day time sleepiness as a result of lack of sleep and/or impaired sleep quality.

Due to these conditions the life time expectancy is severely limited for these patients, and their quality of life is compromised.

The continuum of snoring diseases gives the following frequency figures:
40% of adults over 40 snore (approx. 87 million Americans)
9% of men and 4% of women suffer from some form of OSAS (approx. 30 million Americans)
Less than 10% of OSA sufferers have been diagnosed (Approx 3 million Americans)
Of those, less than 25% have been successfully treated.

For the above reasons, it is important to provide devices to eliminate and prevent apnea and the incipient stages thereof.

In the prior art, a number of surgical techniques for removal of the tissue involved in the obstruction have been developed, but all of these techniques seem to incur a certain invalidation of the patient and, at the same time, do not have a fully predictable effect.

Furthermore, a number of medical treatments have been tried out with predominantly deficient or sometimes even damaging effect.

Finally, the scientific literature and the patent literature disclose numerous devices for alarming the snoring patient during sleep; devices for tongue thrust, devices for forward movement of the soil palate; devices for obstructing the oral cavity (delimited by the lips), thereby engaging the sound from the snoring; furthermore, mandibular advancement, splints or appliances, mouth guard-like devices for provocation of either tongue, hyoid bone or jaw position changes, thereby eliminating snoring;—all of these requiring active participation from competent professionals, such as medical doctors, dentists, etc. Among such prior art devices for or attempts to inhibit snoring, the following are of particular interest in the present context:

EP 0 794 749 B1 to Ingemarsson-Matzen & Voss discloses a jaw position-regulating oral device for preventing snoring and obstructive sleep apnea during sleep. The device consist of two members, a first member to engage with the maxillary dentition and a second member to engage with the mandibular dentition, both connected by a resilient hinge. The mechanism is embedded in the mandibular advancement relative to the maxilla.

WO 2013 032 884 A1 to Fallon & Jung discloses a mandibular advancement device with an upper and lower member to engage the maxillary and mandibulary dentition respectively. The lower tray assembly is mated to and slidable adjustable by the patient relative to the upper tray assembly.

WO 2009 062 541 A1 to Magning & Magnin discloses a mandibular advancement orthosis in which the device the comprises a unitary flexible member that can be folded on itself for interaction with the teeth of the upper and lower arches, and an interchangeable flexible strip for surrounding the teeth of the upper arch, having a length that can be modified in order to obtain the desired level of mandibular advancement.

US 2009 0014 013 A1 to Magnin discloses a mandibular advancement splint made of two thermoform thermoformable trays designed to envelop the upper and lower arch. The advancement splint includes an articulated frame hazing rigid and flexible elements immersed in the thermoformable flexible material or molded around it.

EP 1 719 481 A1 to Arni discloses a mandibular advancement device with a lateral link incorporated into a mandibular protrusion device comprising an upper dental tray and a lower dental tray so as to advance or retract the lower dental arch during a vertical movement between the two. The link is adapted to be detachably accommodated in an opening of a ball pivot.

EP 2 529 710 A1 to Ash discloses a device for mandibular advancement in which an upper member and a lower member are interconnected by means of pivotal connection in which at least one is formed as a stud.

CA 223 650 3 A1 Frantz & Frantz discloses a mandibular advancement device which uses elastic bands to pull the jaw forward. The upper part having a set of retention hooks and the lower part having a set of interchangeable slide-in posterior occlusal bite planes.

WO 2008/130 413 A1 to Meade discloses a mandibular advancement device for pulling the lower jaw forward composed of an upper and a lower member to engage the dentition, where a ball type of hook support is located on both sides of the upper tray at a forward position and a ball type of hook supports are located at a rearward position of both sides of the lower jaw. A tension coil is attached to each of the upper and lower ball type of hook supports.

US 2013/001 4765 A1 to Meade discloses a mandibular advancement device for pulling the lower jaw forward composed of an upper and a lower member to engage the dentition, where a ball type of hook support is located on both sides of the upper tray at a forward position and a ball type of hook supports are located at a rearward position of both sides of the lower jaw. A tension coil is attached to each of the upper and lower ball type of hook supports.

WO 2011/115 962 A1 to Van Dyke & Tucker discloses a mandibular advancement splint made of two trays designed to envelop the upper and lower arch. The upper appliance has a pair of adjustable wings attached to the body, and the lower has a pair of fixed wings attached to the body. The upper wings are slidable adjustable.

US 2010 004 380 5 A1 to Kelly discloses a mandibular advancement device with an upper and lower member to engage with the dentition of the human. The lower dental plate having two pairs of spaced apart pillars and two removable attachable horizontal displacements inserts on the upper part.

GB 2 264 868 to Mateljan discloses an anti-snoring device for oral use, comprising members having upper and lower surfaces which engage the user's maxillary and mandibular dental arches respectively. The upper and lower surfaces are spaced so that the mandible is placed in a forwardly offset position relative to its normal position. The spacing also tensions the masticatory muscles to maintain the device in place.

US 2011/001 722 0 A1 to Lindsay et al. discloses a self-titratable mandibular repositioning device that allows for adjusting the maintained forward position by simply biting-down to preserve the desired degree of mandibular advancement, made of a lower and an upper member to engage the dentition.

US 2008 011 579 1 A1 to Heine discloses a mandibular advancement device with an intraocclusal removable device in the form of a "U" that is placed covering all of the upper jaw teeth, wherein two steps, one in each extreme of the lower part of the element, which impede the mandible be closed completely on its normal occlusion, forcing it to produce a forward displacement of the lower jaw.

US 2005 023 600 3 A1 to Meader discloses a mandibular advancement device as a single piece of molded plastic with said unit modeled from four theoretical positions including a shield like anterior portion fitted and anchored between anterior teeth-gums and behind the lips.

US 2010/030 045 8 A1 to Stubbs et al. discloses a mandibular advancement device with an upper and lower member to engage with the dentition of the human. The members are including a cam associated with one of the jaws and a follower associated with the other jaw.

US 2008/009 902 9 A1 to Lambera discloses a mandibular advancement device composed of a maxillary main body for removable attachment to the maxillary teeth with a protrusive element extending from the central portion of the body and a mandibular removable appliance attached to the mandibular anterior teeth.

EP 2 491 901 A1 to Garcia Urbano discloses regulatable intraoral mandibular advancement device for preventing snoring and sleep apnea in which a screw system is located in the central part of the connection between the upper and lower members for the engagement of the dentition.

AU 1999 476 15 B2 to Palmisano discloses a mandibular advancement device in which the upper jaw is firmly fitted into an upper plate and the lower jaw is firmly fitted into a lower plate, these two parts are connected by means of opposing flange components located to be lying in an area and close to the posterior teeth.

US 2013/001 476 5 A1 to Meade discloses a tongue and mandibular advancement device in which an upper member has hook supports anteriorly and a lower member has a plurality of hook support at the rearward position.

EP 0 337 201 to Bergersen discloses an orthodontic appliance comprising a first member to engage with the mandibular dentition and a second member to engage with the maxillary dentition. The two members are resiliently hinged together to keep the upper and lower jaw in a normal position.

WO 92/11827 to Shapiro et al. discloses an anti-snoring device for oral use consisting of a horseshoe-like upper jaw member for engaging the maxillary dentition, with the downward extending flange intended to extend into the lingual vestibule in order to maintain a forward posture of the lower jaw.

EP O 312 368 to Hays discloses an anti-snoring device for oral use which resembles the above-mentioned device, the main difference being the design of the airway passage.

WO 92/05752 to Wu discloses an anti-snoring device for oral use consisting of a spatial member congruent with the palate and a lower member adapted to the lingual aspects of the surfaces of the dentition in the lower jaw, hooks being attached to the occlusive plane of the device for fixing the two jaws in a predetermined relation.

U.S. Pat. No. 5,313,960 to Tomasi discloses an anti-snoring device for oral use consisting of two horseshoe-like individually shaped mouthpiece portions which are connected and fixed in a predetermined position in which the lower jaw protrudes in relation to the upper jaw.

U.S. Pat. No. 7,910,502 B1 to Nguyen & Nguyen discloses an anti-snoring device for oral use consisting of two horseshoe-like individually shaped mouthpiece portions which are connected and fixed by an assembly of tubes, hooks and screws to be attached to the two separate members. The main difference from the present patent application is that the device is using detachable screws, spring coils and loops to keep the mandible in a forward position, meaning that there is no intrinsic resilient hinge. Therefore the device is much more complicated and technical demanding, with an additional disadvantage of plaque accumulation and deteriorated hygiene to follow.

DE 201 02 432 U1 Trentepohl et al. discloses an anti-snoring device for the oral use comprising an upper and lower member to engage with the maxillary and mandibulary dentition interconnected by an adjustable telescopic device which is attached at the outer surface of the members. The main difference from the present patent application is that the device is using detachable telescopic devices to keep the mandible in a forward position. Thus the device lacks the intrinsic resilient hinge. Also the device is much more complicated and technical demanding, with an additional disadvantage of plaque accumulation and deteriorated hygiene to follow.

WO 21013 049 751 A2 to Rogers discloses a method for use in connection with sleep-disordered breathing, of forming oral orthotic systems to position and or stabilize a mandible of a patient includes providing an upper dental member adapted to be placed in connection with upper dentition of the patient, providing a lower dental member adapted to be placed in connection with lower dentition of the patient providing a plurality of posterior mounting structures. Each of the posterior mounting structures is adapted to be attached to one of the upper dental member or the lower dental member at a posterior, buccal position thereon. Each of the posterior mounting structures includes a plurality of positions at which one of the pluralities of connectors is attachable to the extending member. Force may be applied to the mandible of the patient via at least one of a plurality of different mechanisms via attachment of a component of the mechanism to at least one of the posterior mounting structures. The upper dental member and the lower dental member are formed, independently, from at least one polymeric material. The main difference from the present patent application is that the device is using multiple detachable mounting structures to keep the mandible in a forward position. Thus the device lacks the intrinsic resilient hinge. The upper and lower members are constructed after direct impressions of the user's teeth, and then separately in a second laboratory procedure casts the hard polymeric (acrylic) material to form congruent trays for the upper and lower jaws. As this system is using hard acrylic material it substantially differ from the present patent application in function, durability and comfort. This gives a disadvantage in regard to monetary price for the end user. Also the device is much more complicated and technical demanding, with an additional disadvantage of plaque accumulation and deteriorated hygiene to follow.

US 2013 009 837 2A1 to Webster et al. discloses an oral appliance for prevention of sleeping problems, including snoring, sleep apnea and bruxism. Specifically the device alters the position of the mandible and is made of a one piece device molded from a flexible polymer. Both upper and lower dental trays include inner and outer walls which increase contact area with the teeth. The hinge mechanism of the device includes a positive positioning system comprised of upper and lower opposed interlocking ridges. The ridges serve to create offset between the position of the upper and lower tray relative to each other, therefore advancing the user's mandible. The main difference from the present patent application is that the device is a one-piece device folded on a fixed point in the back most posterior part of the device to keep the mandible in a forward position. The interlocking ridges keep the lower and upper trays in a fixed forwarded position, thereby merely prohibits the other vice rolling possibility of the device leading into misuse of the intention of the device. Also there is no kind of incremental adjustability. Hence there is no individualization possibility.

US 2011 022 626 1A1 to Hernandez discloses a mouthpiece for reducing snoring. The mouthpiece includes an upper guard configured to lit over the upper teeth of the user, a lower guard configured to fit over the lower teeth of a user, a spacer assembly provided between the upper guard or the lower guard to provide an air passage at the middle section of the mouthpiece, a first adjustable assembly attached to the left side of the upper guard and the left side of the lower guard, and a second adjustable assembly attached to the right side of the upper guard and the right side of the lower guard. The first adjustable assembly and the second adjustable assembly are operable to move the lower guard relative to the upper guard. The main difference from the present patent application is that the device is using detachable blocks and screws devices to keep the mandible in a forward position. Although the device depicts a kind of hinge (flexible coplanar connectors), this hinge is merely decided for avoiding sharp edges at the posterior part of the two members and for ease and economy of manufacture, and can not function as an actual durable active hinge due to the fact that the screws in the blocks are rigid. In conclusion, the device is much more complicated and technical demanding, with an additional disadvantage of plaque accumulation and deteriorated hygiene to follow.

WO 01 302 60 A1 to Bergersen discloses a patent application as an intra-oral appliance for repositioning the user's mandible anterior to the user's maxillary teeth, thus opening the user's oral, pharyngeal passageway preventing snoring and sleep apnea. The appliance is two U-shaped shaped plates joined to form a hinge. The lower plate has lingual tabs which are employed to help position the appliance. The main difference from the present patent application is that the device is completely lacking any kind of incrementally adjustability. Also the WO 01 302 60 A1 is merely a transcription of the original patent EP 0 794 749 B1 (Ingemarsson-Matzen & Voss) except the lingual tabs which in the original version is a solid moldable block.

While the above devices represent attempts to solve the snoring and apnea problems, they are all rather complicated in their design and most of these require the interaction of a professional team in their individual design. Furthermore, they are rather discomfortable for the wearer, and they do not appear convincing with respect to their capability of achieving an effective and long-lasting anti-snoring effect.

Thus, there is a demand for a relatively comfortable device which provides a high degree of inhibitory effect on snoring during even long sleeping periods, such as over-night, without adverse effects on the structures involved, and which at the same time is easy and simple to use and wear for normal non-skilled persons. The present invention provides such a device.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to an incremental mandibular advancement anti-snoring and obstructive sleep apnea preventing device for a human. The human having an upper jaw and a lower jaw. The upper jaw supporting a maxillary dentition. The lower jaw supporting a mandibulary dentition. The human having a nasopharynx, a oropharynx and a hypopharynx defining a airway passage. The device comprises an upper member adapted to engage the maxillary dentition of the human. A lower member is adapted to engage the mandibulary dentition of the human. A first resilient hinge and a second resilient hinge couple the upper member and the lower member for allowing physiological movements of the lower jaw in the sagittal plane. The first resilient hinge has a first incrementally adjustment member. The second resilient hinge has a second incrementally adjustment member. The first incrementally adjustment member and the second incrementally adjustment member allow incrementally adjustments of the upper member relative to the lower member. The incrementally adjustments define multiple retaining forward positions of the lower jaw relative to the upper jaw and thereby keeping the airway passage in the nasopharynx, the oropharynx and the hypopharynx substantially free of occlusion.

In a more specific embodiment of the invention, the first incrementally adjustment member and the second incrementally adjustment member include multiple stepwise snap-on snap off members.

In one embodiment of the invention, the first incrementally adjustment member and the second incrementally adjustment member include hook and loop members.

In another embodiment of the invention, the first incrementally adjustment member and the second incrementally adjustment member include telescopic system having a cylinder member and a rod member.

In a more specific embodiment of the invention, the upper member has an anterior wall adapted to be in contact with the facial surfaces of the incisors, canines and premolars of the upper jaw. The lower member has a posterior wall adapted to be in contact with the lingual surfaces of the incisors, canines and premolars of the lower jaw.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized b those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which:

FIG. 16A shows the mandibulary lower member to engage with the maxillary dentition of the Incremental version of the Adjustable Mandibular Advancement Device top oblique view;

FIG. 16B shows the maxillary upper member to engage with the mandibular dentition of the Incremental version of the Adjustable Mandibular Advancement Device top oblique view;

FIG. 16C shows the Hinge mechanism connecting the upper maxillary and lower mandibulary members of the incremental version of the Adjustable Mandibular Advancement Device in a top oblique view;

FIG. 17A shows the mandibular lower member to engage with the mandibular dentition of the Incremental version of the Adjustable Mandibular Advancement Device bottom view oblique perspective;

FIG. 17B shows the maxillary upper member to engage with the maxillary dentition of the Incremental version of the Adjustable Mandibular Advancement Device bottom view oblique perspective;

FIG. 17C shows the Hinge mechanism connecting the upper maxillary and lower mandibulary members of the Adjustable Mandibular Advancement Device in a bottom oblique view;

FIG. 75 shows a schematic drawing of human skull with its attached mandible and upper three vertebra of the neck in a sagittal perspective. The normal relation between the upper and lower jaws in occlusion is noticed;

FIG. 76 shows the oro-pharyngeal area of the normal human in a sagittal plane, showing the jaw relation when the lower jaw has been positioned downward and backward as in a sleeping position on the back. It is clearly noticed that the dorsal part of the tongue is in direct contact with the foremost part of the pharynx in this exaggerated modification for simplification, indicating that no air can pass during this illustrated obstructive episode of the sleep.

FIG. 77 shows the oro-pharyngeal area of the normal human in a sagittal plane, showing the schematic jaw relation when the lower jaw has been allowed to adopt a lowered and forwarded position as in a sleeping position on the back with the device of this invention in place (but not showed). It is clearly noticed that the dorsal part of the tongue is NOT in direct contact with the foremost part of the pharynx in this exaggerated modification for simplification, indicating that air CAN pass during the sleep; and FIG. 78 shows the same schematic drawing of a human skull lying on his back in a sleeping position where the inserted device according to this invention shows the changed relations between the jaws, the tongue and the pharyngeal space as from FIG. 77. It should be noted that the lower mandibular jaw is kept in a substantially forwarded position relative to the upper maxillary jaw and teeth, thereby giving the free pharyngeal airway passage as the tongue attached to the inside of the mandible, is following the mandible forward away from the pharynx.

Similar reference characters refer to similar parts throughout the several Figures of the drawings.

DETAILED DISCUSSION

Figure 1:
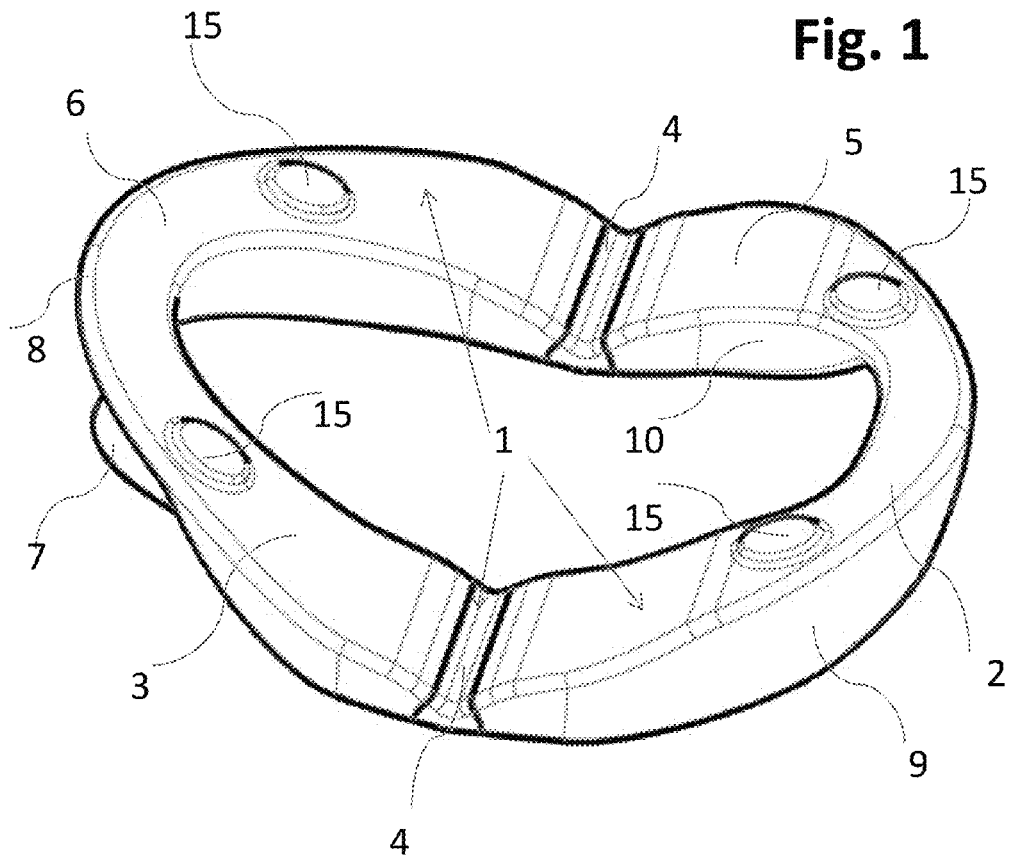
FIG. 1 shows the Incremental version of the Adjustable Mandibular Advancement Device top view in an oblique perspective in its Neutral position.
Figure 2:
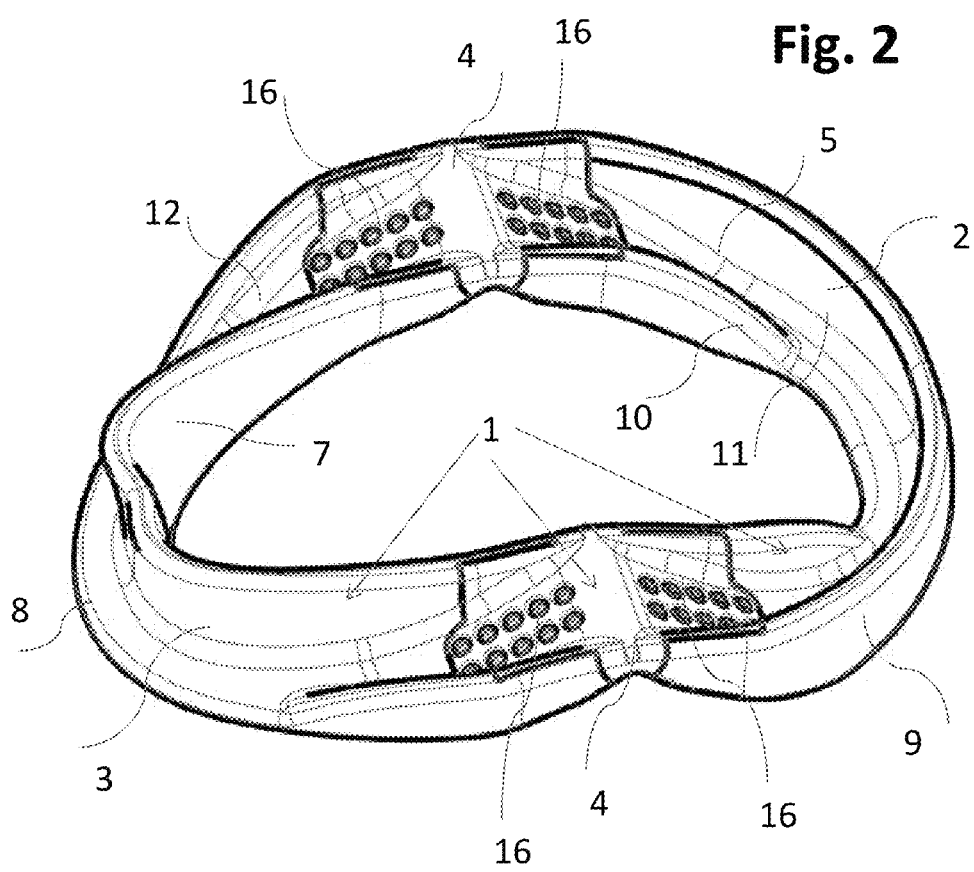
FIG. 2 shows the Incremental version of the Adjustable Mandibular Advancement Device bottom view in an oblique perspective in its Neutral position.
Figure 3:
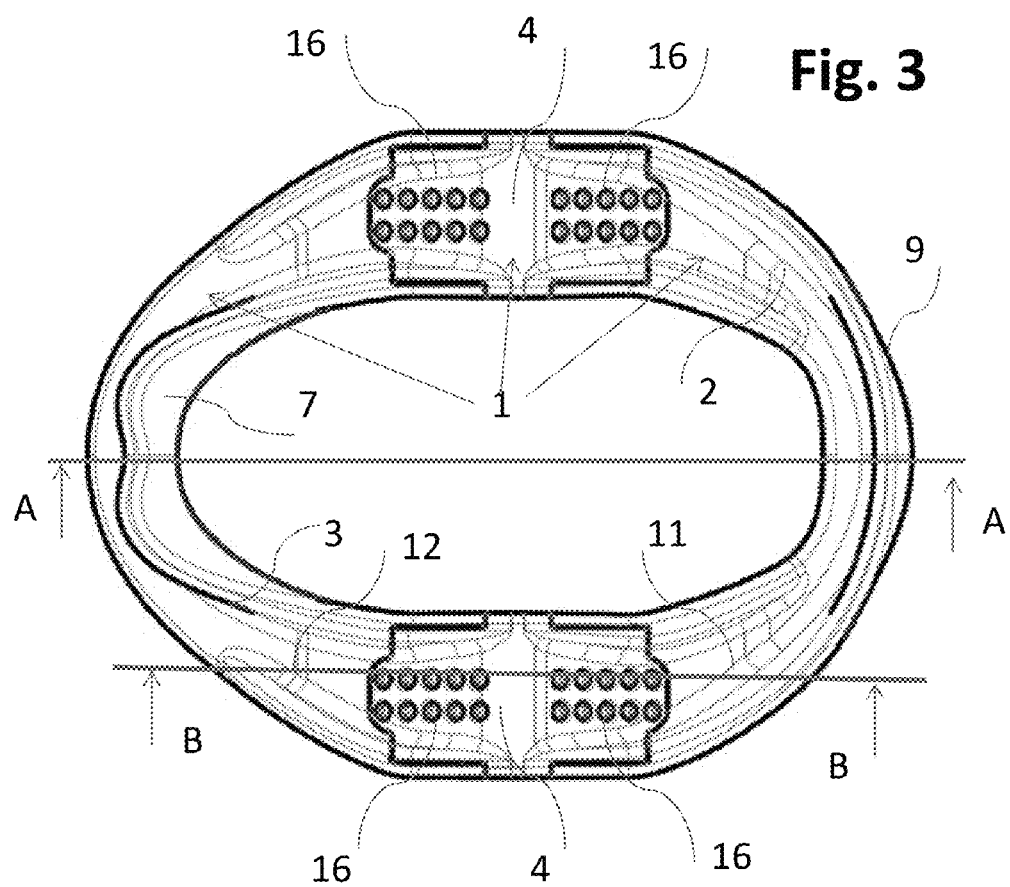
FIG. 3 shows the Incremental version of the Adjustable Mandibular Advancement Device bottom view in a perpendicular perspective in its Neutral position.
Figure 4:
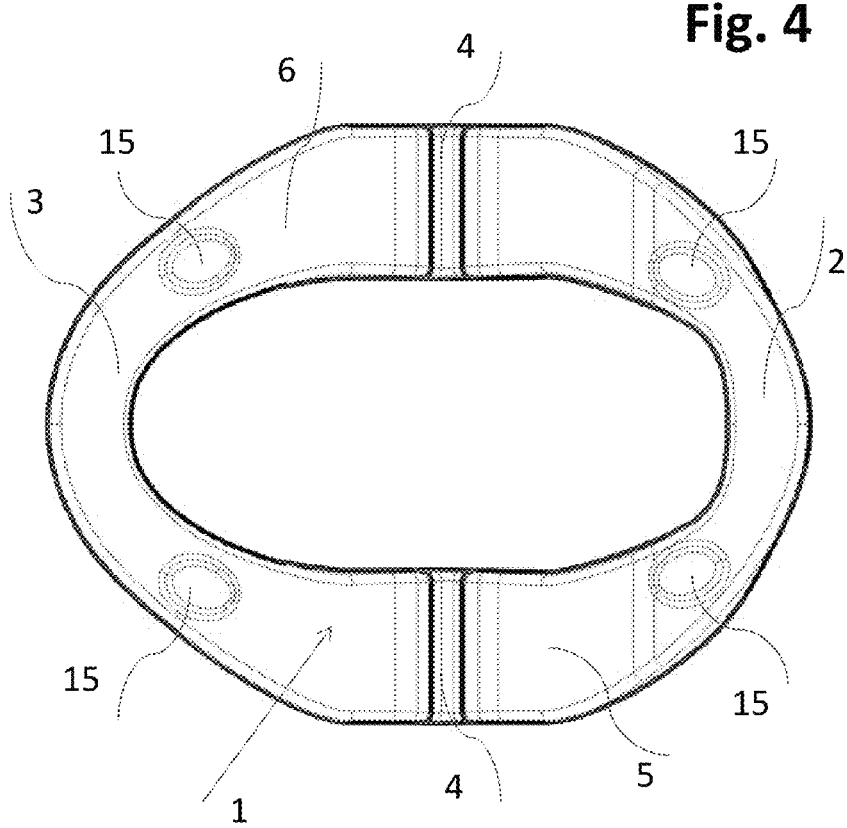
FIG. 4 shows the Incremental version of the Adjustable Mandibular Advancement Device top view in a perpendicular perspective in its Neutral position.
Figure 5:
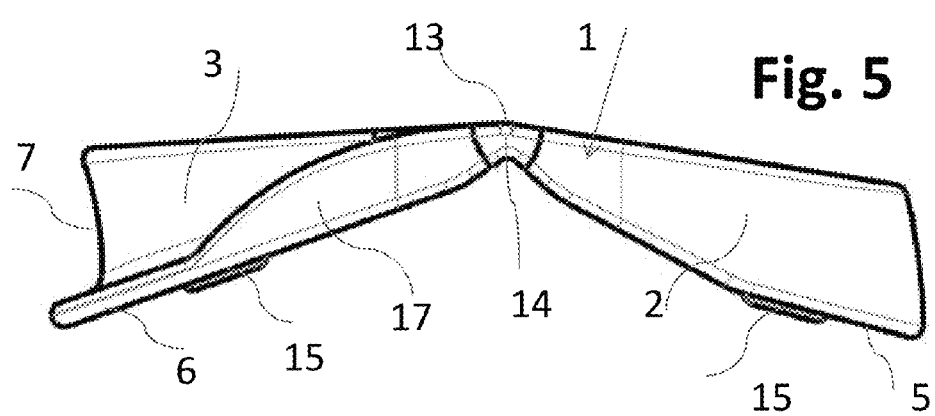
FIG. 5 shows the Incremental version of the Adjustable Mandibular Advancement Device from aside in its Neutral position.
Figure 6:
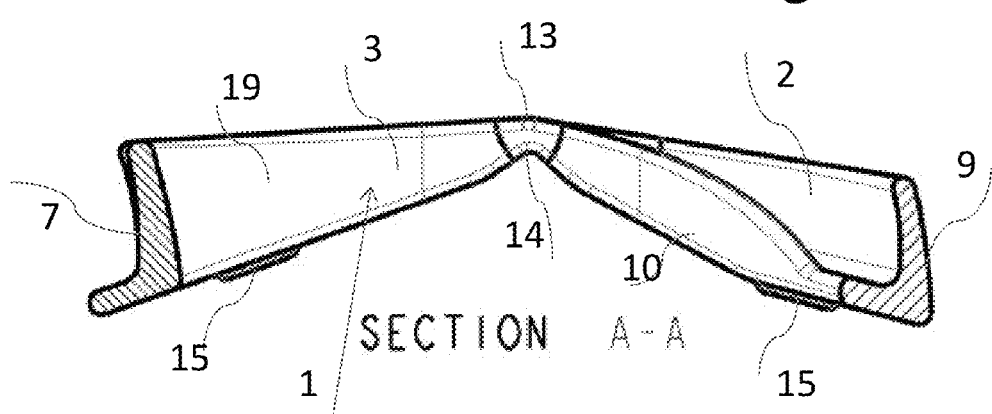
FIG. 6 shows the Incremental version of the Adjustable Mandibular Advancement Device in cross section at line A in FIG. 3 in its Neutral position.
Figure 7:
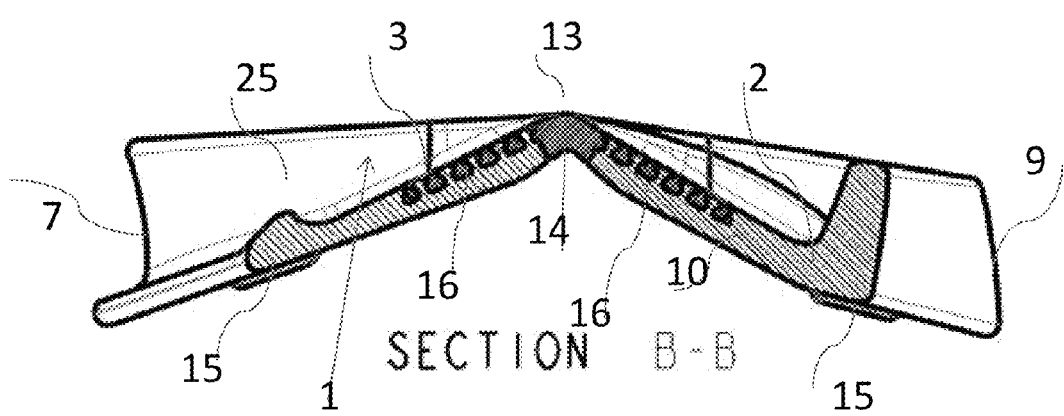
FIG. 7 shows the Incremental version of the Adjustable Mandibular Advancement Device in cross section at line B in FIG. 3 in its Neutral position.
Figure 8:
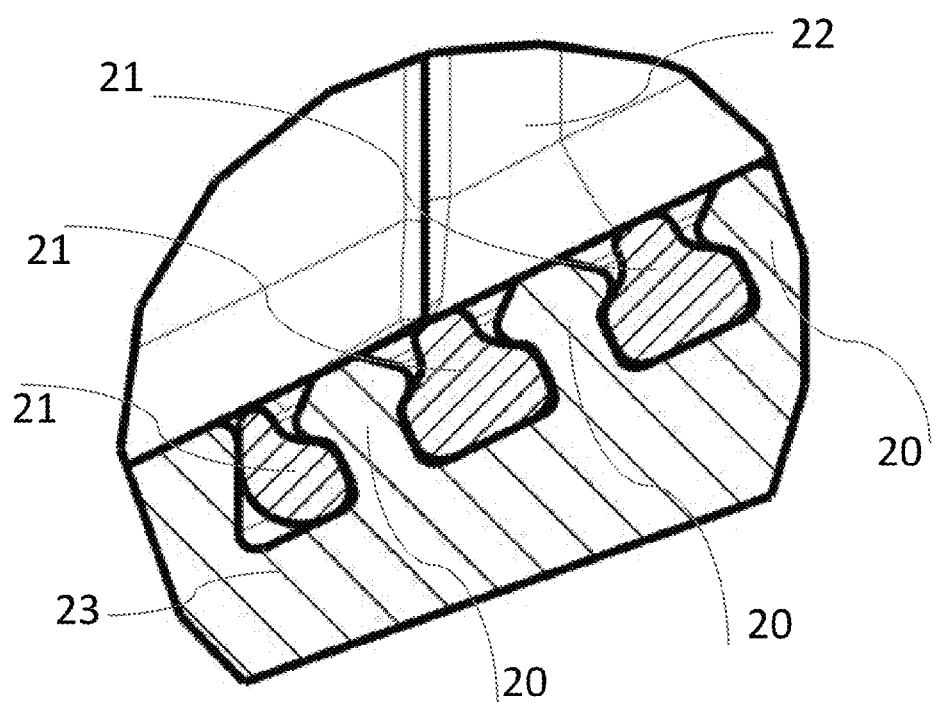
FIG. 8 shows enlarged schematic details of the incremental mechanism with taps and corresponding holes.
Figure 9:
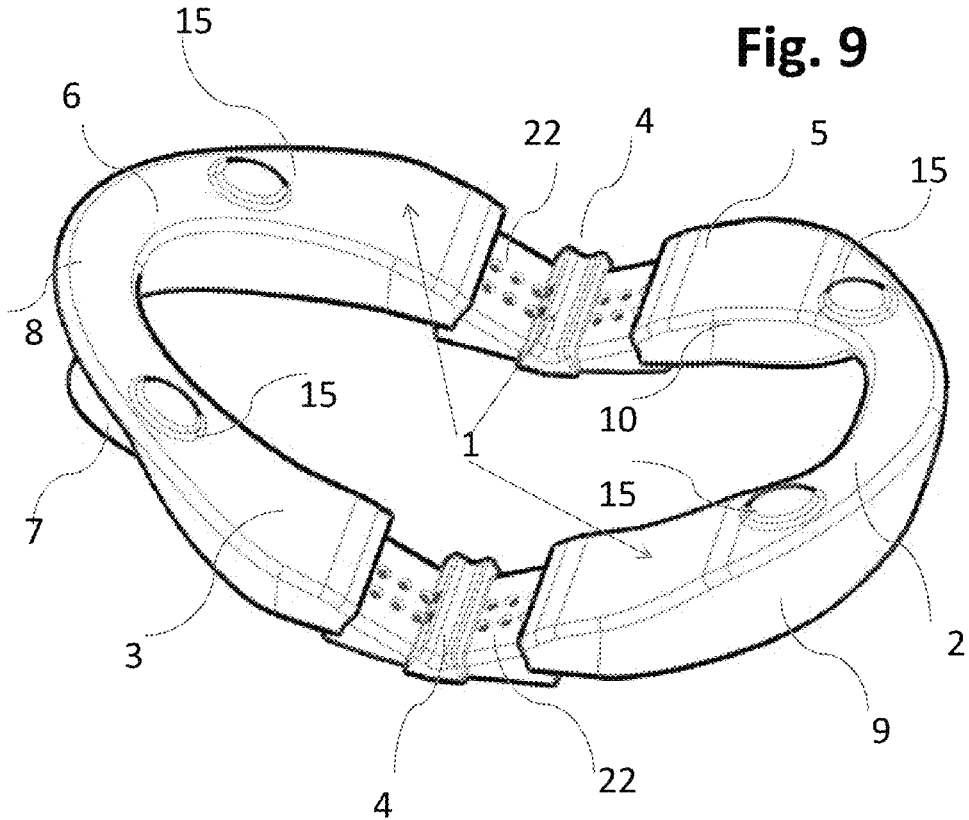
FIG. 9 shows the Incremental version of the Adjustable Mandibular Advancement Device top view in an oblique perspective in its maximal elongated position.
Figure 10:
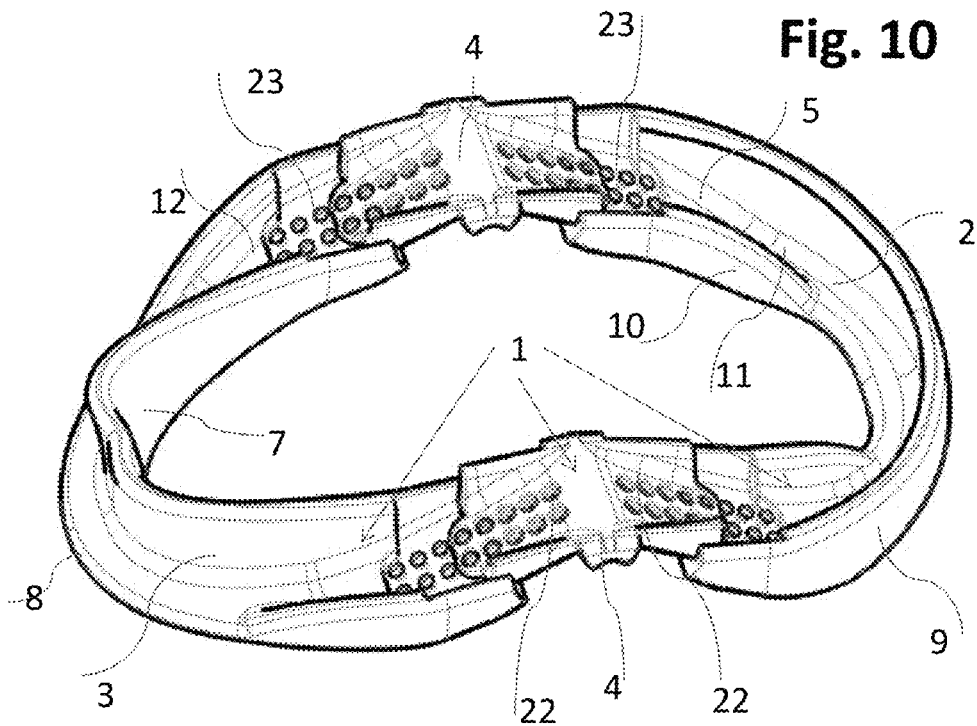
FIG. 10 shows the Incremental version of the Adjustable Mandibular Advancement Device bottom view in an oblique perspective in its maximal elongated position.
Figure 11:
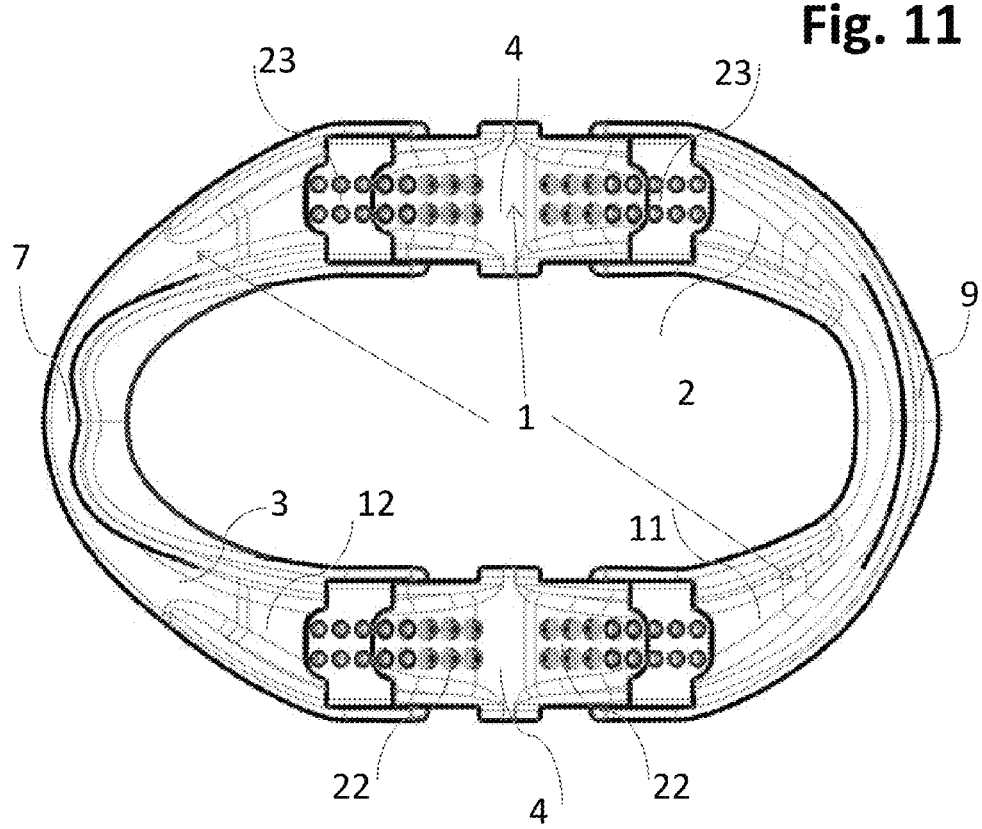
FIG. 11 shows the Incremental version of the Adjustable Mandibular Advancement Device bottom view in a perpendicular perspective in its maximal elongated position.
Figure 12:
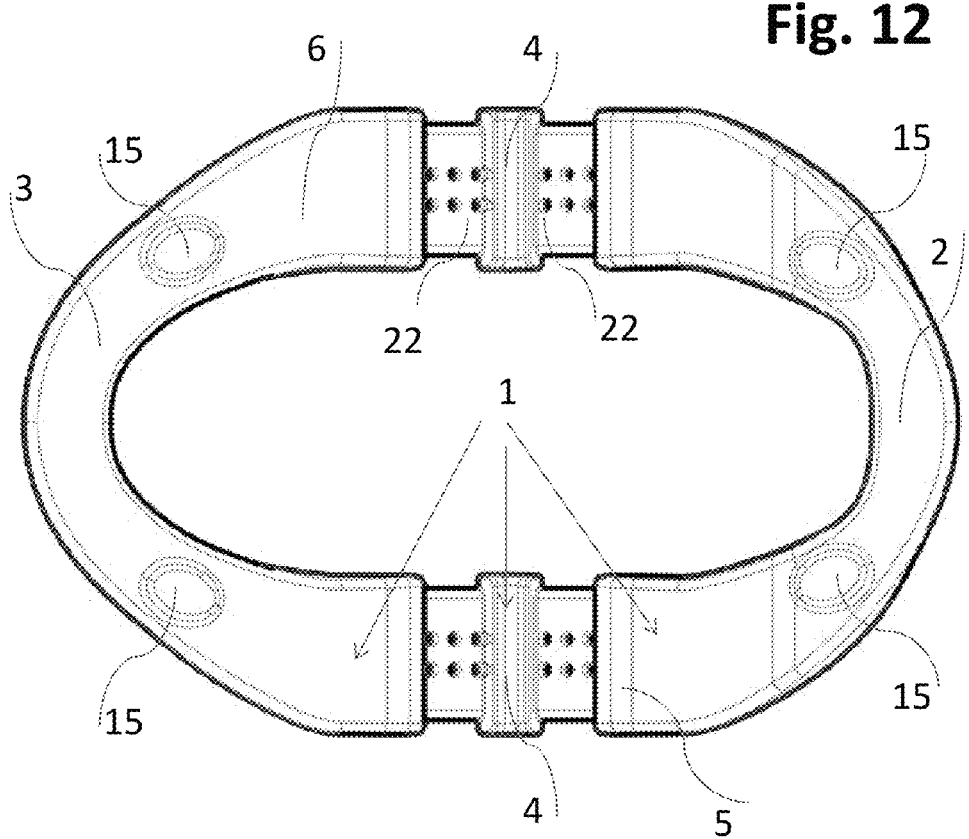
FIG. 12 shows the Incremental version of the Adjustable Mandibular Advancement Device top view in a perpendicular perspective in its maximal elongated position.
Figure 13:
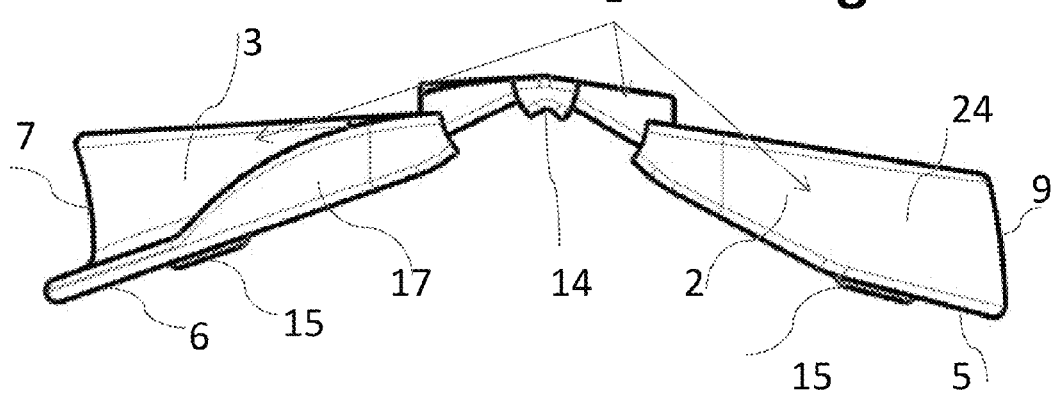
FIG. 13 shows the Incremental version of the Adjustable Mandibular Advancement Device from aside in its maximal elongated position.
Figure 14:
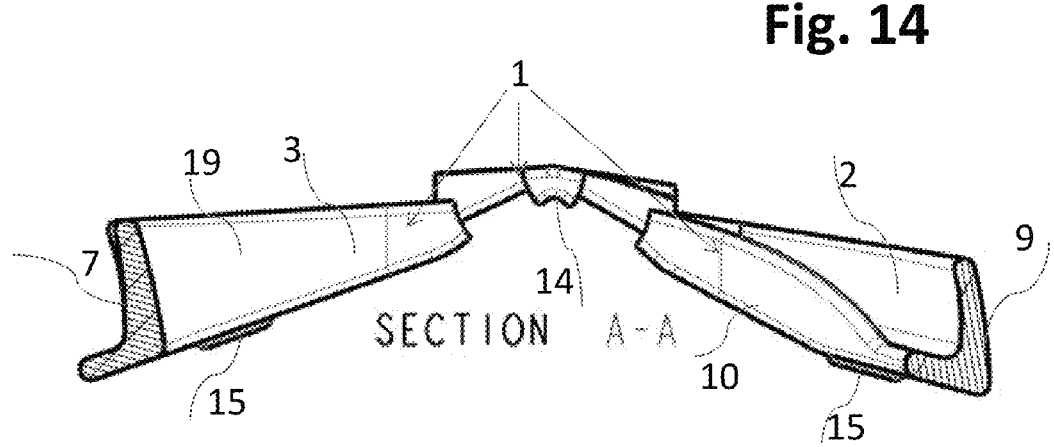
FIG. 14 shows the Incremental version of the Adjustable Mandibular Advancement Device in cross section at line A in FIG. 11 in its maximal elongated position.
Figure 15:
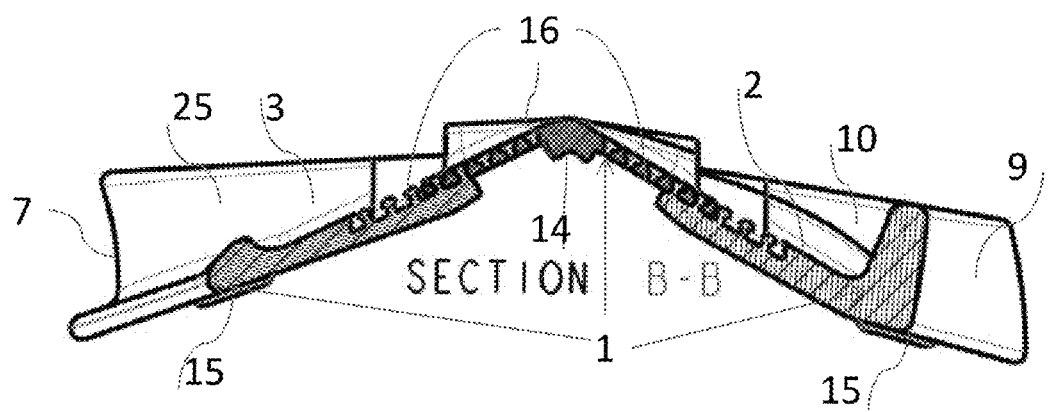
FIG. 15 shows the Incremental version of the Adjustable Mandibular Advancement Device in cross section at line B in FIG. 11 in its maximal elongated position.
Figure 16:
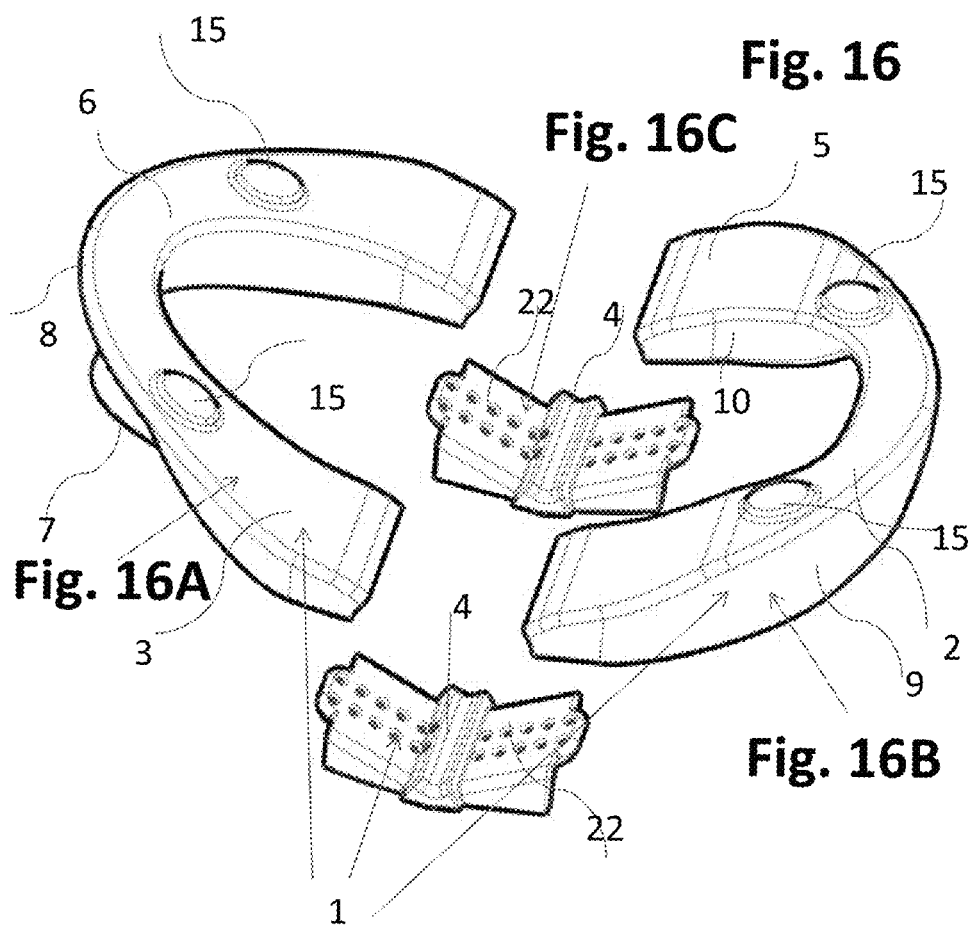
FIG. 16 shows the Incremental version of the Adjustable Mandibular Advancement Device in its four components top view oblique perspective.
Figure 17:
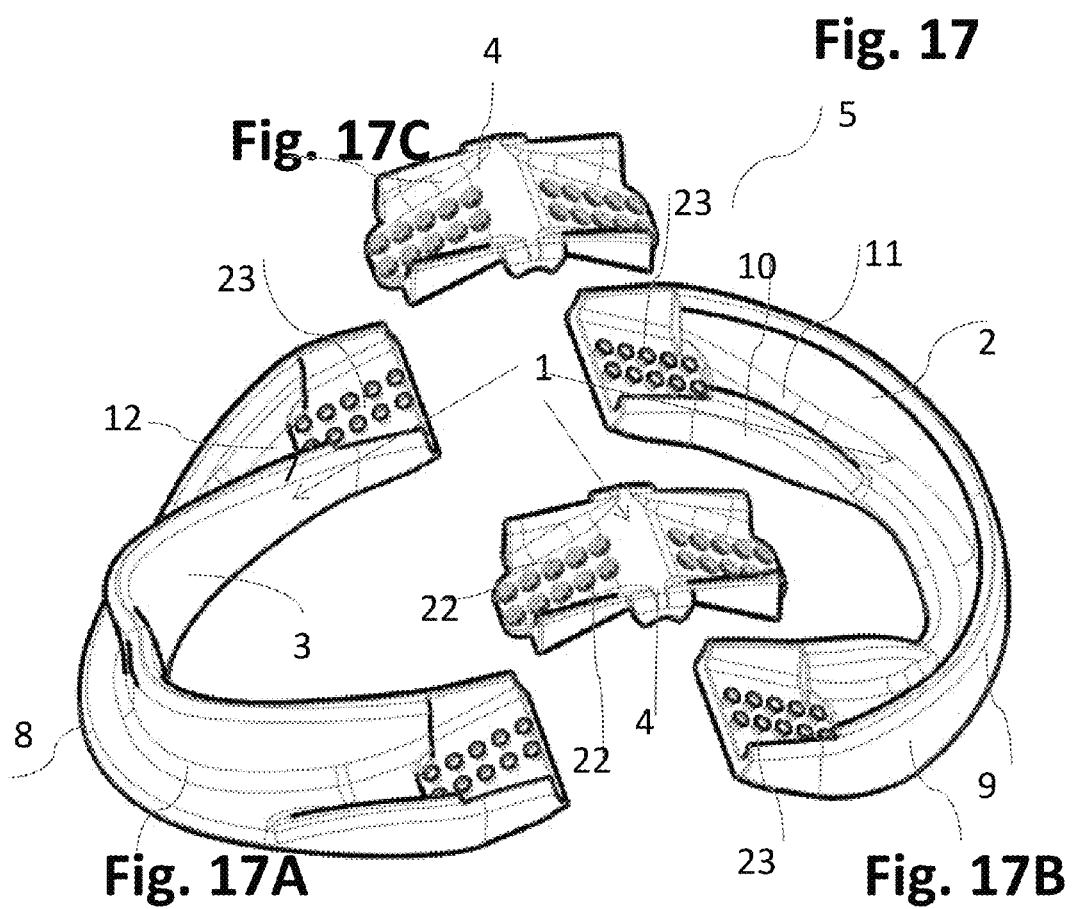
FIG. 17 shows the Incremental version of the Adjustable Mandibular Advancement Device in its four components bottom view oblique perspective.
Figure 18:
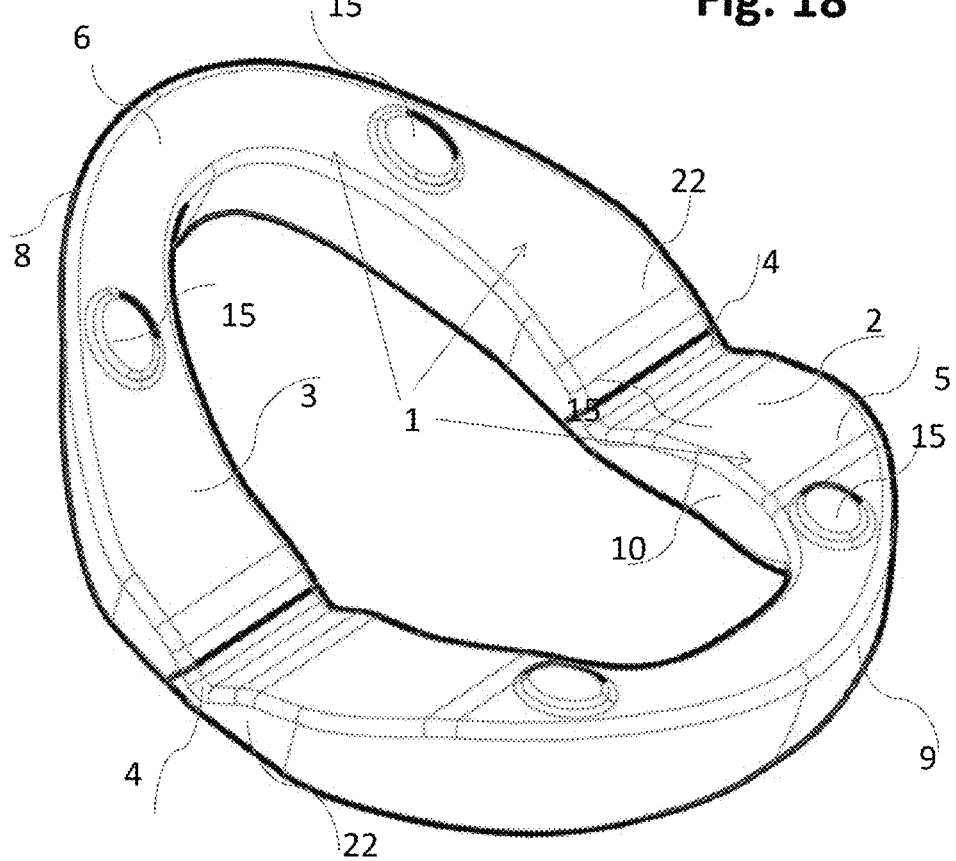
FIG. 18 shows the single member adjustable Incremental version of the Adjustable Mandibular Advancement Device top view in an oblique perspective in its Neutral position.
Figure 19:
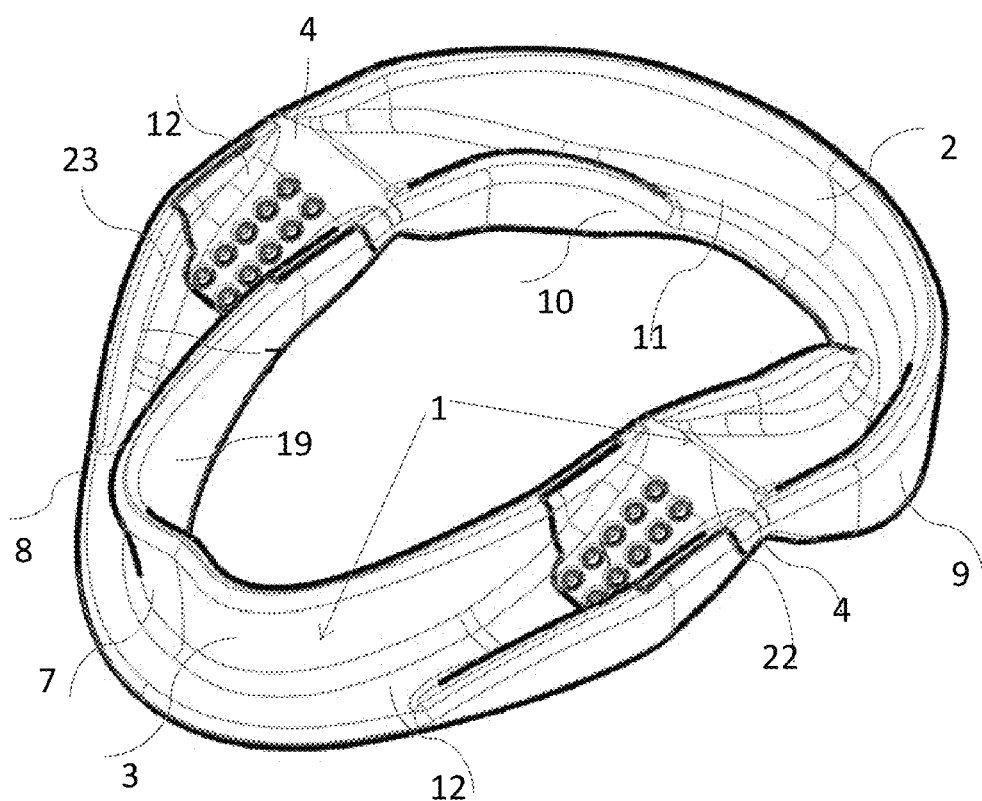
FIG. 19 shows the single member adjustable Incremental version of the Adjustable Mandibular Advancement Device bottom view in an oblique perspective in its Neutral position.
Figure 20:
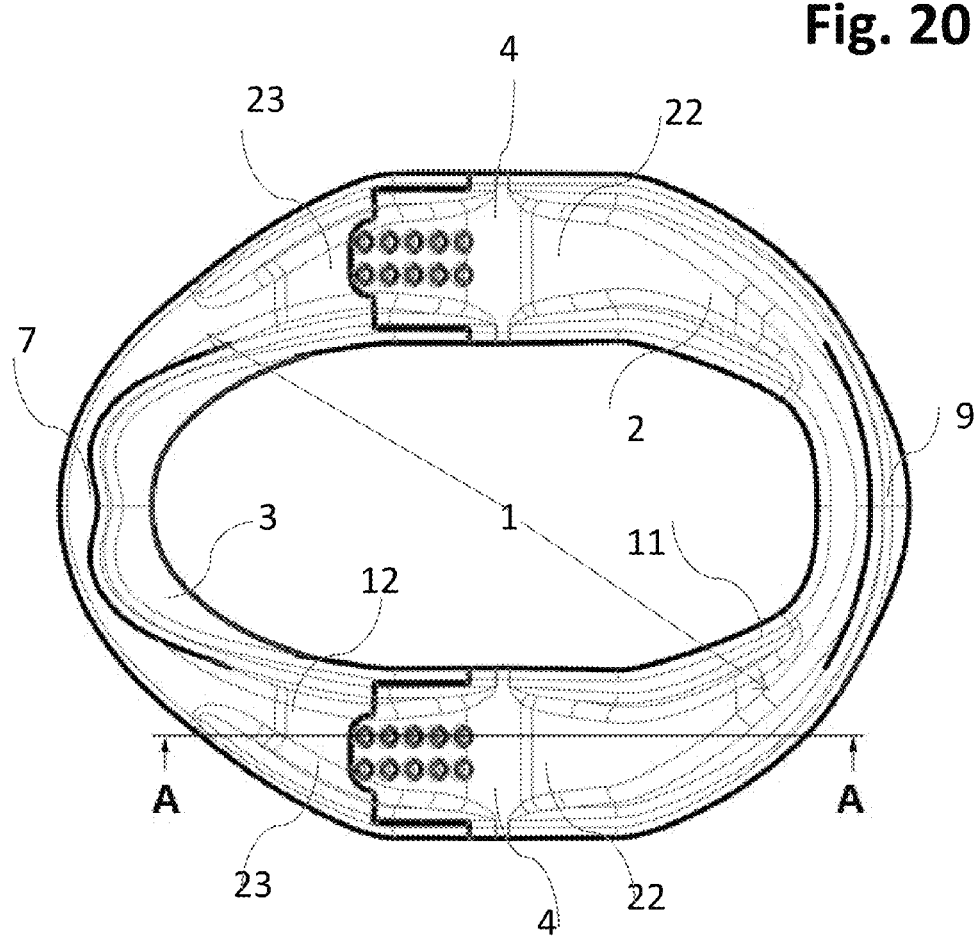
FIG. 20 shows the single member adjustable Incremental version of the Adjustable Mandibular Advancement Device bottom view in a perpendicular perspective in its Neutral position.
Figure 21:
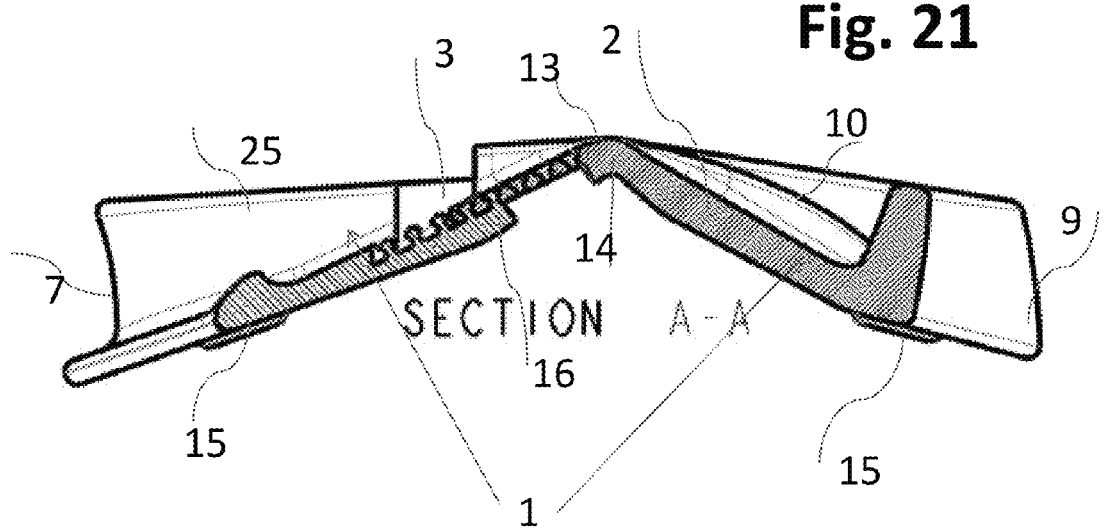
FIG. 21 shows enlarged schematic details of the incremental mechanism with taps and corresponding holes in just one of the members at line A-A in FIG. 20 in its maximal elongated position.
Figure 22:
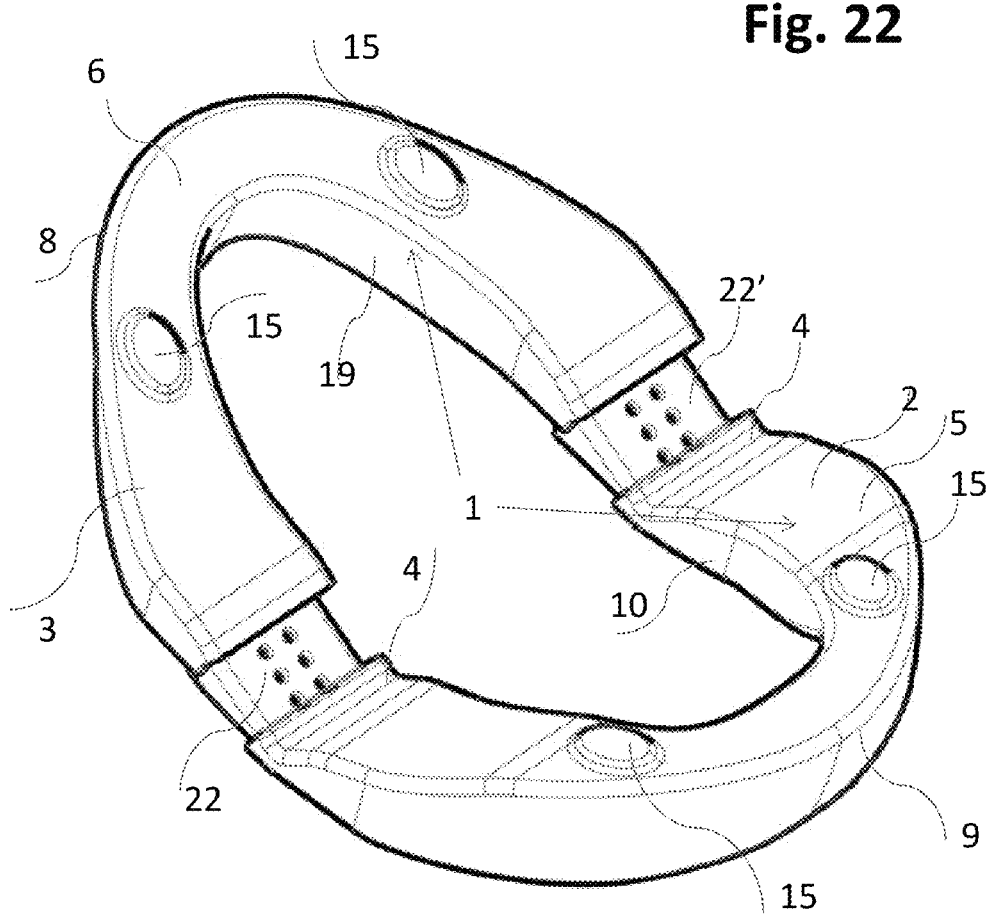
FIG. 22 shows the single member adjustable Incremental version of the Adjustable Mandibular Advancement Device top view in an oblique perspective in its maximal elongated position.
Figure 23:
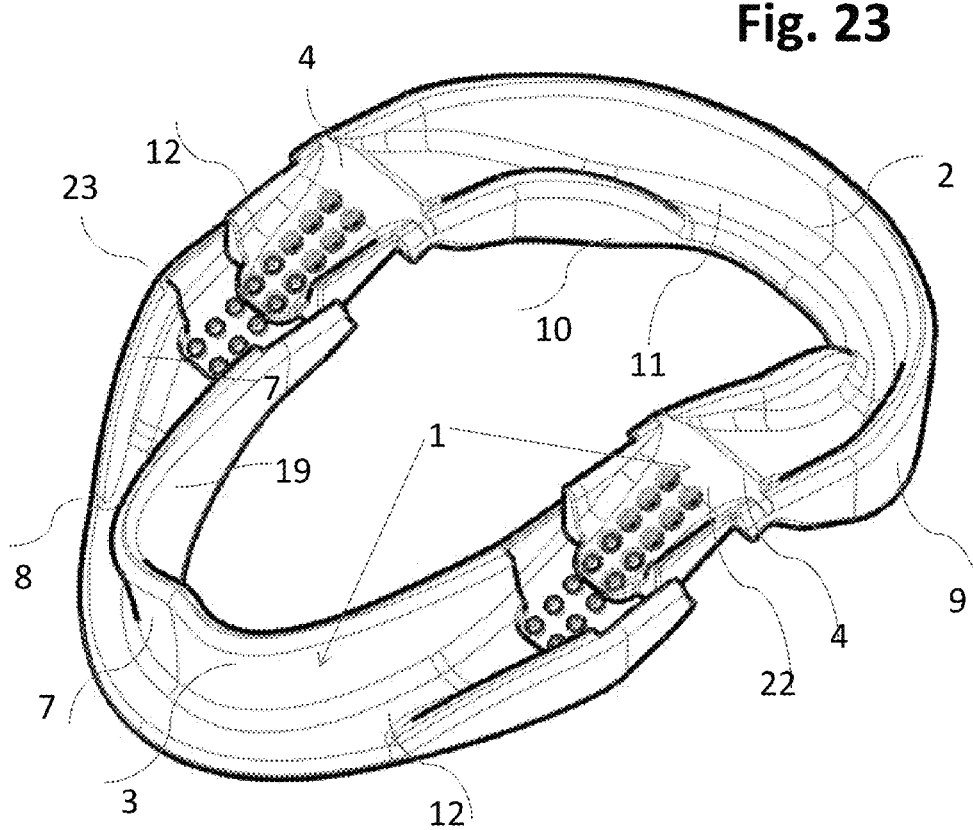
FIG. 23 shows the single member adjustable Incremental version of the Adjustable Mandibular Advancement Device bottom view in an oblique perspective in its maximal elongated position.
Figure 24:
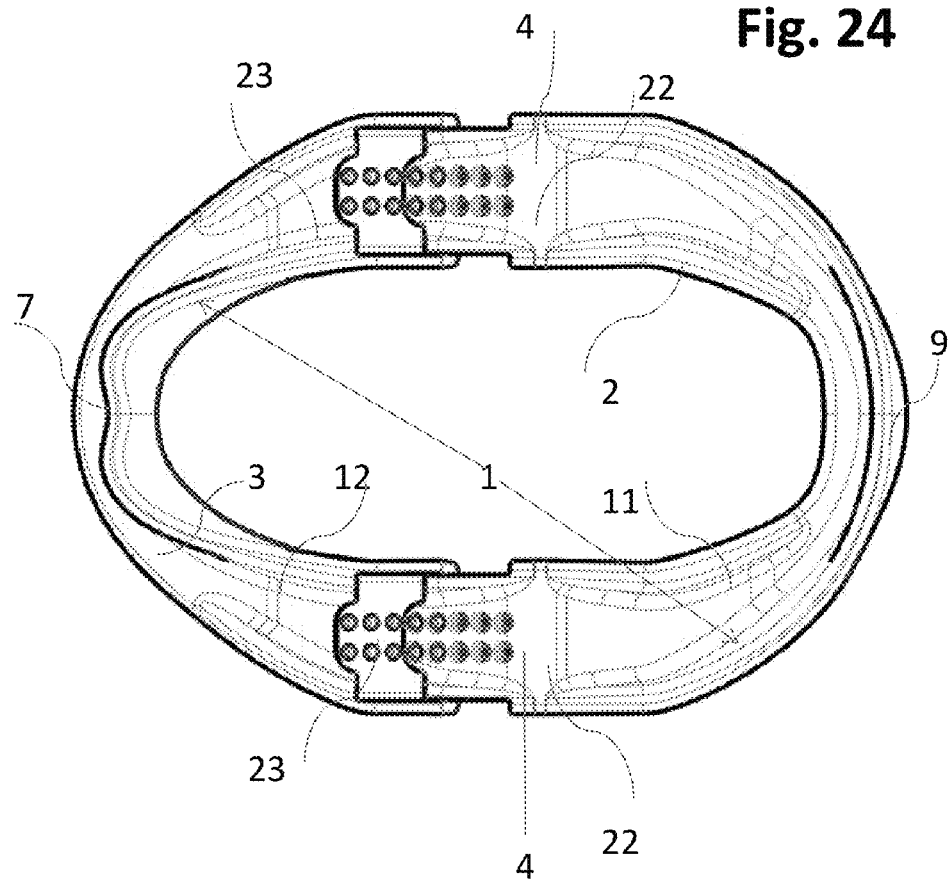
FIG. 24 shows the single member adjustable Incremental version of the Adjustable Mandibular Advancement Device bottom view in a perpendicular perspective in its maximal elongated position.
Figure 25:
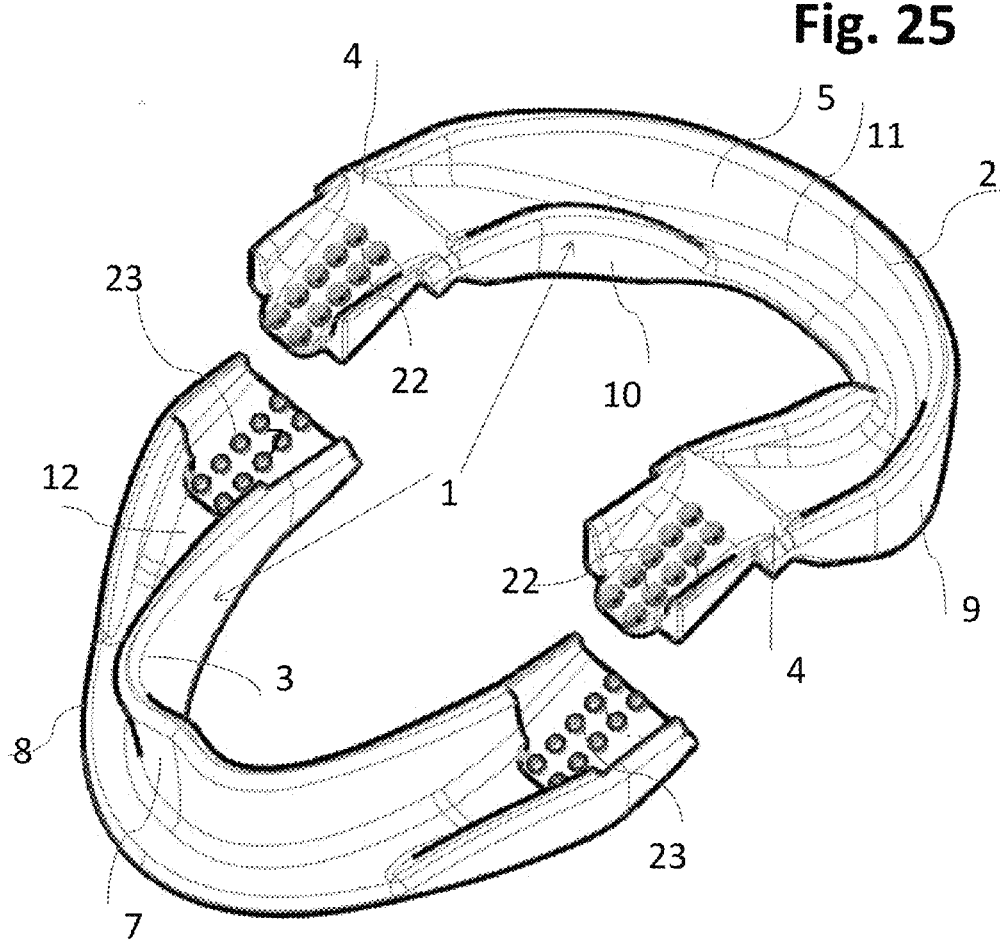
FIG. 25 shows the single member adjustable Incremental version of the Adjustable Mandibular Advancement Device bottom view in an oblique perspective with detached members.
Figure 26:
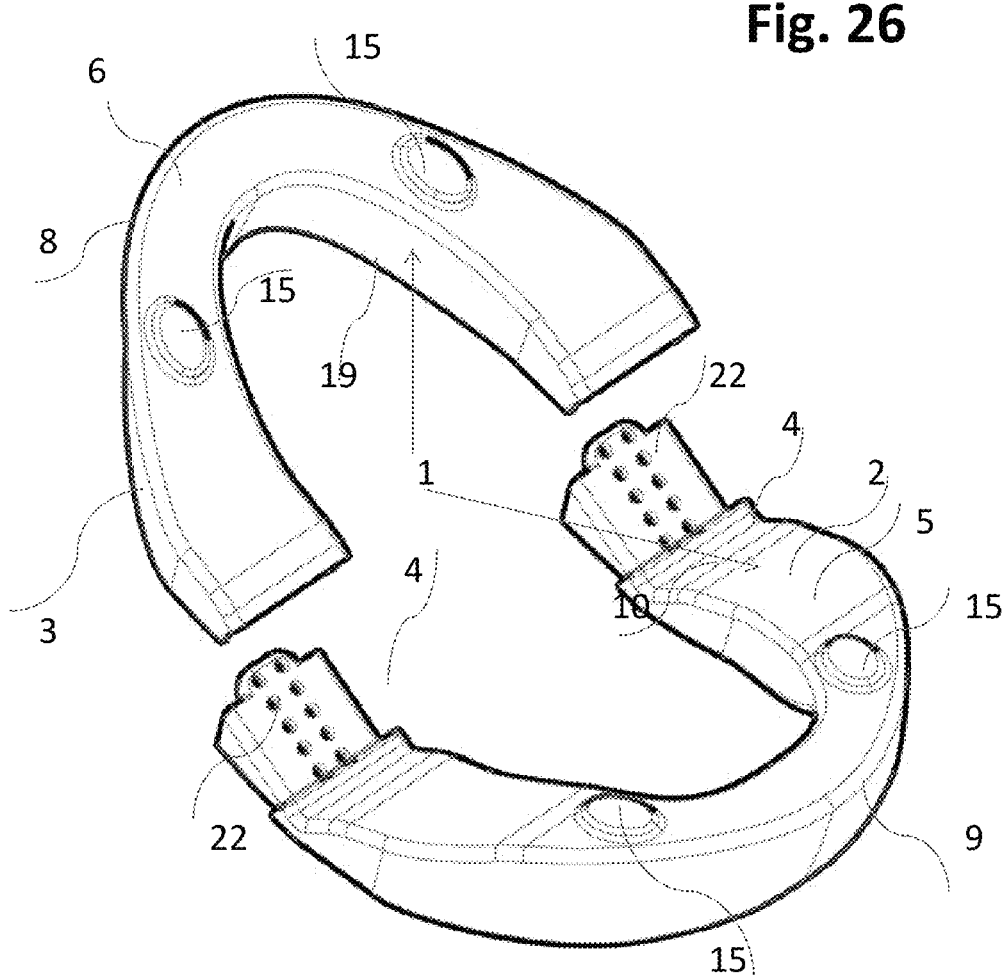
FIG. 26 shows the single member adjustable Incremental version of the Adjustable Mandibular Advancement Device top view in an oblique perspective with detached members.
Figure 27:
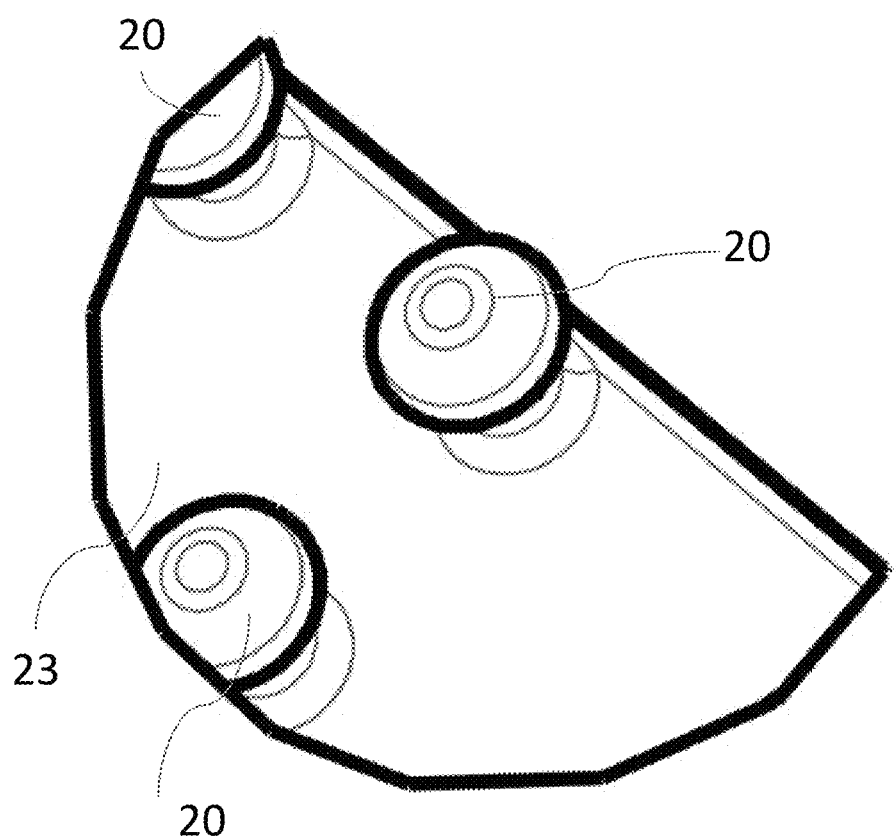
FIG. 27 shows in detail the knob part of the incremental mechanism.
Figure 28:
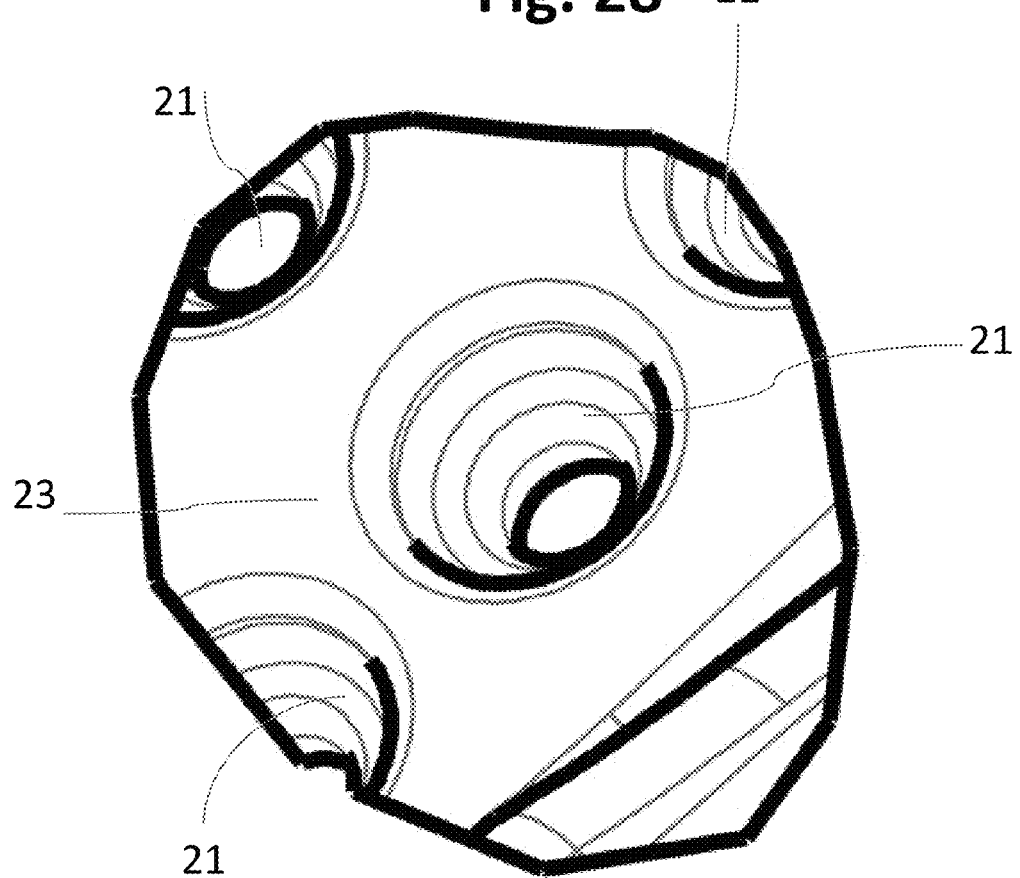
FIG. 28 shows in detail the hole part of the incremental mechanism.
Figure 29:
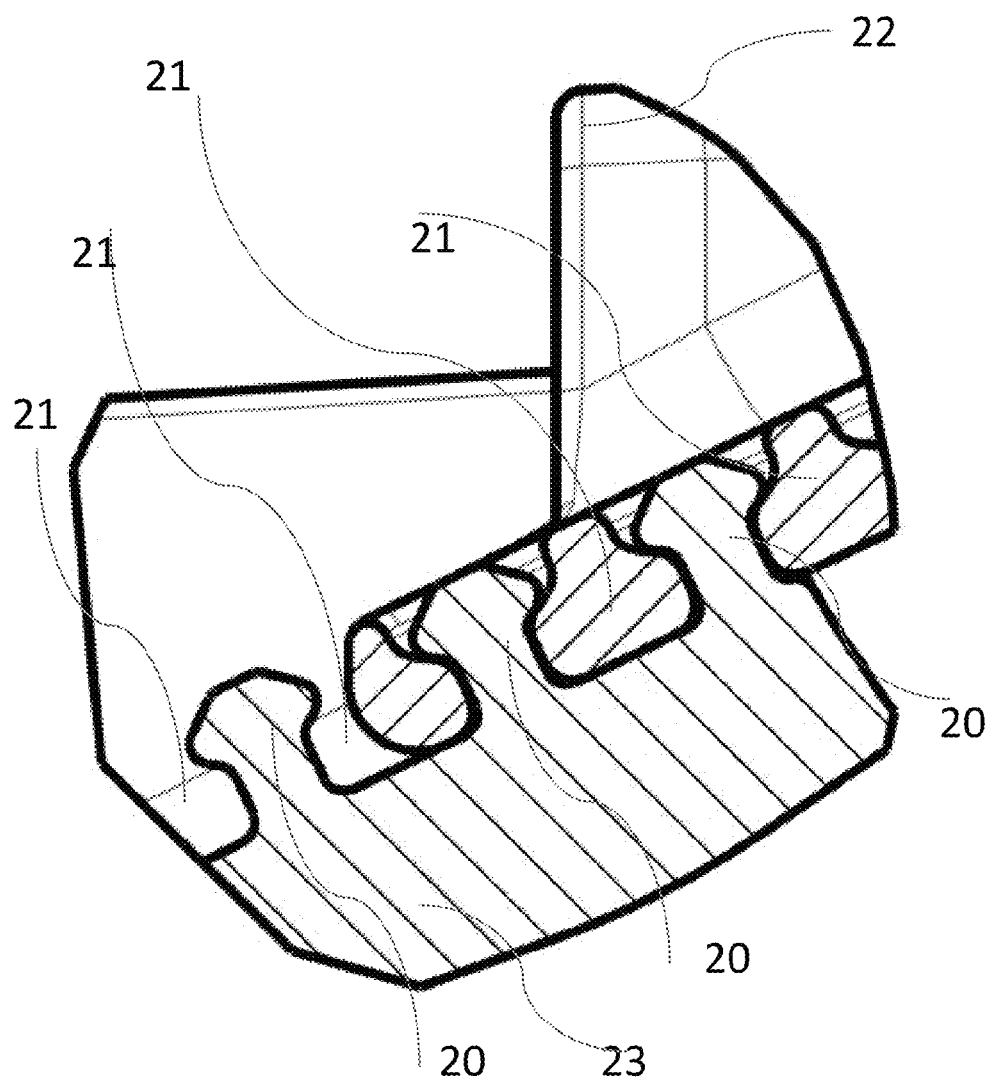
FIG. 29 shows a cross section of the griping mechanism in its maximum enlarged stage.
Figure 30:
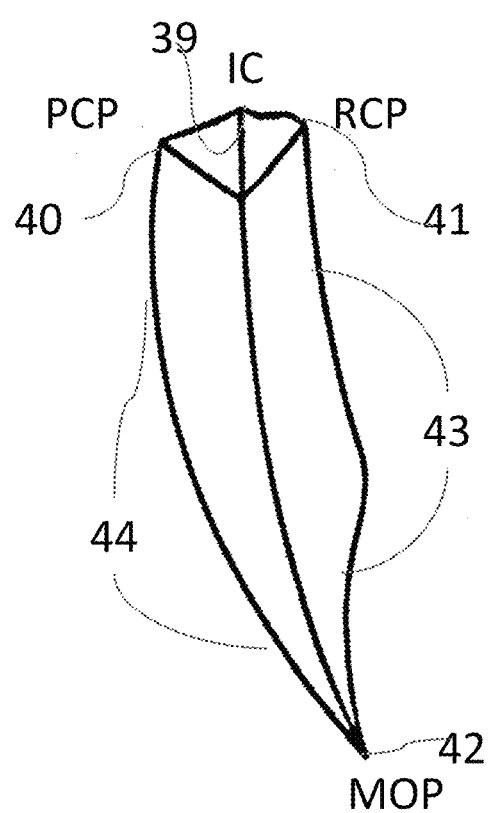
FIG. 30 shows a diagrammatic representation of the limitations of the movements of the lower jaw in any direction in the sagittal plane where PCP stands for the most protruded contact point of the teeth, IC stands for intercuspidal position (the maximal closing point), RCP stands for the most retracted contact position for the teeth, and MOP stands for the maximal opening point.
Figure 31:
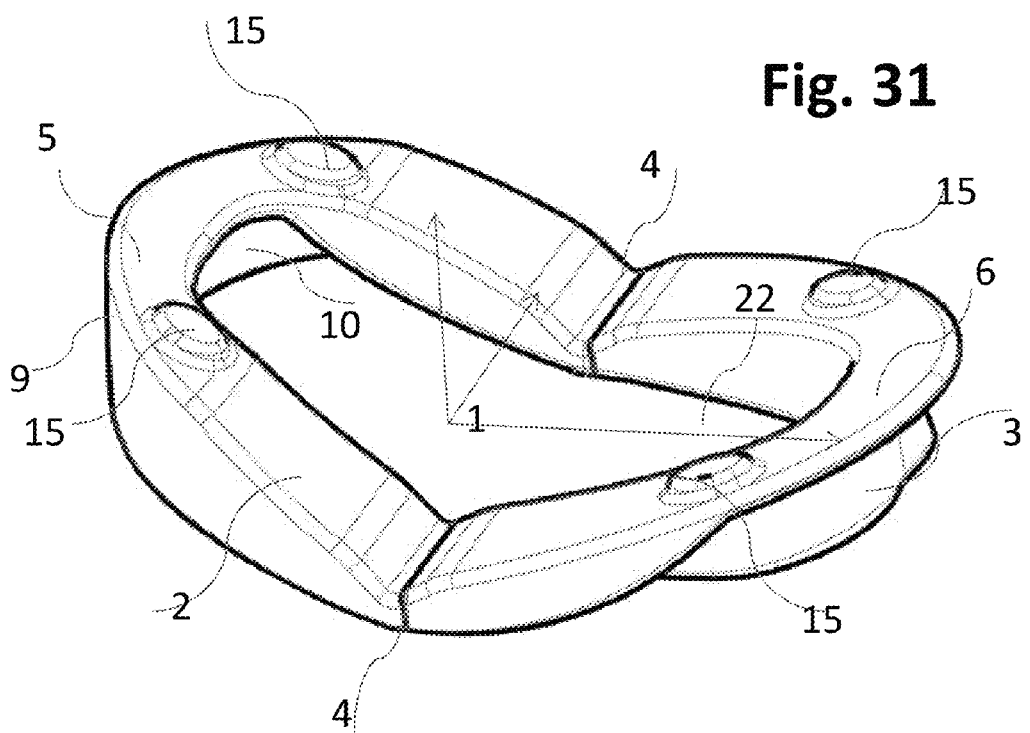
FIG. 31 shows the single member Saw-tag Incremental version of the Adjustable Mandibular Advancement Device top view in an oblique perspective in its Neutral position; note that the essential aspect of the Saw-tag incremental version of the Incrementally Adjustable Mandibular Advancement Device is the fact that the negative structures is lying IN the material and does not penetrate the material as in the previously described version of the Incrementally Adjustable Mandibular Advancement Device.
Figure 32:
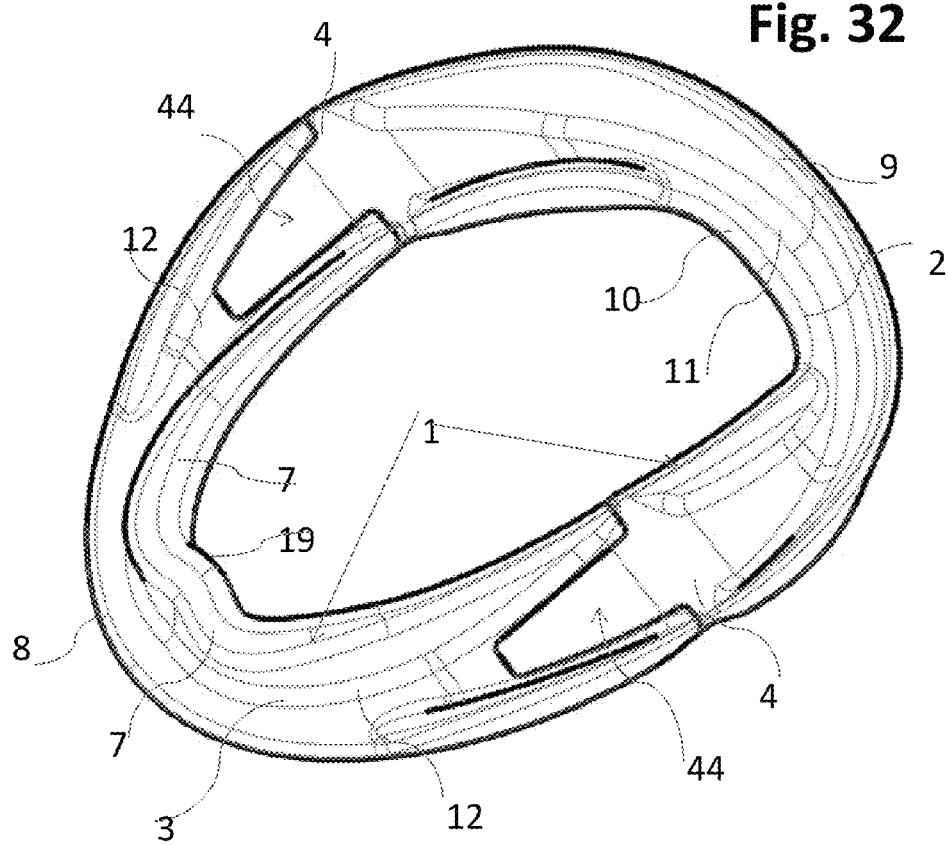
FIG. 32 shows the single member Saw-tag Incremental version of the Adjustable Mandibular Advancement Device bottom view in an oblique perspective in its Neutral position.
Figure 33:
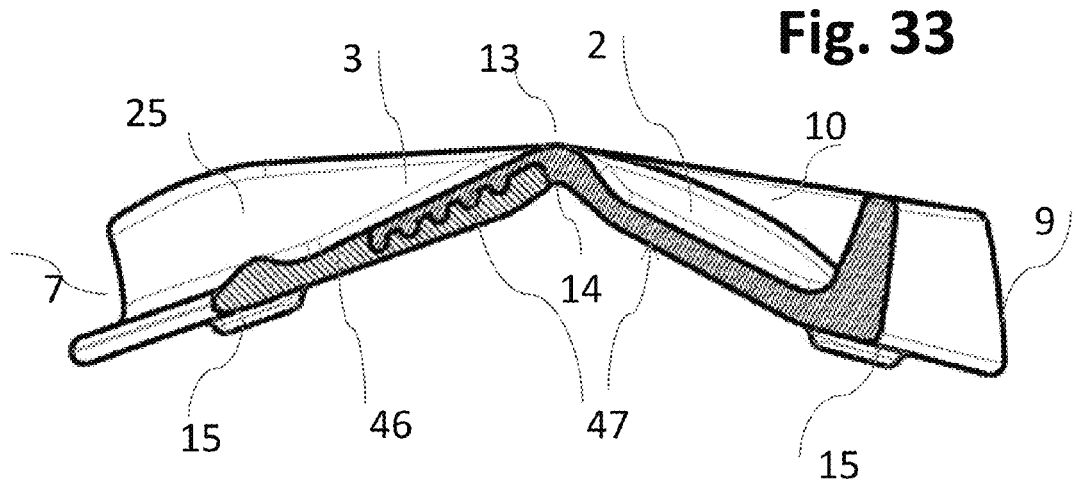
FIG. 33 shows the single member Saw-tag Incremental version of the Adjustable Mandibular Advancement Device in cross section at line B in FIG. 3 in its Neutral position.
Figure 34:
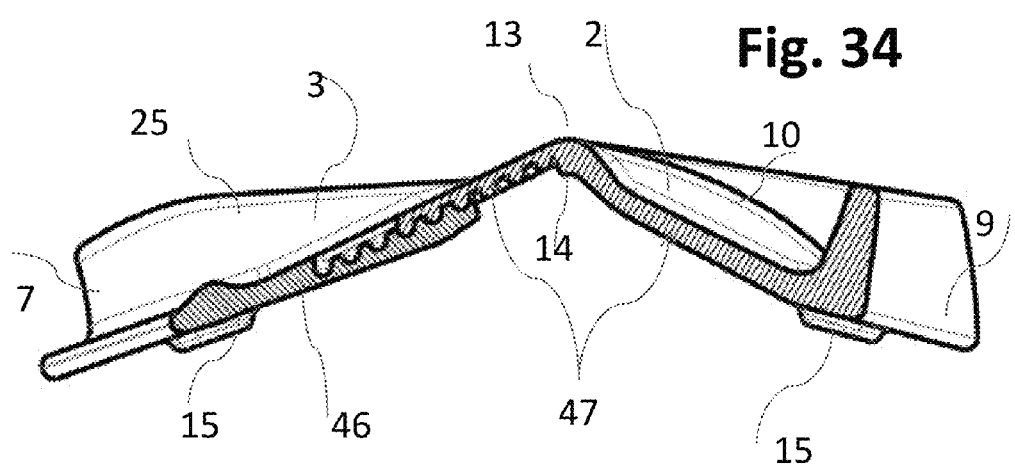
FIG. 34 shows the single member Incremental version of the Adjustable Mandibular Advancement Device in cross section at line B in FIG. 3 in its maximal elongated position.
Figure 35:
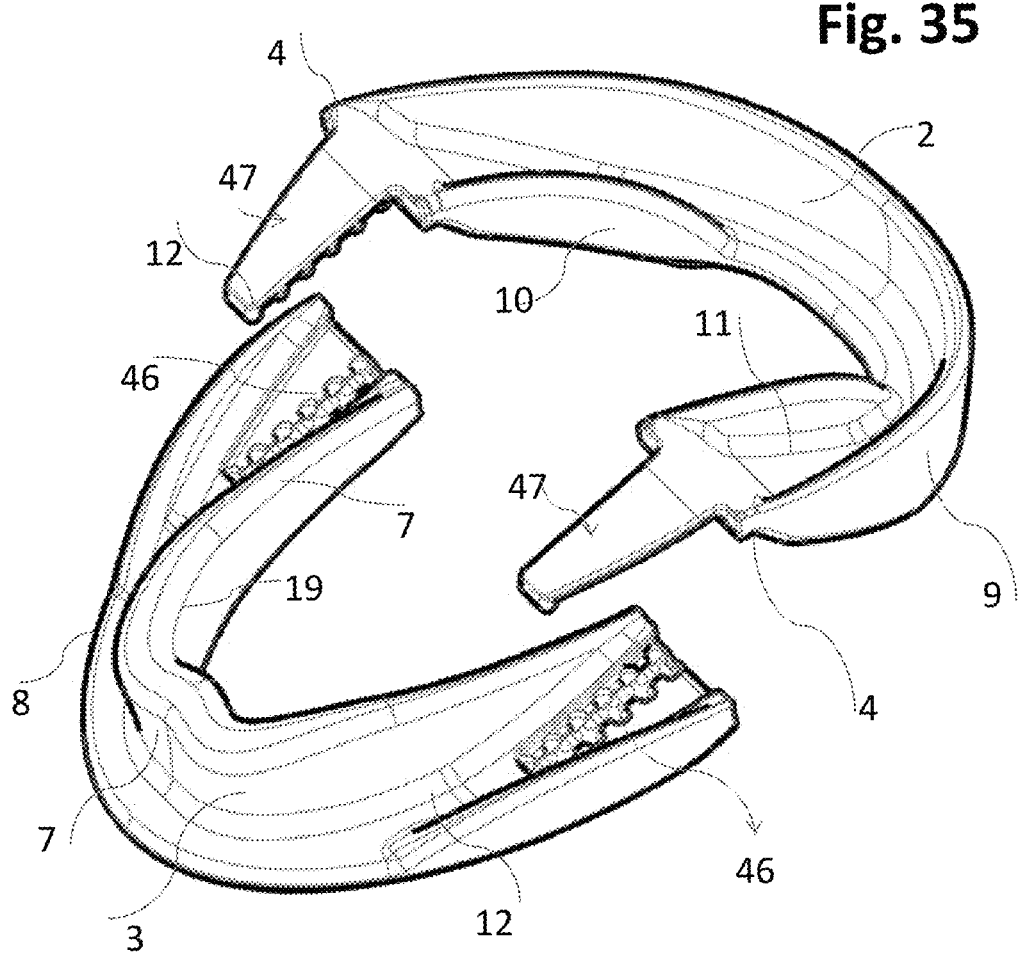
FIG. 35 shows the single member adjustable saw-tag Incremental version of the Adjustable Mandibular Advancement Device bottom view in an oblique perspective in its detached position.
Figure 36:
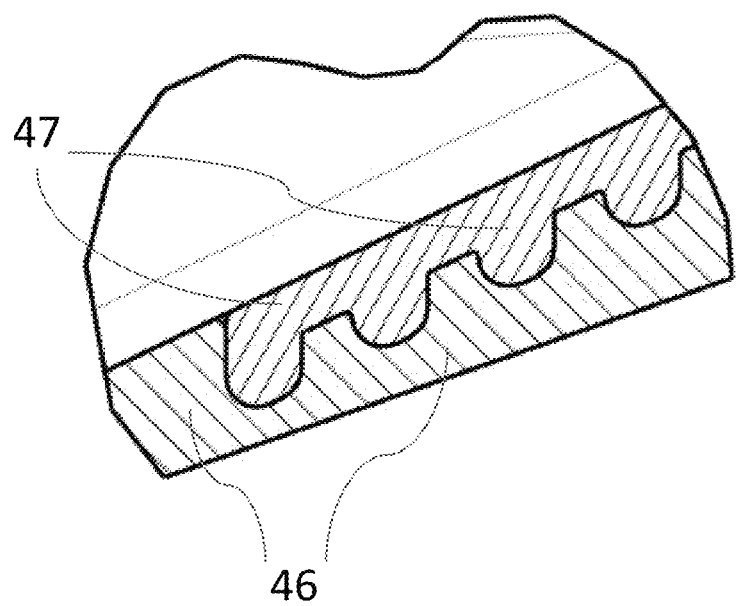
FIG. 36 shows enlarged schematic details of the saw-tag incremental mechanism with positive embedded tabs in the maxillary part and corresponding embedded cavities in mandibular part of the invention.
Figure 37:
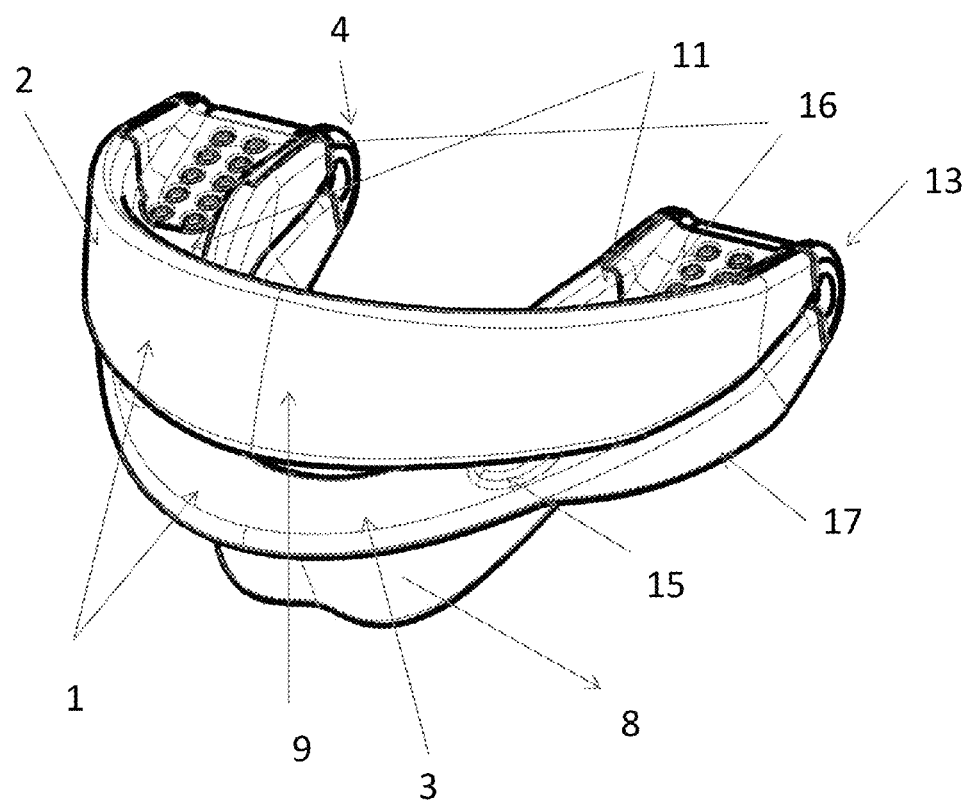
FIG. 37 shows the activated view of the three piece version of the Incremental version of the Adjustable Mandibular Advancement Device shown in FIGS. 1 through 6, and 9-17 in an oblique frontal upper view.
Figure 38:
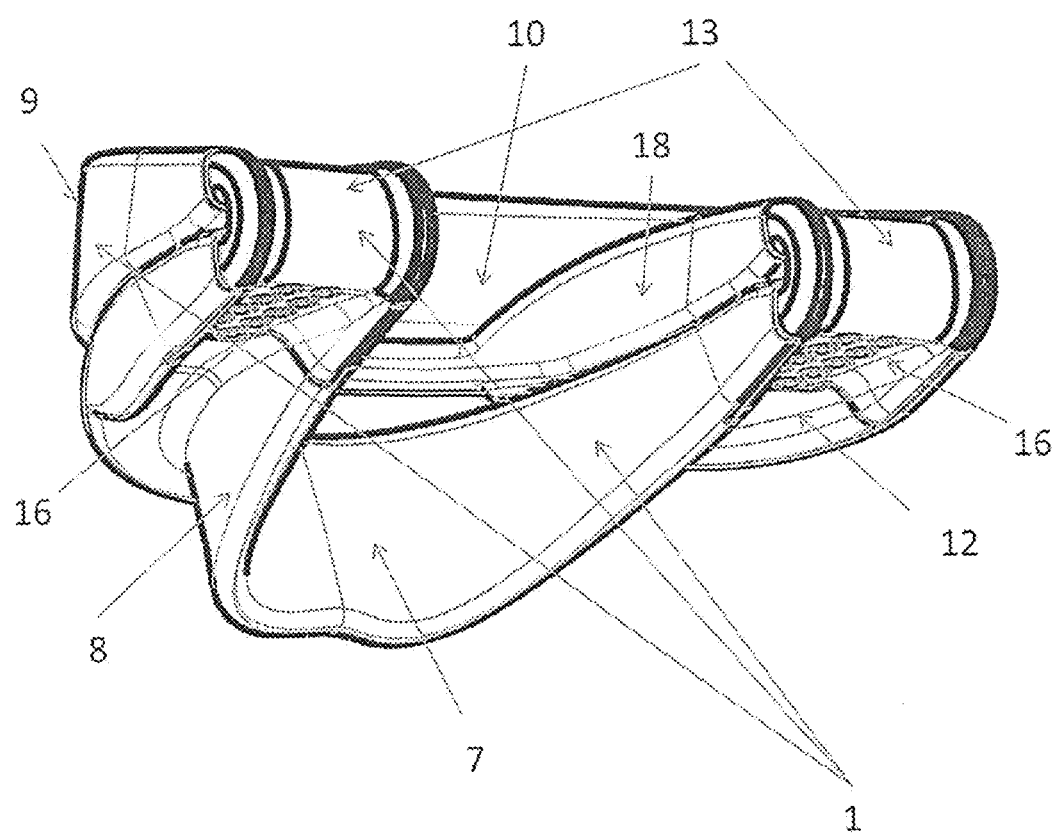
FIG. 38 shows the activated view of the three piece version of the Incremental version of the Adjustable Mandibular Advancement Device shown in FIGS. 1 through 6, and 9-17 in an oblique dorsal lower view.
Figure 39:
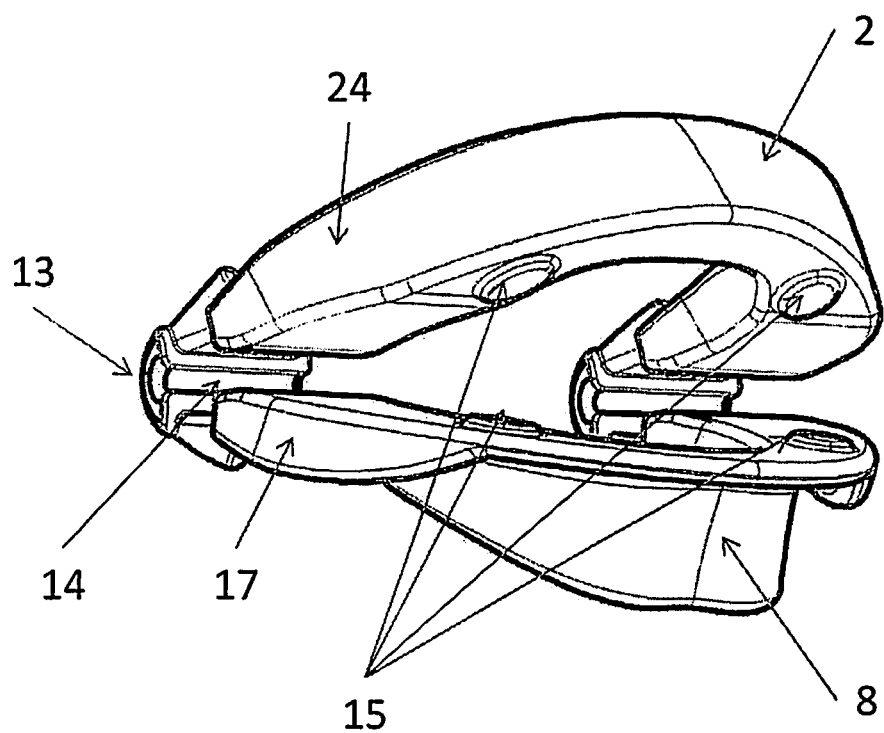
FIG. 39 shows the activated elongated view of the three piece version of the Incremental version of the Adjustable Mandibular Advancement Device shown in FIGS. 1 through 6, and 9-17 in an oblique frontal view.
Figure 40:
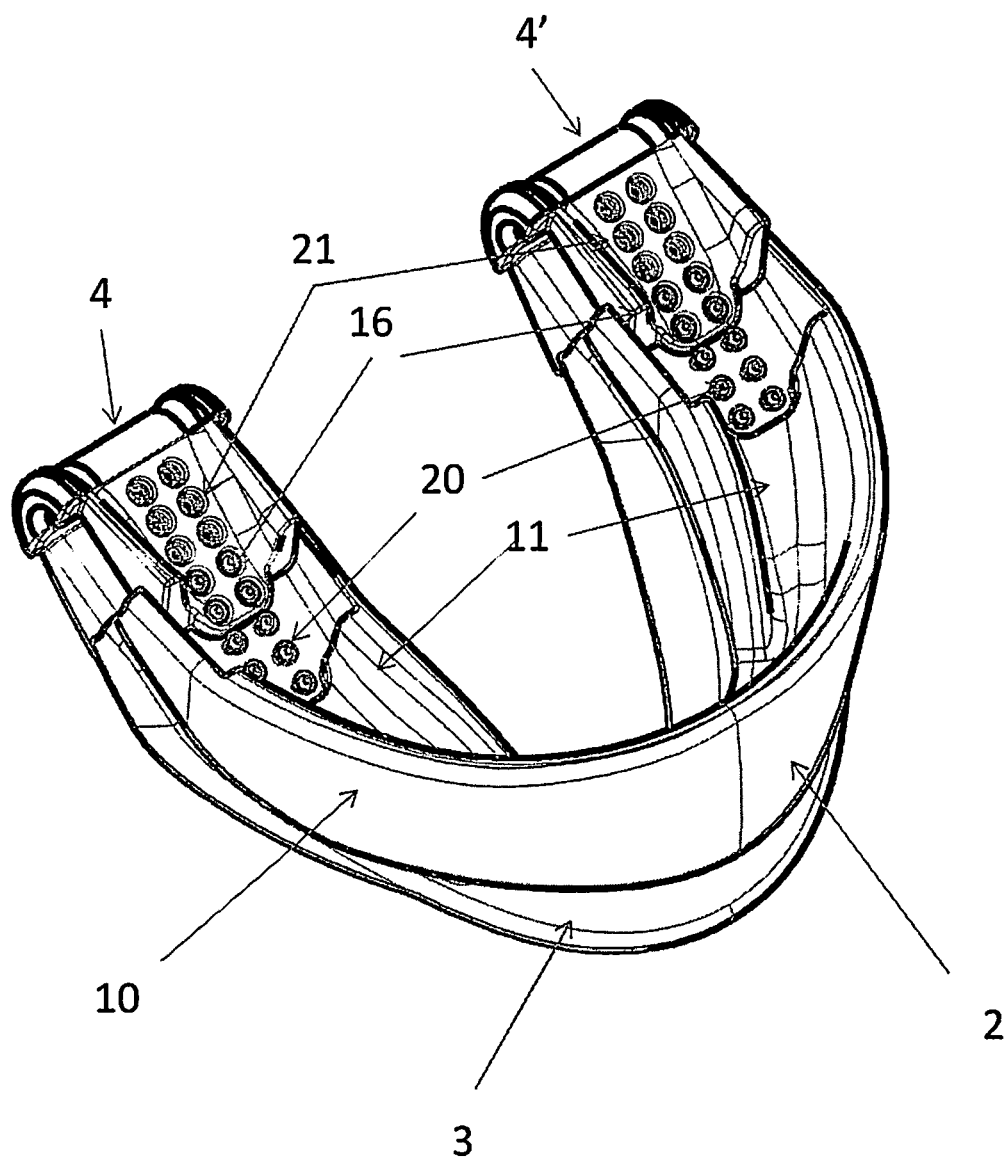
FIG. 40 shows the activated elongated view of the three piece version of the incremental version of the Adjustable Mandibular Advancement Device shown in FIGS. 1 through 6, and 9-17 in an oblique almost cranial view.
Figure 41:
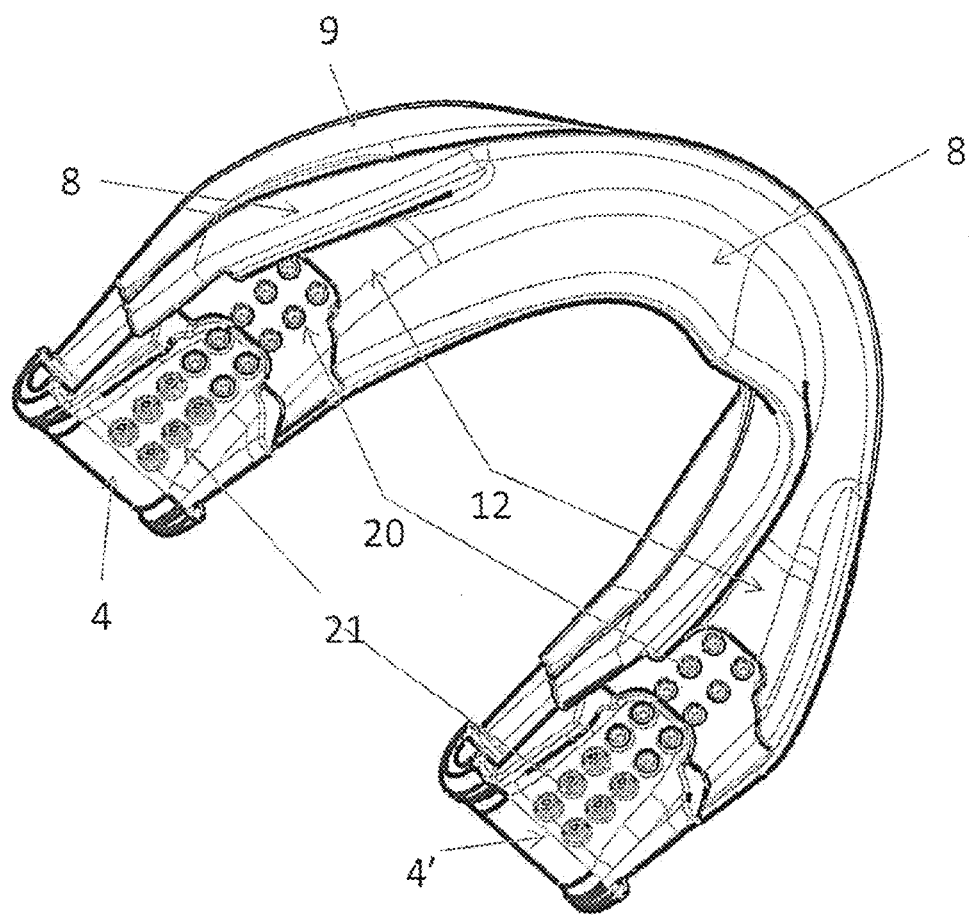
FIG. 41 shows the activated elongated view of the three piece version of the Incremental version of the Adjustable Mandibular Advancement Device shown in FIGS. 1 through 6, and 9-17 in an oblique bottom view.
Figure 42:
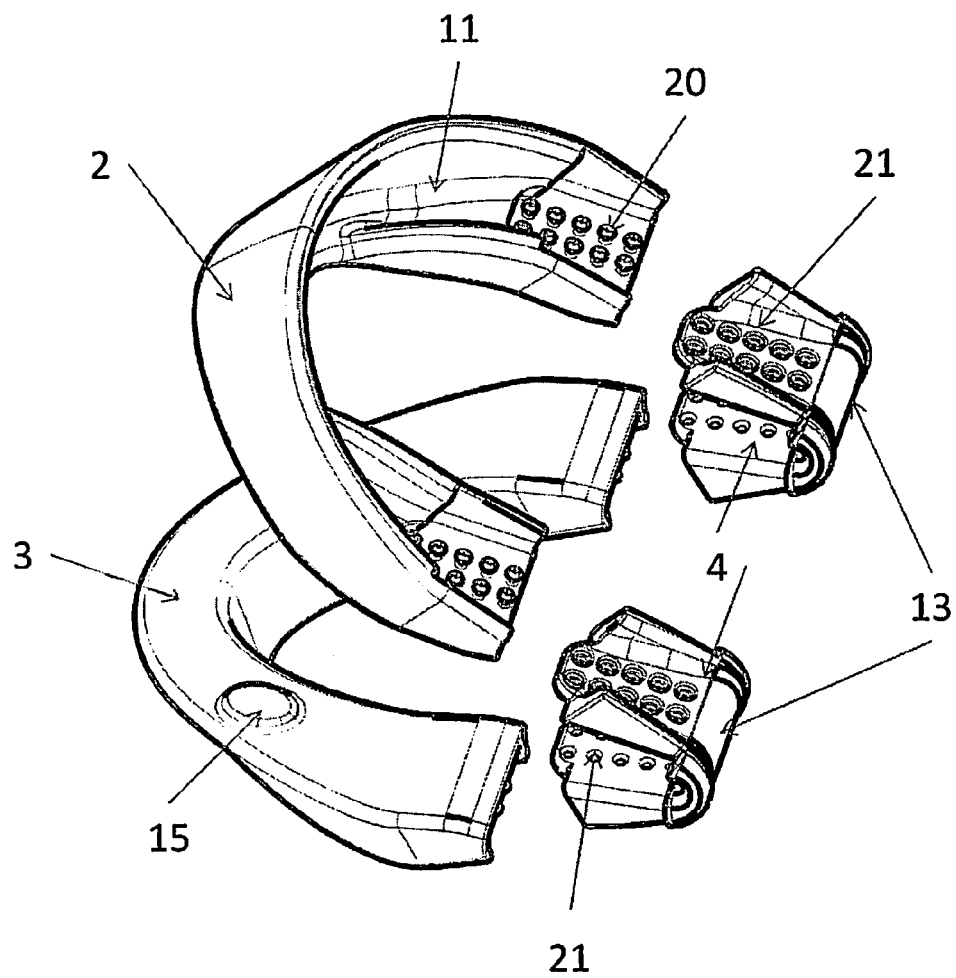
FIG. 42 shows the activated elongated view of the three piece version of the incremental version of the Adjustable Mandibular Advancement Device shown in FIGS. 1 through 6, and 9-17 in an oblique lateral view detached.
Figure 43:
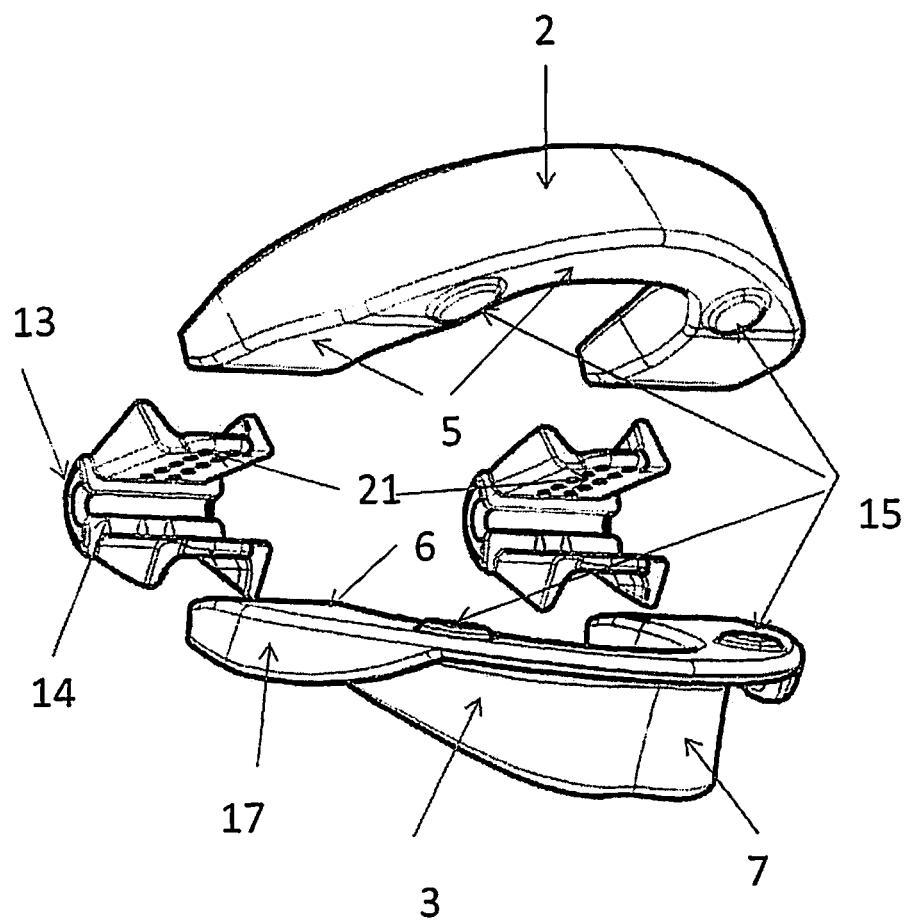
FIG. 43 shows the activated elongated view of the three piece version of the incremental version of the Adjustable Mandibular Advancement Device shown in FIGS. 1 through 6, and 9-17 in an oblique almost frontal view detached.
Figure 44:
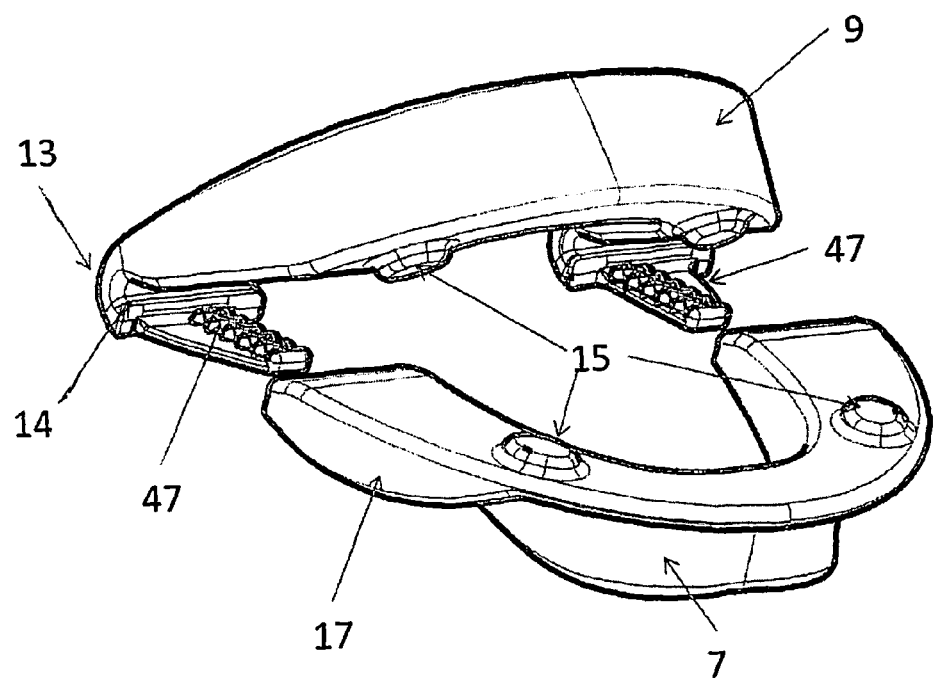
FIG. 44 shows the activated elongated view of the saw-tag version of the Incremental version of the Adjustable Mandibular Advancement Device shown in FIGS. 31 through 35, in an oblique almost frontal view detached.
Figure 45:
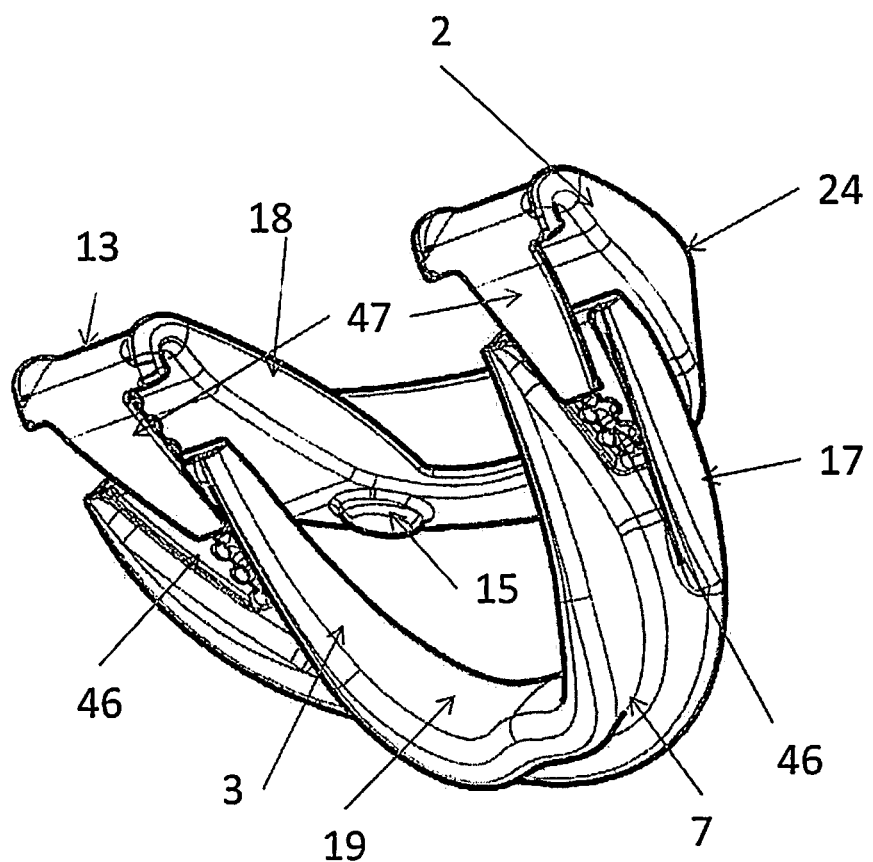
FIG. 45 shows the activated elongated view of the saw-tag version of the Incremental version of the Adjustable Mandibular Advancement Device shown in FIGS. 31 through 35, in a bottom dorsal Oblique perspective detached.
Figure 46:
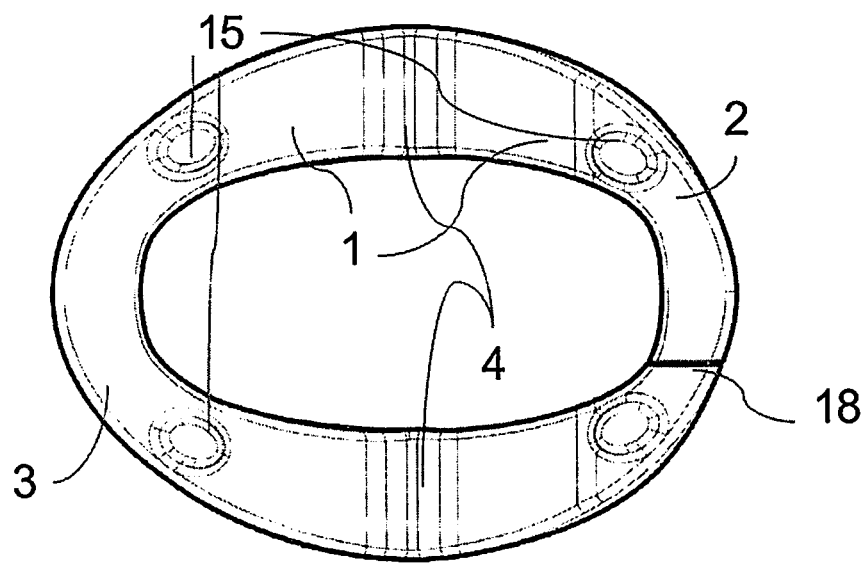
FIG. 46 shows the Midline Maxillary Incremental version of the Adjustable Mandibular Advancement Device top view in a perpendicular perspective in its Neutral position.
Figure 47:
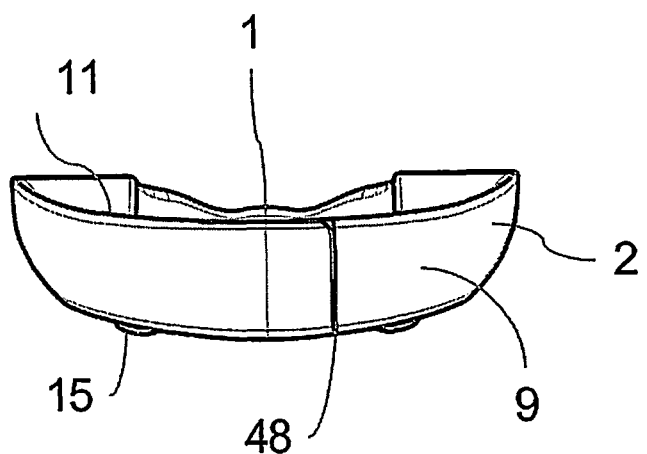
FIG. 47 shows the Midline Maxillary Incremental version of the Adjustable Mandibular Advancement Device front view in its Neutral position (mandibular part not shown here)
Figure 48:
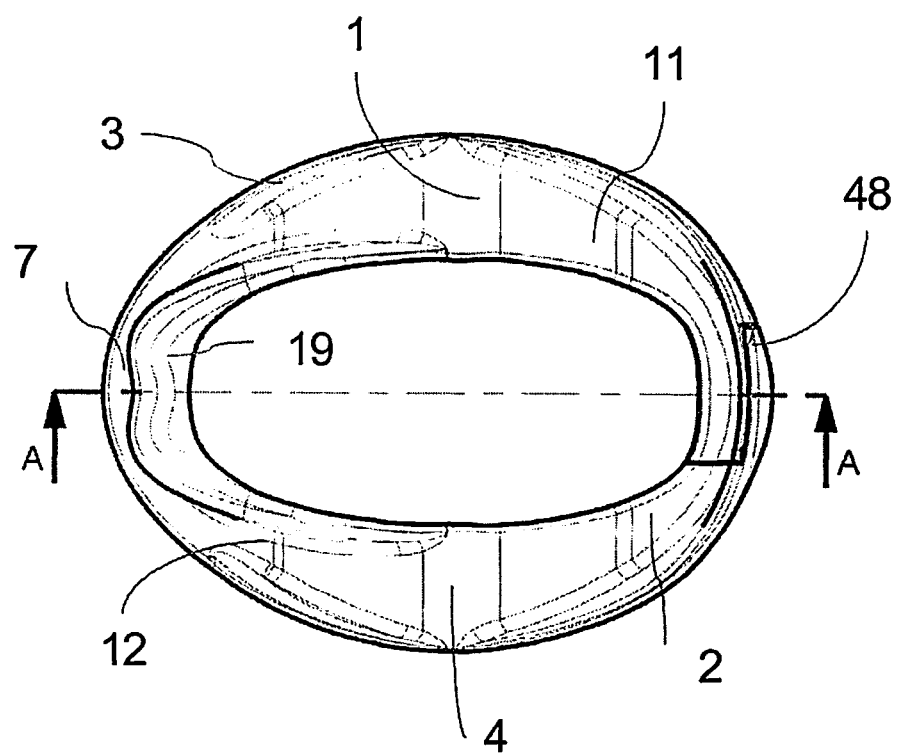
FIG. 48 shows the Midline Maxillary Incremental version of the Adjustable Mandibular Advancement Device bottom view in a perpendicular perspective in its Neutral position.
Figure 49:
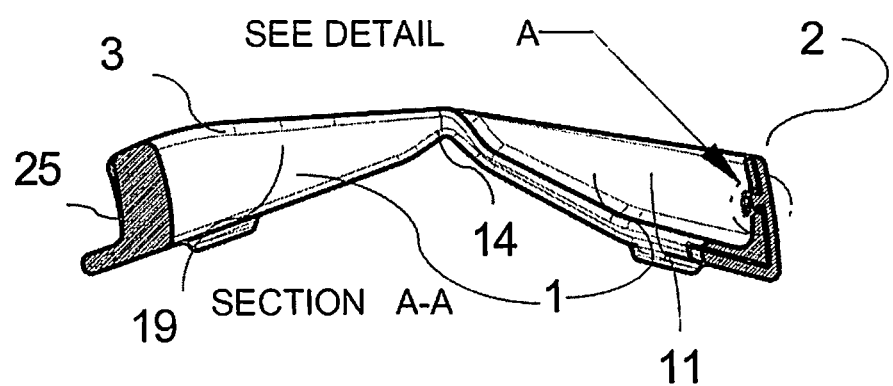
FIG. 49 shows the Midline Maxillary Incremental version of the Adjustable Mandibular Advancement Device sagittal trans-sectional view in the midline shown as line A-A in FIG. 48, in its Neutral position.
Figure 50:
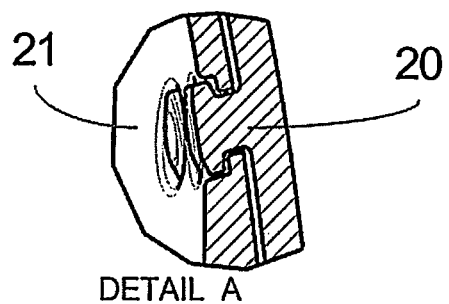
FIG. 50 shows the incremental mechanism with its positive and negative structures interconnected. It can be seen that the two slices of the facial wall of the maxillary part, when joined, exhibits as the original facial wall as seen in FIGS. 1-7, 9-26, 31-35, and 37-45.
Figure 51:
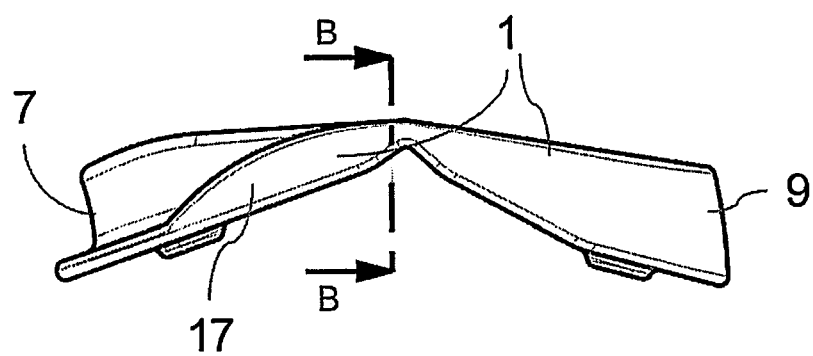
FIG. 51 shows the Midline Maxillary Incremental version of the Adjustable Mandibular Advancement Device side view in a perpendicular perspective in its Neutral position.

The adjustable anti-snore device according to the invention comprises an upper member adapted to engage the maxillary dentition of a human and a lower member adapted to engage the mandibular y dentition of the human, the upper and lower members being resiliently or mechanically hinged together, wherein the resiliency of the hinging is adapted to allow the physiological movement of the lower jaw in the sagittal plane while retaining a forward position of the lower jaw relative to the upper jaw and thereby keeping the airway passage in the nasopharynx, the oropharynx and the hypopharynx substantially free of occlusion, while at the same time embody the adjustability in one or two form, i.e. incremental and/or successive.

The device according to the invention combines three essential functions: the forward positioning of the lower jaw relative to the upper jaw, the hinging, and the adjustability of the sagittal relation between the two members. As will be explained below, the forward positioning of the lower jaw is essential to prevent occlusion of the airway passage in the pharyngeal space during sleep. The resilient or mechanically hinging makes it possible and realistic to maintain the forward positioning of the lower jaw even during movements in the sagittal plane which unavoidably occur during sleep. And the adjustability makes it useful for even the smallest and the largest person wearing the device. This essential combination of features which ensures constant non-constricted airflow and unrestricted movement in the sagittal plane and thereby ensures a constant efficient function without risk of the device falling out of the mouth of the user and without any substantial discomfort together with the adjustability which even allows some horizontal movements, distinguishes the device according to the invention from all of the abovementioned prior art devices.

The device according to the invention may be made of any material, such as metal, alloy, wood, plastics, etc provided that the device made feels soft and comfortable in the mouth without any constriction or damaging of the tissue, such as gums, tongue, teeth, but at the same time is sufficiently capable of retaining its shape and of exerting a sufficient resiliency towards the muscular tension and forces acted upon the jaws so that it will maintain the lower jaw in the anterior position while allowing normal movements during sleep. The material used for the device according to the invention should not contain any allergens or other kind of toxic ingredients.

The device according to the invention is preferably made of a resilient non-toxic plastics material, such as a polyvinyl resin, including a vinyl acetate-ethylene copolymer such as poly (ethyl vinyl acetate), or a polyethylene or polypropylene.

It is particularly preferred that the resilient non-toxic plastics material is a thermoplastic material, such as a cellulose derivative, a vinyl polymer, a polystyrene, a polyamide, an acrylic resin, etc., which can be shaped to adapt to an individual dentition by moderate heating, such as heating to a temperature above normal human body temperature, that is, a temperature of at least 40° C. and at the most 80° C., e.g. about 70° C. The material presently most preferred by the inventor is ethylene vinyl acetate copolymer.

The device according to the present invention may be manufactured by plastics molding, such as cold molding, compression molding, injection molding, etc. The manufacturing method presently most preferred by the inventor is injection molding.

The upper and lower members are preferably integrated with each other through resilient hinges made of the same material as the upper and lower members. However, the hinges may be reinforced and their resiliency enhanced by insertion, such as cast in, etc., into the hinges of a resilient member, such as a resilient plastics member, a metallic resilient member, such as a flat spring, a laminated spring etc. etc., or simply by a mechanical connection.

The adjustability according to this invention, being embedded or glued, gilded or otherwise attached to the membering parts for the engagement of the dentition, in the upper maxillary member, the lower mandibulary member or both members at the same time, being incremental is a major novelty and is unique for this device.

As it will be understood the adjustability is embedded in the anterior parts of the upper and/or lower members of the device thus keeping the posterior resilient or mechanic hinge intact.

The adjustability of the protrusion of the mandible relative to the maxilla is made adjustable by the means of embedding a positive structure in either the forward moving part of the device and a negative structure in the stable part of the device or vice versa. The positive part may be constructed as a knob, rod, hook or alike, whereas the corresponding negative structures would be holes, cylinders and loops in this aspect. Other configurations may apply. Thus regardless on the structure selected, knob, rod or hook etc. the adjustability will express itself as an incremental (stepwise) adjustable mandibular advancement device.

One aspect of the invention is a device in which the incrementally adjustable mechanism is embedded in the mandibular part of the device so the mandible can be protruded when the knobs and holes are detached from its original position and reattached in a more advanced longitudinal form of the mandible part of the device.

Another aspect of the device is a device in which the incrementally adjustable mechanism is embedded in the maxillary incisal, canine or premolar region of the device so the maxilla can be retracted when the knobs and holes for any of the other described adjustability forms) are detached from its original position and reattached in a more tightened position. In this way the circumference of the dental arch of the device will decrease. As the maxilla is not able to move, the result of this maneuver will be the forward displacement of the mandible from its original position.

A particularly preferred way of shipping the device according to the invention to the end consumer is as a kit comprising the device and a temperature indicator adapted to indicate a temperature change to an elevated temperature at which the material of the device can be shaped. This makes it simple and safe for the end user to mold the device to conform to his or hers specific dentition simply by heating the relevant domain of the device in water at the temperature of which is kept in the correct temperature range for the material in question by using the indication of the temperature indicator.

It should be understood that the use of the anti-snore device according to the invention is not limited to prevention or reduction of snoring or OSAS but the device is applicable in any situation where it is desirable to secure free airway passage in human beings, such as during recovery from anesthesia, during unconsciousness, etc.

The unique combination of posterior resilient/mechanic hinging, dentition engagement and adjustability discussed above can also, according to another aspect of the invention, be utilized in a device for relieving guided transpositions of the jaws.

In this latter aspect, the invention relates to an orthognatic function device comprising an upper member adapted to engage with the maxillary dentition of a human and a lower member adapted to engage with the mandibulary dentition of the human, the upper and lower members having bases which prevent direct contact between opposing teeth, thereby eliminating guided transposition of the jaw relation and the upper and lower members being resiliently hinged together in such a manner together with the adjustability that the lower jaw of the human is kept positioned in a normal position relative to the upper jaw, allowing vertical movement and in the occluded intercuspidal position, allowing horizontal movement so that the temporo mandibular joint is kept substantially in its resting position, both when the lower jaw is at rest and when it is working.

It will be understood that also in this aspect, the resiliency of the hinging should be adapted to allow the physiological movement of the lower jaw in the sagittal plane, and that the above comments concerning selection of suitable materials, manufacturing method, and adaptation to the individual dentition by shaping the material in a softened, e.g. heat-softened, condition apply also to this aspect of the invention.

Thus, the orthognatic aspect of the invention provides a completely new philosophy in relieving temporo mandibular joint disorders caused by irregular dentition: In contrast to known orthognatic devices, the orthognatic device according to the invention is hinged in such a way that no interference between the upper and lower members can occur, thereby alleviating symptoms caused by abnormal interference from irregular dentition. Furthermore, tensions caused by tooth grinding and clenching are alleviated. At the same time, this orthognatic device is much simpler to adapt to the individual needs of the person in question than conventional orthognatic devices, and it can even be used by the individual consumer without assistance by any professional.

In the following, the incremental mandibular advancement anti-snoring device aspect of the invention will be explained in further detail with reference to the accompanying drawings.

Figure 52:
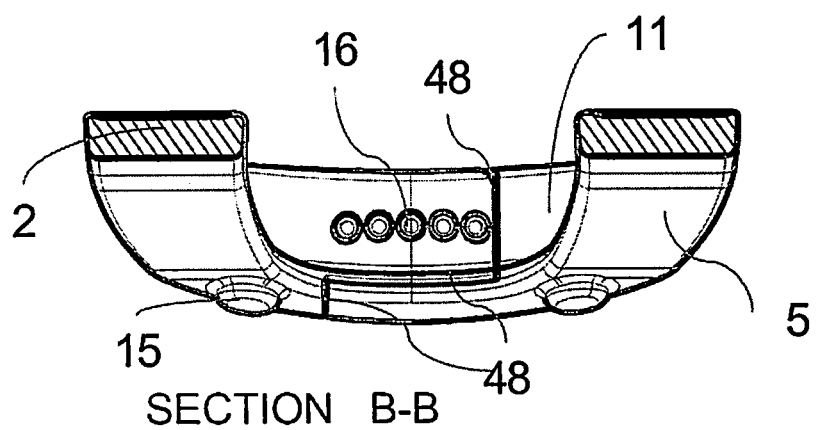
FIG. 52 shows the Midline Maxillary Incremental version of the Adjustable Mandibular Advancement Device in a dorsal view in its Neutral position wherein the incremental mechanism is shown in its natural non-elongated position.
Figure 53:
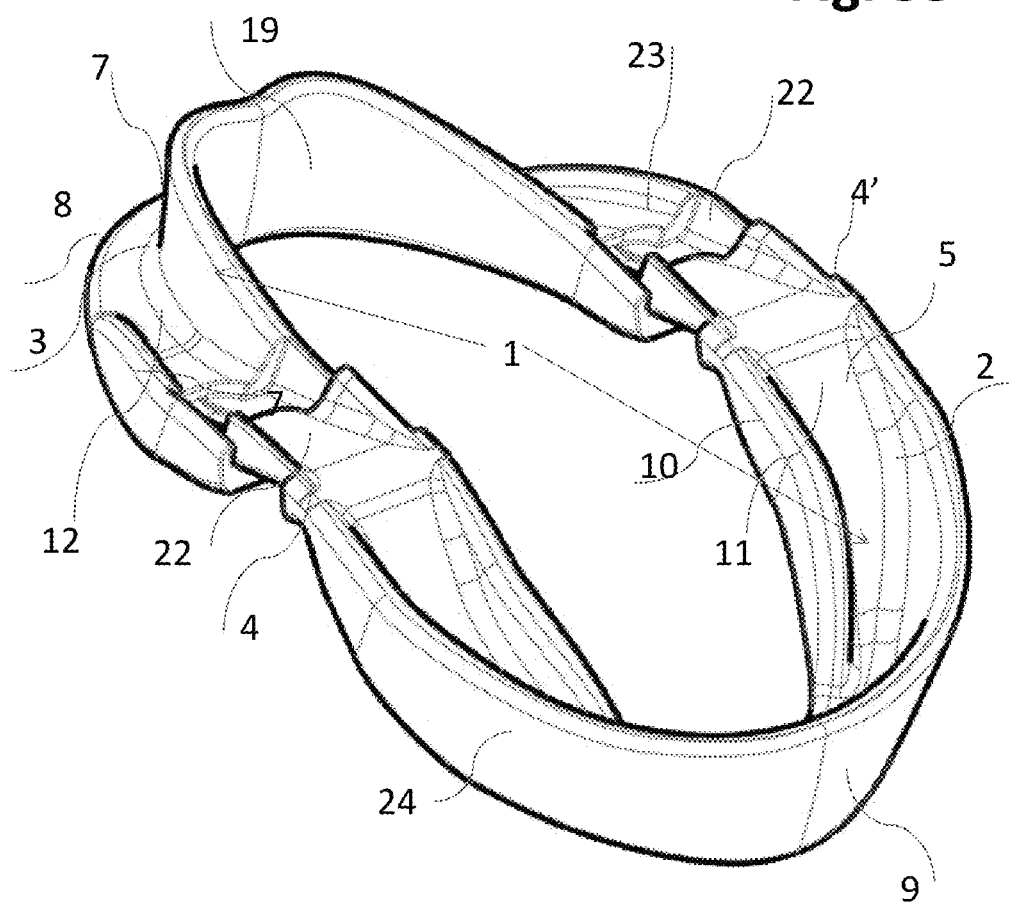
FIG. 53 shows the Successive version of the mandibular advancement device in which a sliding system is indicated (the sliding system here is in the form of a "dovetail guide structure"); the device is seen from an oblique perspective from the bottom part.
Figure 54:
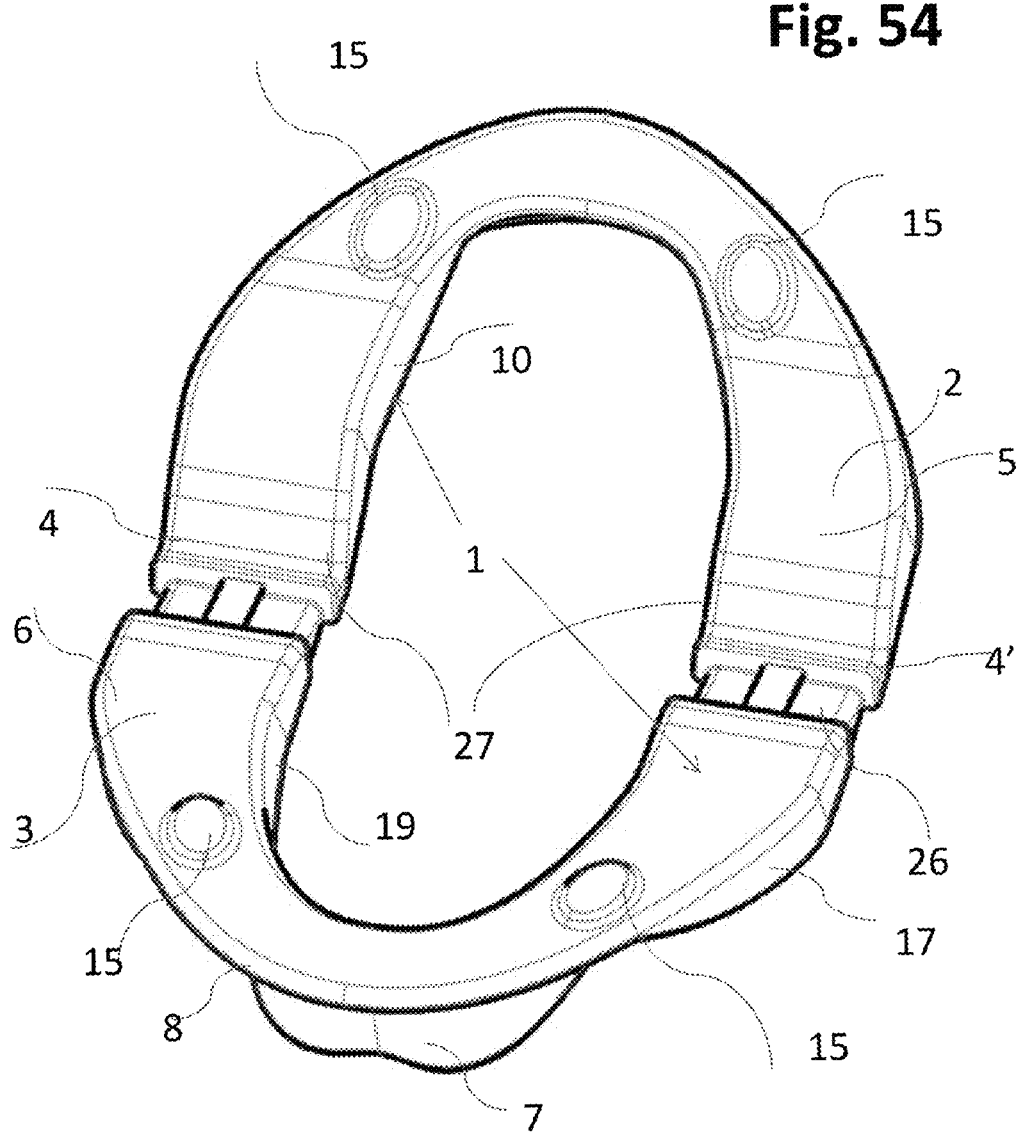
FIG. 54 shows the Successive version of the mandibular advancement device in an oblique perspective from the top part, in which a sliding system is indicated.
Figure 55:
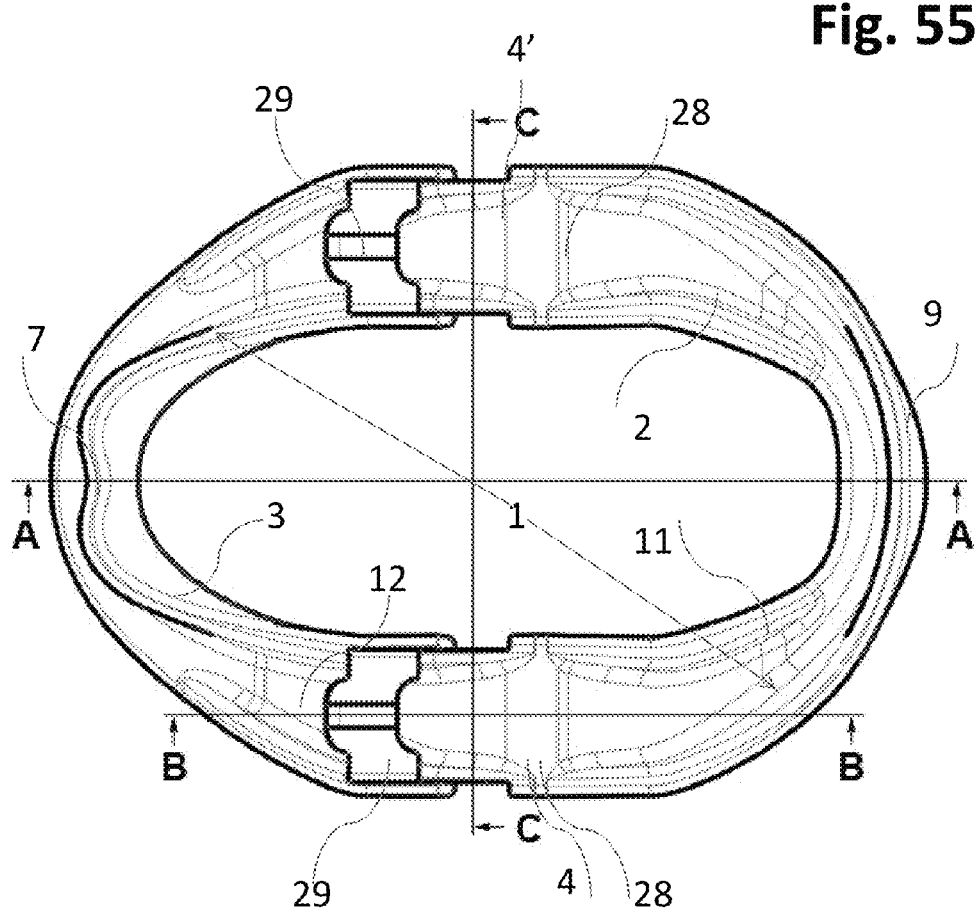
FIG. 55 shows the Successive version of the mandibular advancement device in a perpendicular perspective, in which a sliding system is indicated with its maximum elongation.
Figure 56:
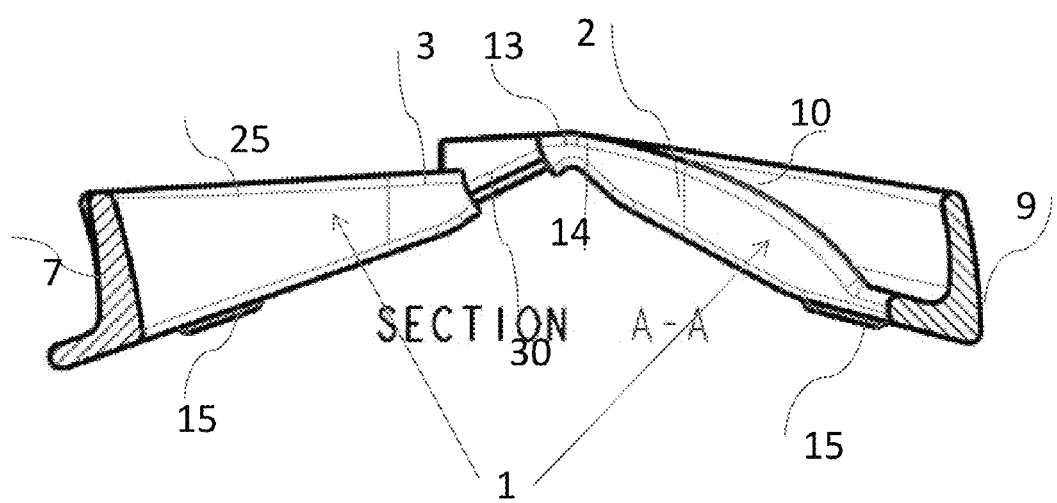
FIG. 56 shows the sectional drawing of the device at line A in FIG. 55 at its maximum elongation at the midline of the device.
Figure 57:
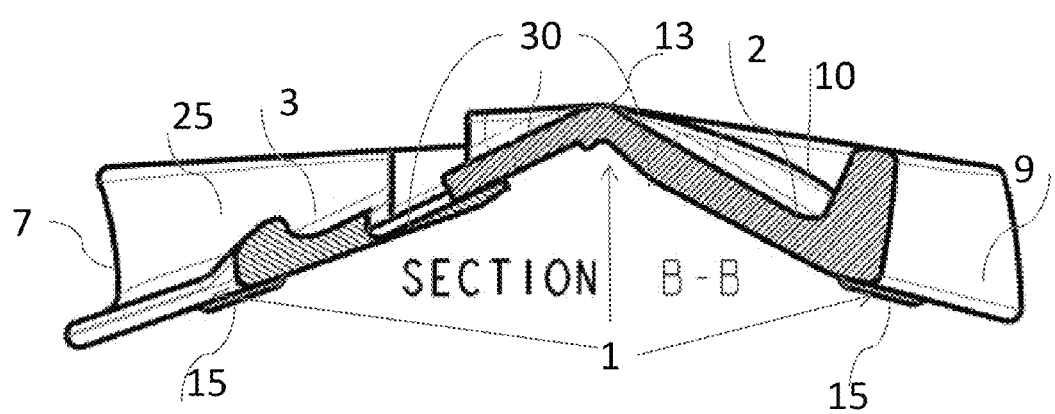
FIG. 57 shows the sectional drawing of the device at line B in FIG. 55 at its maximum elongation at the junction of the device members.
Figure 58:
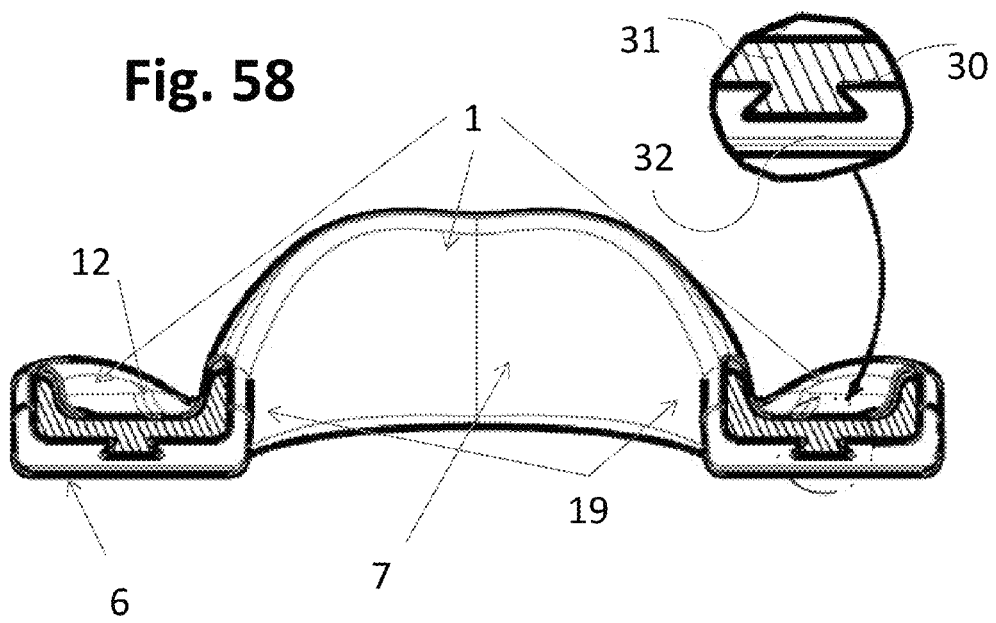
FIG. 58 shows the sectional drawing at line C in FIG. 55 in which the engaging mechanism can be seen, further in detailed insert.
Figure 59:
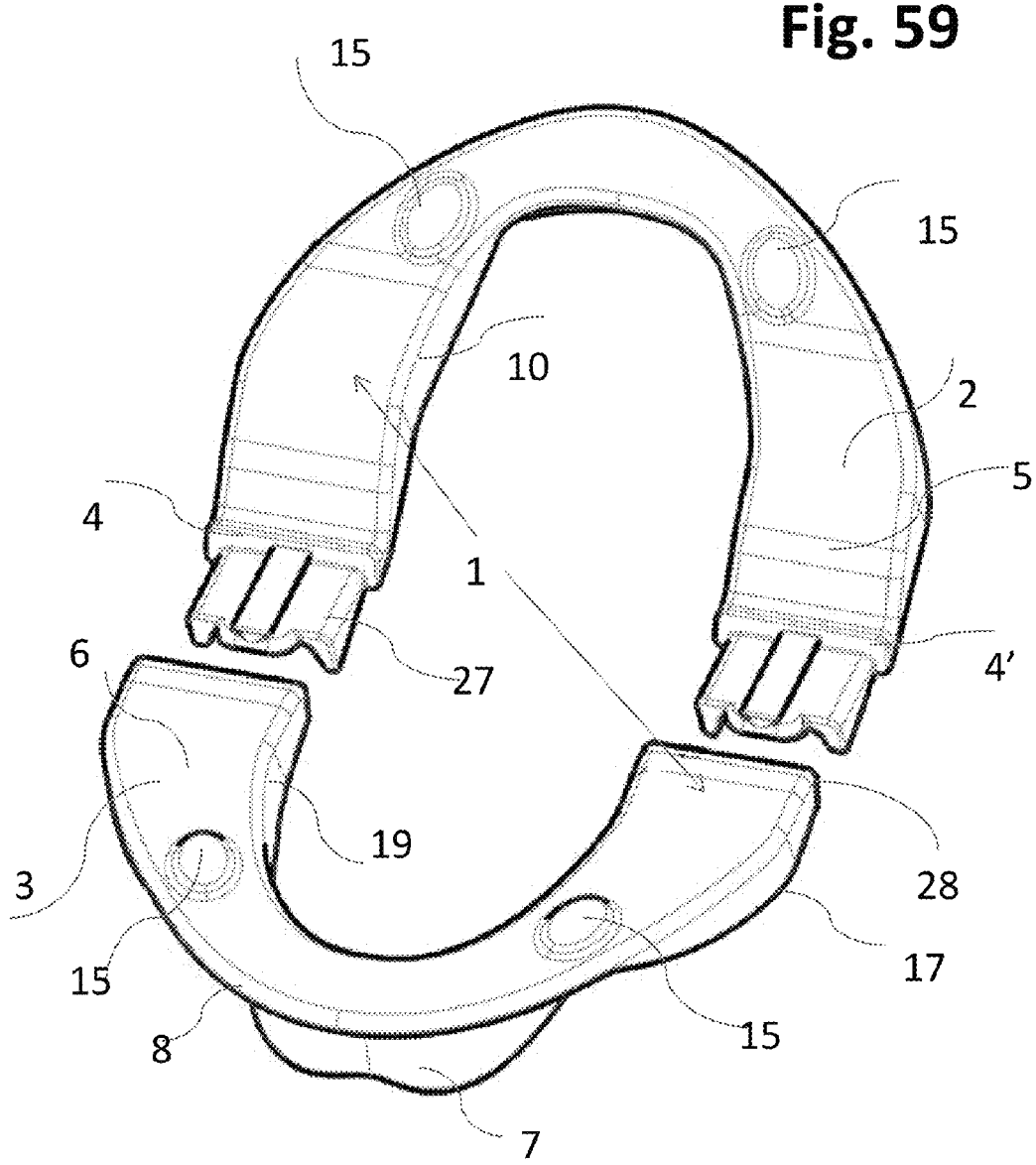
FIG. 59 shows the Successive version of the mandibular advancement device in which a sliding system is indicated (the sliding system here is in the form of a "dovetail guide structure"), the device is seen from an oblique perspective from the top in its detached situation.
Figure 60:
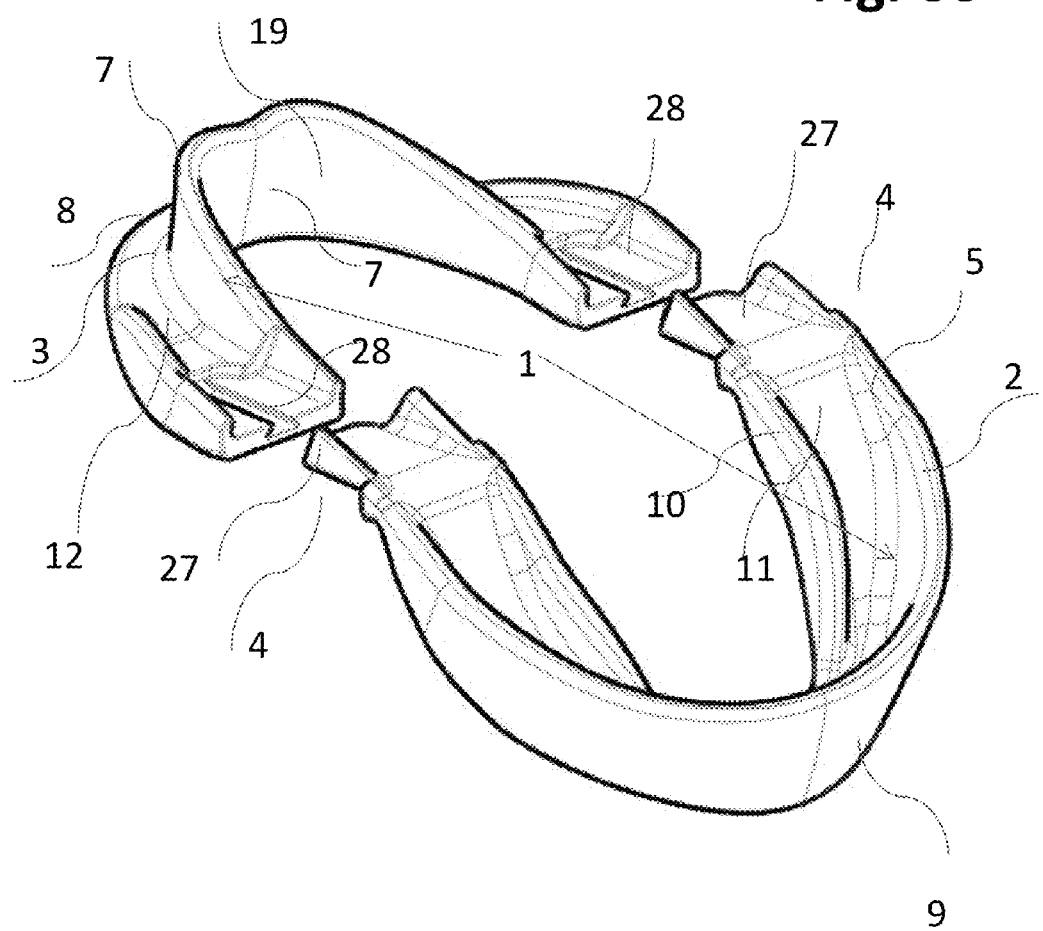
FIG. 60 shows the Successive version of the mandibular advancement device in which a sliding system is indicated (the sliding system here is in the form of a "dovetail guide structure"), the device is seen from an oblique perspective from the top in its detached situation.
Figure 61:
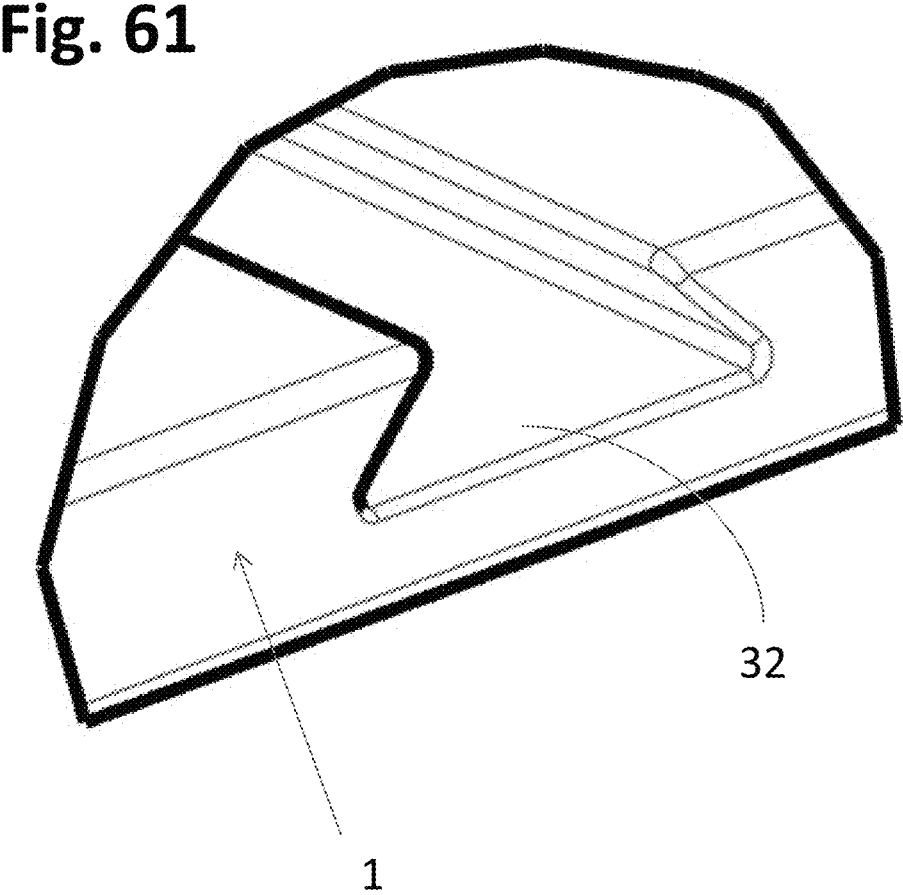
FIG. 61 shows a detailed enlargement of the negative structure of the Successive adjustable sliding mechanism depicted as a "dovetail guide"
Figure 62:
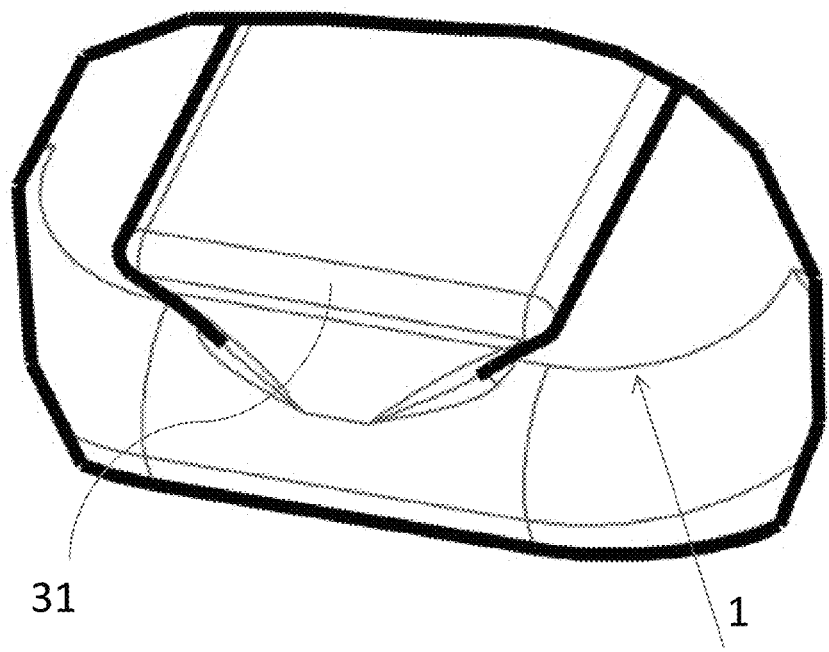
FIG. 62 shows a detailed enlargement of the positive structure of the Successive adjustable sliding mechanism depicted as a positive structure.
Figure 63:
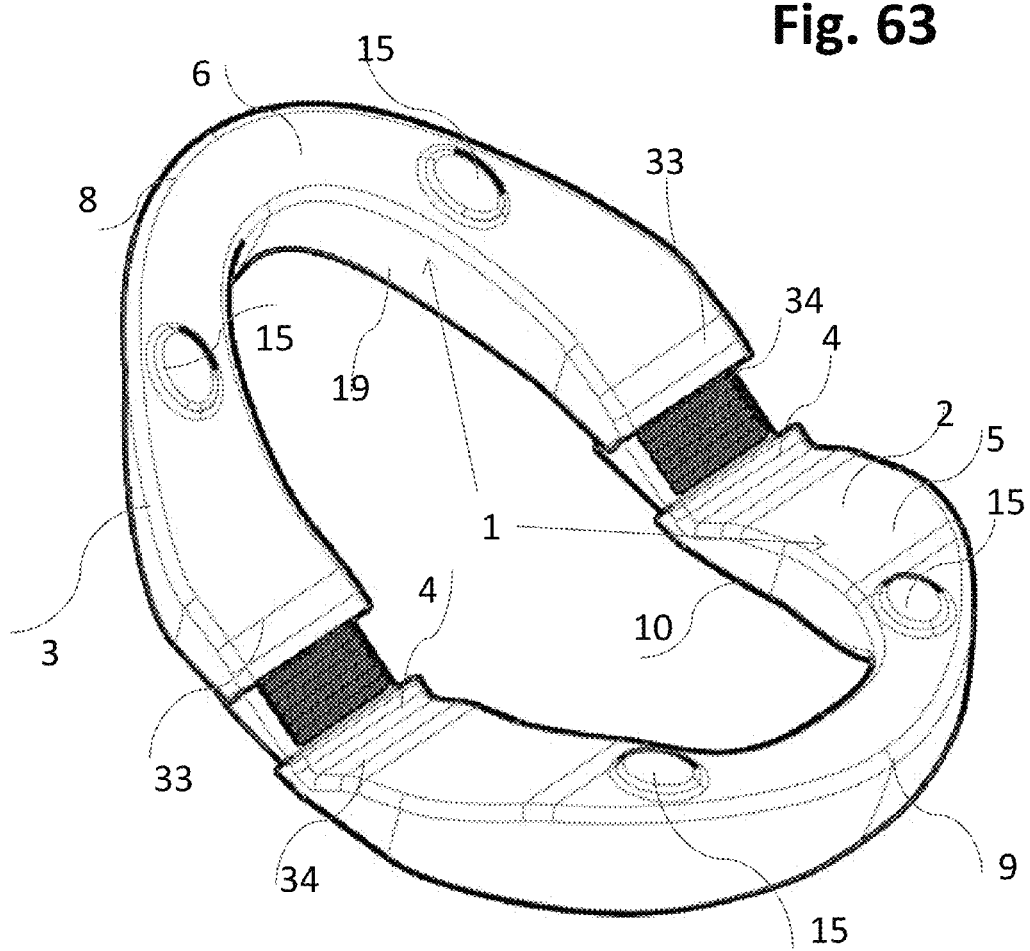
FIG. 63 shows the Successive version of the Adjustable Mandibular Advancement Device top view in a oblique perspective in its Maximum elongated position with visible platforms for the engagement of one part of the Velcro system. Note that the platform can also be used as one part of a gluing surface.
Figure 64:
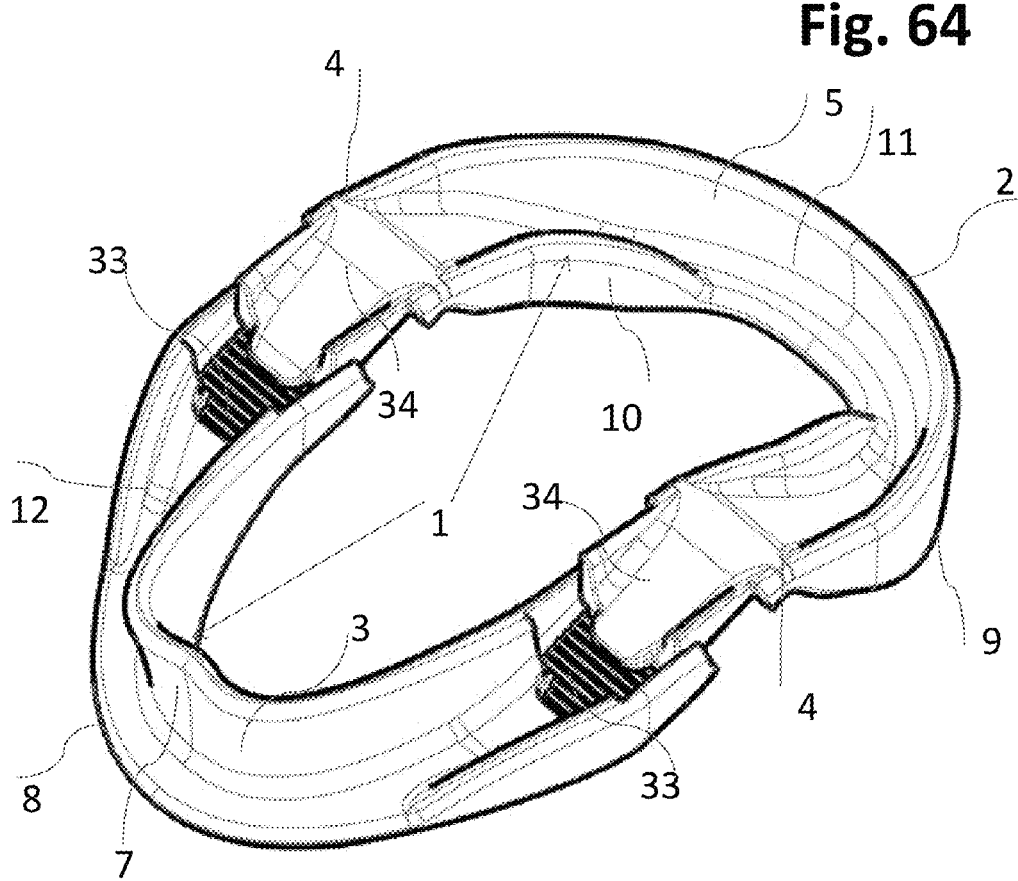
FIG. 64 shows the Successive version of the Adjustable Mandibular Advancement Device bottom view in its Maximum elongated position. Note that the platform connecting the two members can also be one part of a gluing surface.
Figure 65:
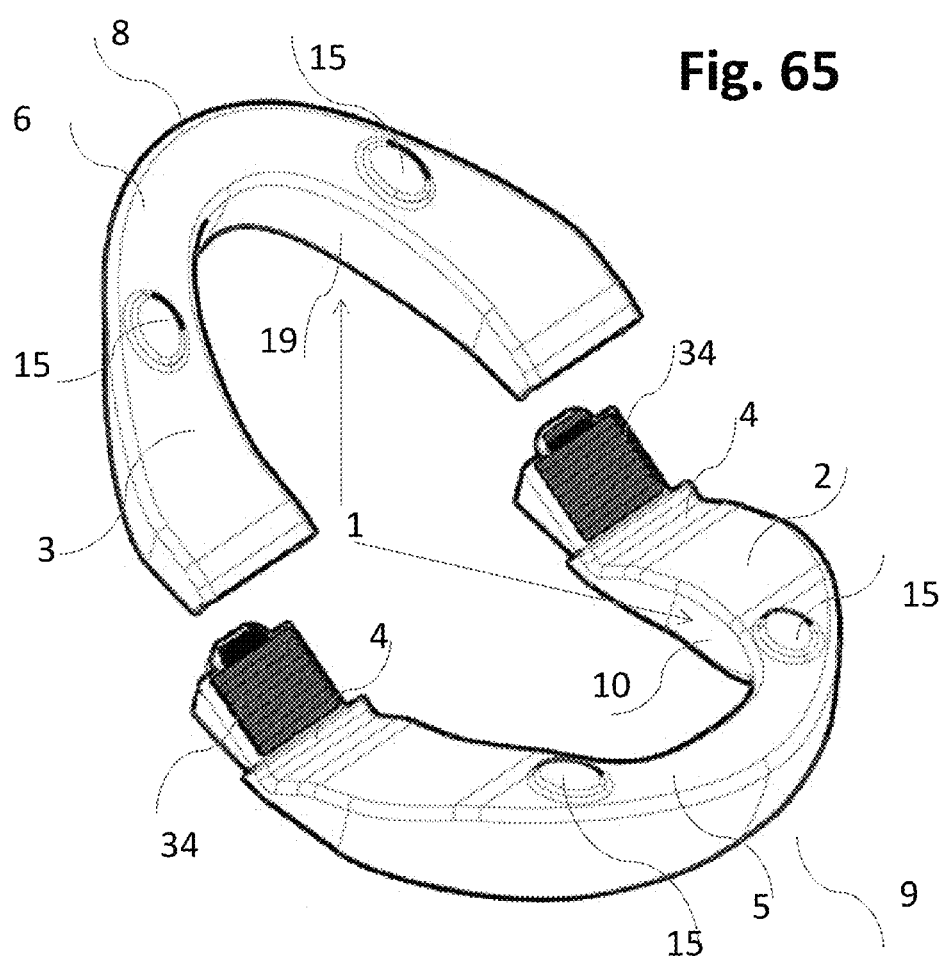
FIG. 65 shows the Successive version of the Adjustable Mandibular Advancement Device top view in a oblique perspective in its detached position with visible platforms for the engagement of one part of the Velcro system or a glue.
Figure 66:
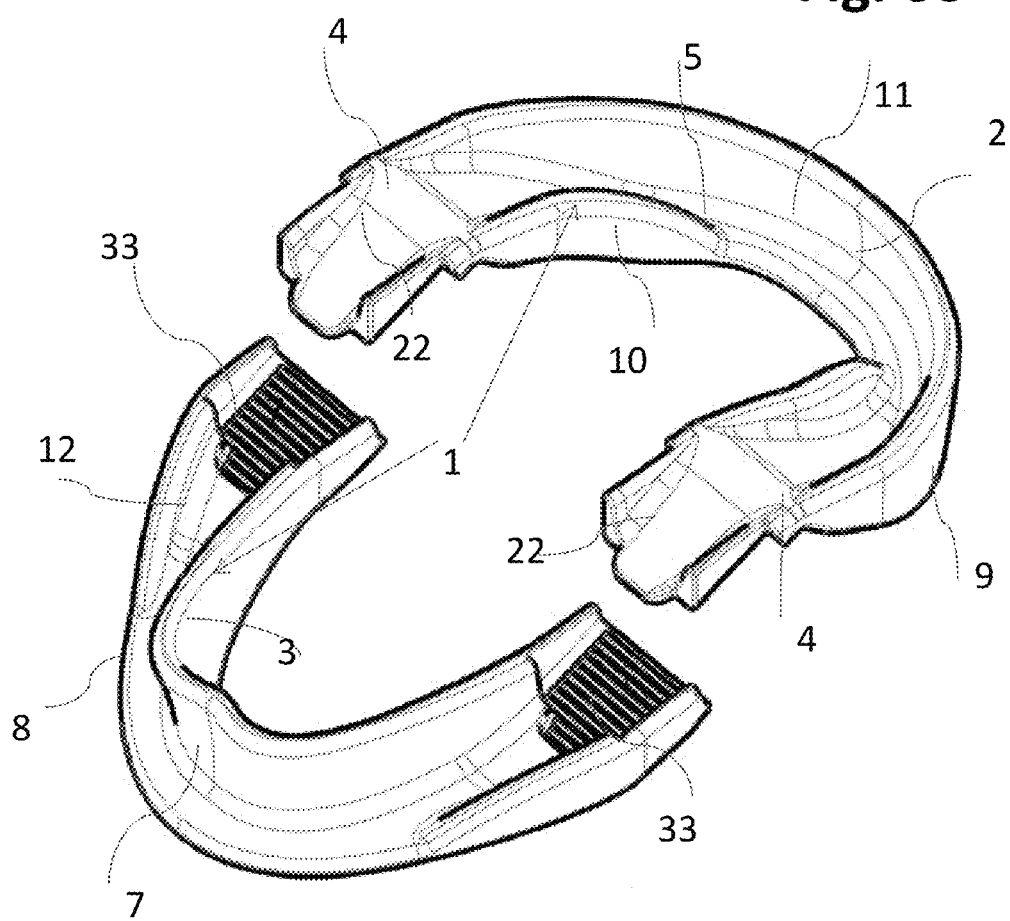
FIG. 66 shows the Successive version of the Adjustable Mandibular Advancement Device bottom view in a oblique perspective in its detached position with visible platforms for the engagement of one part of the Velcro system or a glue.
Figure 67:
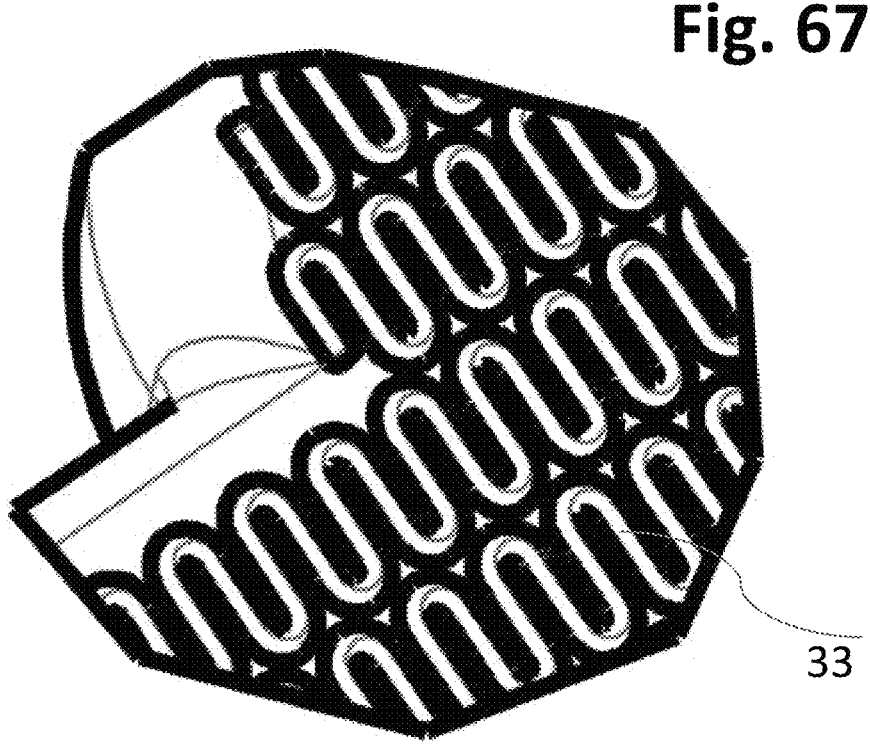
FIG. 67 shows enlarged detail of one part of the connecting platforms on either upper mandibular or lower mandibular to engage with its corresponding counterpart by Velcro system or a glue.
Figure 68:
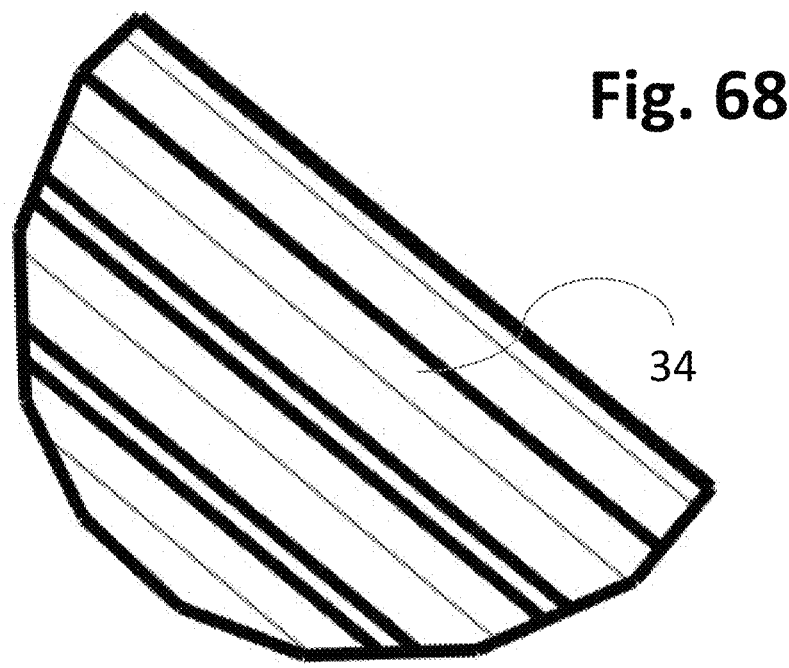
FIG. 68 Shows enlarged illustration of the other part of the connecting platforms on either upper mandibular or lower mandibular to engage with its corresponding counterpart by Velcro system or a glue
Figure 69A:
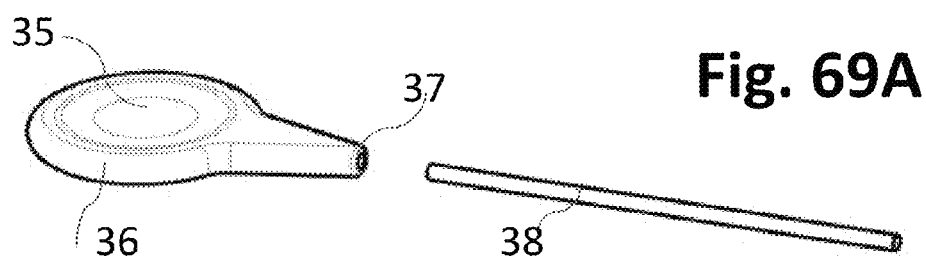
FIG. 69a shows the heat applicable rod tool with its discoid handle and its pin in an oblique projection from above.
Figure 69B:
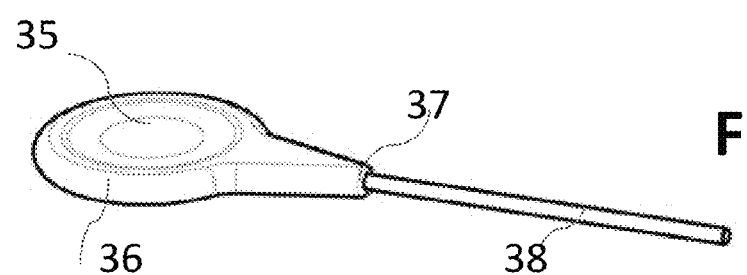
FIG. 69b shows the two parts of the heat applicable rod tool separated.
Figure 69C:
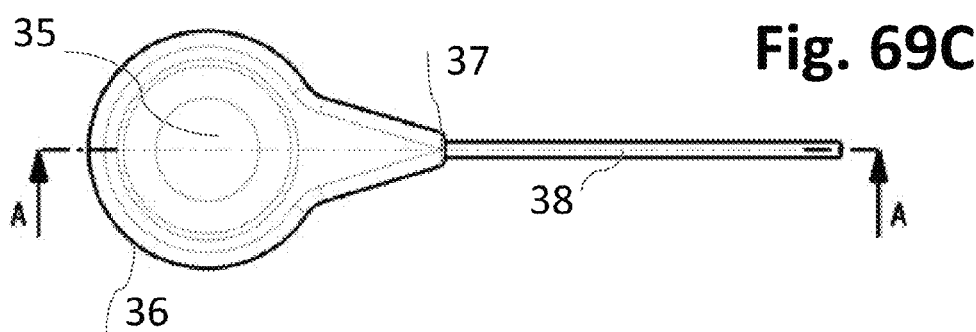
FIG. 69c shows the heat applicable rod tool with its handle and its pin from above, the A-A section describes in FIG. 69d.
Figure 69D:
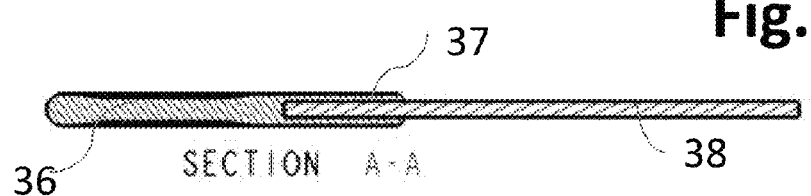
FIG. 69d shows the heat applicable in cross section from FIG. 69c in which the embedded rod is enclosed by the handle material.
Figure 70:
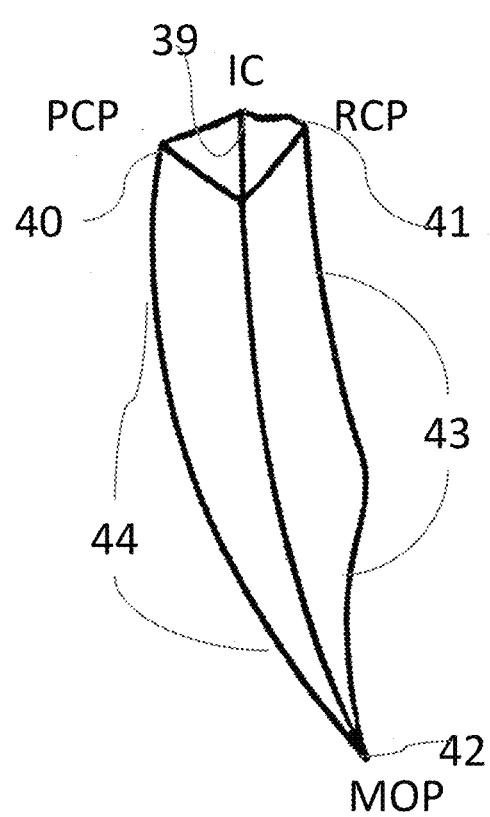
FIG. 70 shows a diagrammatic representation of the limitations of the movements of the lower jaw in any direction in the sagittal plane where PCP stands for the most protruded contact point of the teeth, IC stands for intercuspidal position (the maximal closing point), RCP stands for the most retracted contact position for the teeth, and MOP stands for the maximal opening point.
Figure 71:
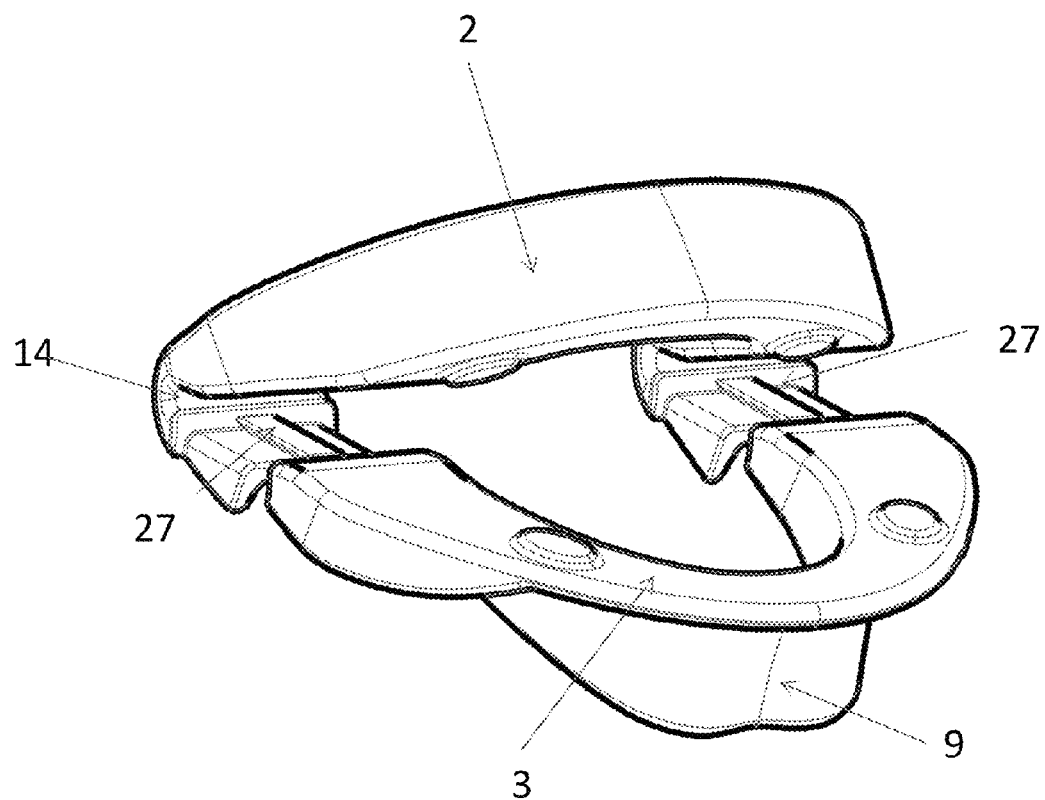
FIG. 71 shows the Tubular Successive version of the adjustable Mandibular Advancement Device shown in an activated and elongated detached view seen from a frontal oblique perspective shown in FIGS. 53 through 60.
Figure 72:
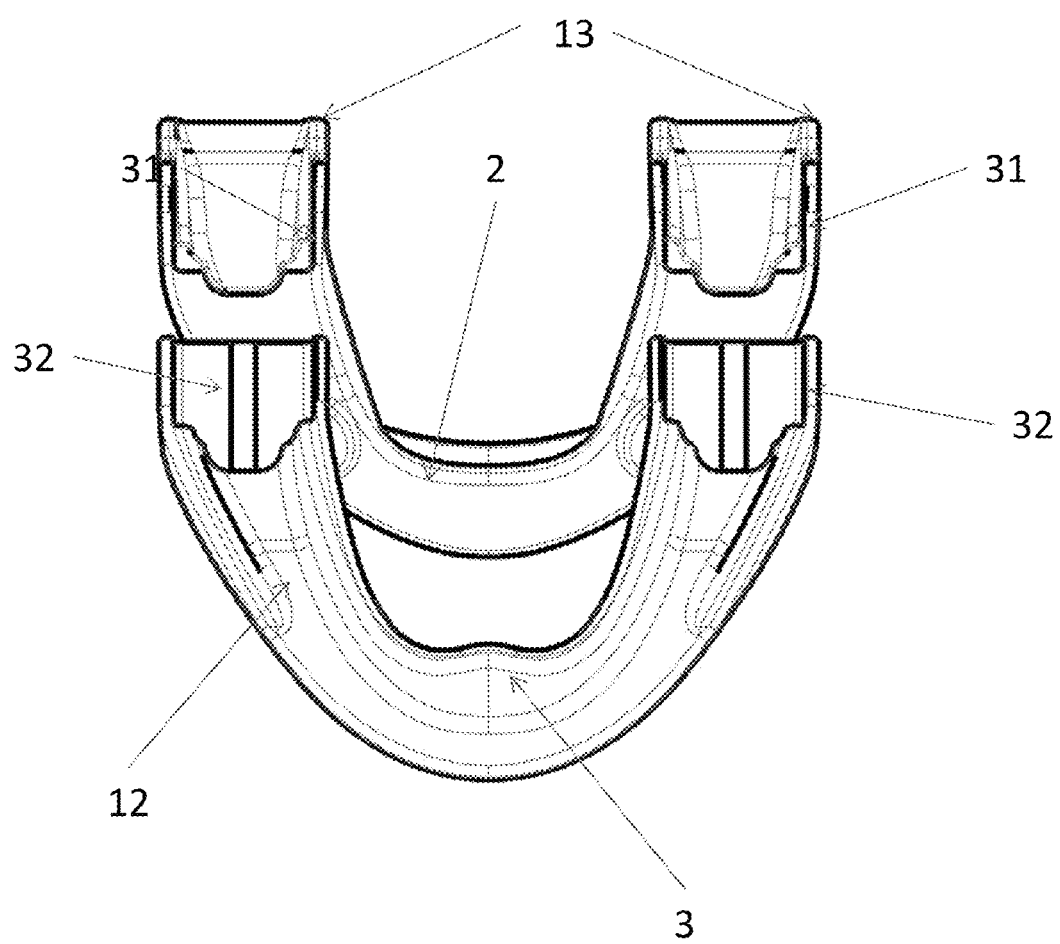
FIG. 72 shows the Tubular Successive version of the Adjustable Mandibular Advancement Device shown in an activated and elongated detached view seen from a bottom dorsal oblique perspective shown in FIGS. 53 through 60.
Figure 73:
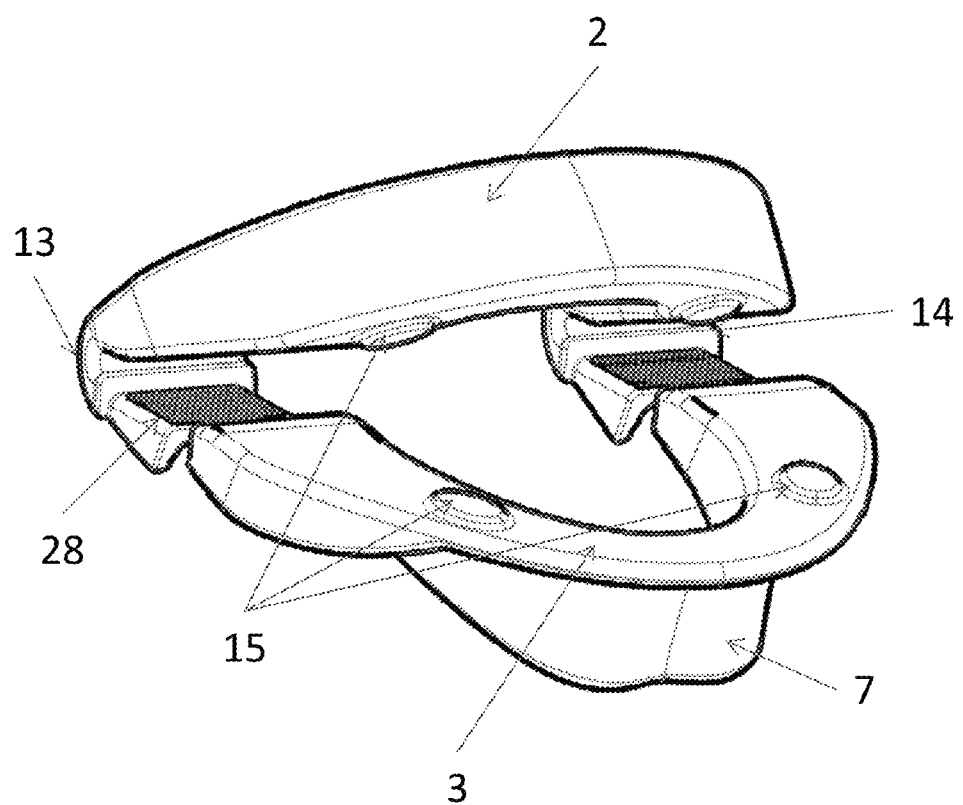
FIG. 73 shows the Successive version of the Adjustable Mandibular Advancement Device shown in an activated and elongated detached view seen from a frontal oblique perspective shown in FIGS. 53 through 63.
Figure 74:
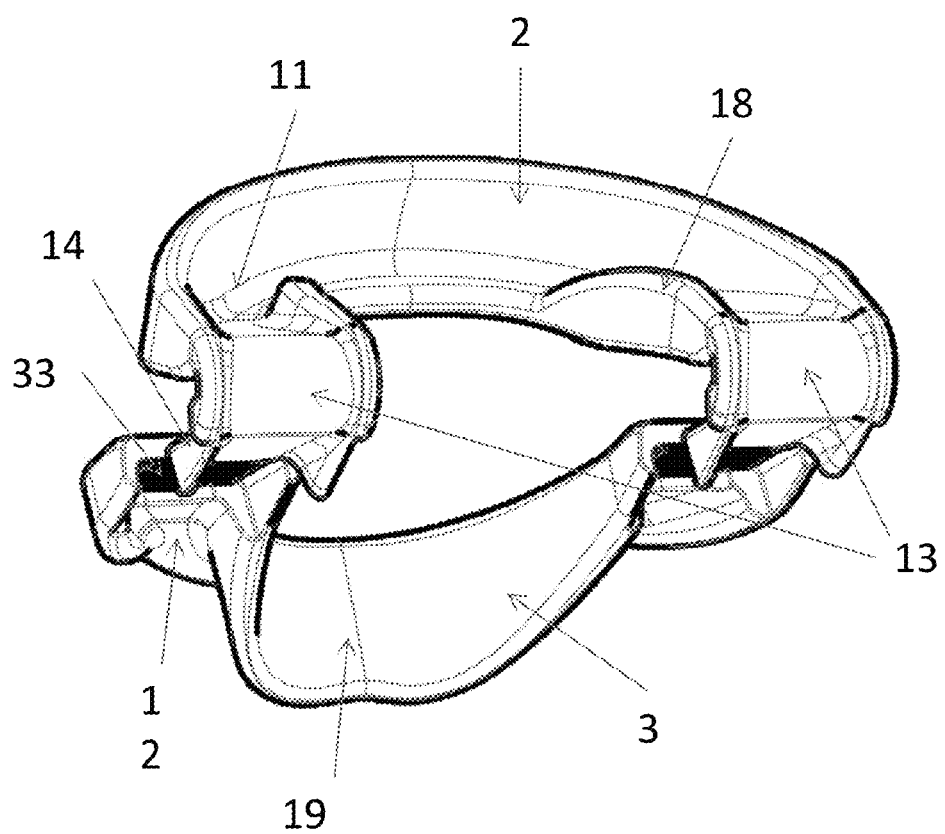
FIG. 74 shows the Successive version of the Adjustable Mandibular Advancement Device shown in an activated and elongated detached view seen from a bottom dorsal oblique perspective shown in FIGS. 53 through 63.

In FIGS. 1 through 52, in which like numerals indicate like parts, the device 1 according to the invention consists of two horseshoe-like members 2 and 3 of a soft, resilient plastics material, preferably a thermoplastic material, such as an ethylene vinyl acetate copolymer, or any suitable material, hinged together by means of integrated resilient or mechanical hinges 4 and 4'. Surfaces 5 and 6 represent the lower surface of the upper member and the upper surface of the lower member, respectively. 7 indicates the lingual flange of the lower member adapted to the lingual surfaces of the lower incisors, canines and premolars, this flange 7 being the part of the device which actually forces the lower jaw forward. 8 is the facial surface of the lower member, 9 is the facial surface of the upper member, and 10 is the lingual surface of the upper member. The conjoining effect of forces exerted by the facial surface 9 of the upper member and the lingual surface 7 of the lower member keep the lower jaw in a forward position relative to the upper jaw. As the facial surface 8 and the lingual surface 10 do not exert any forces, their dimensions are rather unethical and some embodiments of the invention may even be provided without these surfaces. No. 11 indicates the tunnel shaped space of the upper member 2 to engage with the upper dentition and 12 indicates the tunnel-shaped space of the lower member 3 adapted to engage the lower dentition. When the device is compressed to an active position convexity 13 appears at the posterior end part of the device and a concavity 14 at the anterior part of the hinging. The occusal knots, 15 are designed to prevent complete occlusion and lack of airspace between the members 1 and 2. No. 16 indicates the incremental mechanism, 17 is the Lateral facial portion of the mandibular member at the molar and premolar area, 18 is the Medial palatine portion of the maxillary member at the molar and premolar area, 19 shows the Lingual wall of mandibular member closest to the tongue. 20 is the Positive structure or male parts of the incremental mechanism, 21 the Negative structure of the incremental mechanism, 22 the Hinge member part of the invention with its negative structures of the incremental mechanism. 24 is the Lateral facial portion of the maxillary member at the molar and premolar area, 25 the Lingual wall of mandibular member closest to the teeth. No. 39 is the intercupidal position (IP) in which the dentition of the mandible makes the maximal interference with the dentition of the maxila; 40 is the protruded contact position (PCP) in which the mandible has made the maximal protruded movement from the IP position, still keeping some contact with the dentition of the maxila; 41 is the retracted contact position (RCP) in which the mandible have made the maximal retraction from the IP position, still keeping some contact with the dentition of the maxila, and 42 is the maximal opening point (MOP) in which the mandible has made the maximal opening movement from the IP position, all of which only being restricted by the muscles, the teeth, the ligaments and the discus involved in the temporoman-dibular joint system. 42 indicates the border describing the curve in which the mandible can slide open from the RCP, 43 is the border describing the curve in which the mandible can slide open from the PCP. No. 44 shows the Bottom view of the mandibular part of the saw-tag attachment structure and 45 is the Top view of the mandibular part of the saw-tag incremental mechanism, 46 is the Mandibular member part of the invention with its negative structure for engaging with the positive maxillary part structures of the saw-tag incremental mechanism and 47 is the Maxillary member part of the invention with its positive structure for engaging with the negative mandibulary parts structures of the saw-tag incremental mechanism.

48 is indicating the section line between the sliced part of the maxillary facial band in the closest proximity to the maxillary dentition especially in the region from the premolars in the right side to the premolars in the left side.

The preferred method of using the device described above and in the figures is to insert the device in the mouth of the affected individual, at nighttime before sleep.

By inserting the device in the mouth in the way that the mandible is forced a bit forward relative to the maxilla, increased airway space will appear in the back of throat, the pharynx, and thereby facilitate the free flow of air with its oxygen for the bodily metabolism at large.

Sometimes the alignment, of the teeth is not congruent with the ideal shape of a perfect dentition, and therefore the need for special modifications can prevail. To accomplish this task, the preferred material used for the device according to this invention, is made of a thermoplastic material, which can be subjectively moulded to adapt more perfect to the users non-perfect alignment of the teeth. Simply by immersing that actual part of the device, that needs modulation, into water at a prefixed temperature according to the material specification, the material can be moulded and hence get in closer contact with alignment of the wearers dentition. When it returns to the temperature of the room, or inside the mouth, the device will keep its new dimension, and thereby alleviate any hard or any loose contact with the teeth, thereby making it much more comfortable to wear during the sleep.

This procedure can be done by almost everybody with a little exercise, and does not need to acquire the competence and time from a professional dentist, doctor or technician at all.

One aspect of the incremental mechanism of the device according to the invention is that the wearer of the device can be given numerous possibility to calibrate his own degree of forwarding the mandible relative to the maxilla, by the use of any or all of the incrementally mechanisms described above.

For instance if the wearer of the device wants to elongate the mandible, simply detach the device parts, find a new location for the parts relative to each other and then attach again. In one particular case the mandible part can be detached from the maxillary part integrated with the hinge, forwarded or retracted from the previous position, then reattach the snap-on mechanism, and the effect of the device will change, with the result of more or less free airway space in the pharynx (depending on weather the user elongated or diminished the relative length).

In another particular case the maxillary part can be detached from the mandibulary part integrated with the hinge, forwarded or retracted from the previous position, then reattach the snap-on mechanism, and then again the effect of the device will change.

Yet in another particular case the maxillary part can be adjusted one or more steps in one side of the device (right or left), and the mandibular part of the opposing side (left or right) can be adjusted one or more steps individually from the other side. This part of the device modification can give the benefit of alignment to dentitions that are asymmetric or any other kind of special needs.

In some cases the user of the invention would prefer the incremental mechanism just to be situated in the front midline of the maxillary part of the device, and then for this is expressed through the description and the drawings. If the midline incremental mechanism is opened (detached snap-off) the circumference of the maxilla can be enlarged or diminished. If the arch circumference is enlarged relative to the mandible, the mandible is failing back towards its normal (airway occluding) position, whereas if the arch circumference is diminished the mandible is being forced further forward and thereby reliefs the occluded airway passage.

Any of the above alterations of the position between the two jaws, can be made with or without the use of the temperature sensitive alteration of the thermoplastic materials.

Another aspect of the device according to the invention is that the wearer of the device can fix the relative position of the maxillary part relative to the mandibulary part by the use of heating, either from the warmed water or from the metal rod that can be provided in one way of delivering the device package. When the wearer have accomplished the desired position be can immerse the device into the heated water and fix the position there by locking the negative and positive structures to each other, or be can use the metal rod to melt a part of the connected devise to prevent it from leaving the accomplished and desired position.

FIGS. 53-73, in which like numerals indicate like parts, the device 1 according to the invention consists of two horseshoe-like members 2 and 3 of a soft resilient plastics material, preferably a thermoplastic material, such as an ethylene vinyl acetate copolymer, or any suitable material, hinged together by means of integrated resilient or mechanical hinges 4 and 4'. Surfaces 5 and 6 represent the lower surface of the upper member and the upper surface of the lower member, respectively 7 indicates the lingual flange of the lower member adapted to the lingual surfaces of the lower incisors, canines and premolars, this flange 7 being the part of the device which actually forces the lower jaw forward. 8 is the facial surface of the lower member, 9 is the facial surface of the upper member, and 10 is the lingual surface of the upper member. The conjoining effect of forces exerted by the facial surface 9 of the upper member and the lingual surface 7 of the lower member keep the lower jaw in a forward position relative to the upper jaw. As the facial surface 8 and the lingual surface 10 do not exert any forces, their dimensions are rather uncritical and some embodiments of the invention may even be provided without these surfaces. No. 11 indicates the tunnel shaped space of the upper member 2 to engage with the upper dentition and 12 indicates the tunnel-shaped space of the lower member 3 adapted to engage the lower dentition. When the device is compressed to an active position, convexity 13 appears at the posterior end part of the device and a concavity 14 at the anterior part of the hinging. The occual knots 15 are designed to prevent complete occlusion and lack of airspace between the members 1 and 2. No. 17 is the Lateral facial portion of the mandibular member at the molar and premolar area, 18 is the medial palatine portion of the maxillary member at the molar and premolar area, 19 shows the Lingual wall of mandibular member closest to the tongue, 24 is the lateral facial portion of the maxillary member at the molar and premolar area, 25 the Lingual wall of mandibular member closest to the teeth, 26 the Mandibular member part of the invention with its positive structures of the successive mechanism, 27 the Hinge member part of the invention with its positive structure of the successive mechanism, 28 is the Hinge member part of the invention with its negative structures of the successive mechanism. 29 Upper or lower member with their positive structure of the successive part. 30 shows the Successive mechanism, 31 is the Positive structure of the successive mechanism, 32 the Negative structure of the successive mechanism. No. 33 is the Successive non specified 1. member of successive mechanism, 34 is the Successive non specified 2nd member of successive mechanism. In the figs. no. 35 indicates the Platform of the fingertip handle for the heating device, and 36 is the Edge of the fingertip handle for the heating device, where 37 is the Invagination part of the handpiece for holding the metal rod, 38 is the actual Metal rod. No. 39 is the intercuspidal position (IP) in which the dentition of the mandible makes the maximal interference with the dentition of the maxilla; 40 is the protruded contact position (PCP) in which the mandible has made the maximal protruded movement from the IP position, still keeping some contact with the dentition of the maxilla; 41 is the retracted contact position (RCP) in which the mandible have made the maximal retraction from the IP position, still keeping some contact with the dentition of the maxilla, and 42 is the maximal opening point (MOP) in which the mandible has made the maximal opening movement from the IP position, all of which only being restricted by the muscles, the teeth, the ligaments and the discus involved in the temporomandibular joint system. 42 indicates the border describing the curve in which the mandible can slide open from the RCP, 43 is the border describing the curve in which the mandible can slide open from the PCP.

FIGS. 75-78 illustrate the upper maxillary jaw Number 49, 50 the lower mandibular jaw, 51 indicates the three upper most cervical vertebrae of the human, the frontal part of the calvaria of the human is 52, no. 53 denominates the upper first molar, and 54 denominates the lower first molar, the upper central incisor is indicated with 55, and lower central incisor is 56. The tongue is named 57, and 58 indicates the soft palate close to the anterior wall of the pharynx indicated by 59, and 60 is the pharynx.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An incremental mandibular advancement anti-snoring and obstructive sleep apnea preventing device for a human, the human having an upper jaw and a lower jaw, the upper jaw supporting a maxillary dentition, the lower jaw supporting a mandibulary dentition, the human having, a nasopharynx, a oropharynx and a hypopharynx defining a airway passage, the device comprising;

an upper member adapted to engage the maxillary dentition of the human;

a lower member adapted to engage the mandibulary dentition of the human;

a first resilient hinge and a second resilient hinge coupling said upper member and said lower member for allowing physiological movements of the lower jaw in the sagital plane;

said first resilient hinge having a first incrementally adjustment member;

said second resilient hinge having a second incrementally adjustment member;

said first incrementally adjustment member and said second incrementally adjustment member allowing incrementally adjustments of said upper member relative to said lower member; and said incrementally adjustments defining multiple retaining forward positions of the lower jaw relative to the upper jaw and thereby keeping the airway passage in the nasopharynx, the oropharynx and the hypopharynx substantially free of occlusion.

2. An incremental mandibular advancement anti-snoring and obstructive sleep apnea preventing device as set forth in claim 1, wherein said first incrementally adjustment member and said second incrementally adjustment member are embedded in said upper member and said lower member.

3. An incremental mandibular advancement anti-snoring and obstructive sleep apnea preventing device as set forth in claim 1, wherein said first incrementally adjustment member and said second incrementally adjustment member are embedded in said lower member.

4. An incremental mandibular advancement anti-snoring and obstructive sleep apnea preventing device as set forth in claim 1, Wherein said first incrementally adjustment member and said second incrementally adjustment member are embedded in said upper member.

5. An incremental mandibular advancement anti-snoring and obstructive sleep apnea preventing device as set forth in claim 1, wherein said first incrementally adjustment member and said second incrementally adjustment member include multiple stepwise snap-on snap-off members.

6. An incremental mandibular advancement anti-snoring and obstructive sleep apnea preventing device as set forth in claim 5, wherein said multiple stepwise snap-on snap-off members include a positive structure and a negative structure.

7. An incremental mandibular advancement anti-snoring and obstructive sleep apnea preventing device as set forth in claim 6, wherein said positive structure having a cross-section shape selected from the group consisting of a circle, square and a hexagon; and said negative structure having an aperture shape selected from the group consisting of a circle, square and a hexagon.

8. An incremental mandibular advancement anti-snoring and obstructive sleep apnea preventing device as set forth in claim wherein said first incrementally adjustment member and said second incrementally adjustment member include hook and loop members.

9. An incremental mandibular advancement anti-snoring and obstructive sleep apnea preventing device as set forth in claim 1, wherein said first incrementally adjustment member and said second incrementally adjustment member include a positive structure and a negative structure.

10. An incremental mandibular advancement anti-snoring and obstructive sleep apnea preventing device as set forth in claim 9, wherein said positive structure having a cross-section shape selected from the group consisting of a square, a rectangle and a dovetail; and said negative structure having a cross-section shape selected from the group consisting of a square, a rectangle and a dovetail.

11. An incremental mandibular advancement anti-snoring and obstructive sleep apnea preventing device as set forth in claim 1, wherein said upper member has an anterior wall adapted to be in contact with the facial surfaces of the incisors, canines and premolars of the upper jaw; and said lower member has a posterior wall adapted to be in contact with the lingual surfaces of the incisors, canines and premolars of the lower jaw.

12. An incremental mandibular advancement anti-snoring and obstructive sleep apnea preventing device as set forth in claim 1, wherein said upper member has a ellipsoid shape substantially in accordance with the normal dentition of a human; and said lower member has a parabola shape substantially in accordance with the human dentition.

13. An incremental mandibular advancement anti-snoring and obstructive sleep apnea preventing device as set forth in claim 1, wherein said upper member, said lower member, said first resilient hinge and said second resilient hinge are constructed of a resilient non-toxic plastics material selected from the group consisting of a polyvinyl material, a polyethylene material and a polypropylene material.

14. An incremental mandibular advancement anti-snoring and obstructive sleep apnea preventing device as set forth in claim 1, wherein said upper member, said lower member, said first resilient hinge and said second resilient hinge are constructed of a resilient non-toxic plastics material including a thermoplastic material which can be Shaped to adapt to an individual dentition by moderate heating.

15. An incremental mandibular advancement anti-snoring and obstructive sleep apnea preventing device as set forth in claim 1, further including a temperature indicator coupled to said upper member, said lower member, said first resilient hinge or said second resilient hinge for indicating the temperature change to an elevated temperature at which the material can be shaped.

16. An incremental mandibular advancement anti-snoring and obstructive sleep apnea preventing device for a human, the human having an upper jaw and a lower jaw, the upper jaw supporting a maxillary dentition, the lower jaw supporting a mandibulary dentition, the human having, a nasopharynx, a oropharynx and a hypopharynx defining a airway passage, the device comprising;
    an upper member adapted to engage the maxillary dentition of the human;
    a lower member adapted to engage the mandibulary dentition of the human;
    a first resilient hinge and a second resilient hinge coupling said upper member and said lower member for allowing physiological movements of the lower jaw in the sagittal plane;
    said first resilient hinge having a first incrementally adjustment member;
    said second resilient hinge having a second incrementally adjustment member;
    said first incrementally adjustment member and said second incrementally adjustment member allowing incrementally adjustments of said upper member relative to said lower member; and
    said incrementally adjustments defining multiple retaining forward positions of the lower jaw relative to the upper jaw and the lower jaw in the position corresponding to the area between an intercuspidal position, a protruded contact position, and a maximum opening point of the jaw and thereby keeping the airway passage in the nasopharynx, the oropharynx and the hypopharynx substantially free of occlusion.

17. An incremental mandibular advancement anti-snoring and obstructive sleep apnea preventing device as set forth in claim 16, wherein said upper member, said lower member, said first resilient hinge and said second resilient hinge are adapted to keep the lower jaw substantially in the position corresponding to the anterior border of the physiological space of movement of the lower jaw as limited by the anatomical structures in the temporo mandibular joint.

18. An incremental mandibular advancement anti-snoring and obstructive sleep apnea preventing device as set forth in claim 16, wherein said multiple retaining forward positions are in the range of 5 to 13 mm in the sagittal plane and 6 to 35 mm in the vertical plane along the border of the IP-MOP curve.

19. An incremental mandibular advancement anti-snoring and obstructive sleep apnea preventing device for a human, the human having an upper jaw and a lower jaw, the upper jaw supporting a maxillary dentition, the lower jaw supporting a mandibulary dentition, the human having a nasopharynx, a oropharynx and a hypopharynx defining a airway passage, the device comprising;
    an upper member adapted to engage the maxillary dentition of the human;
    a lower member adapted to engage the mandibulary dentition of the human;
    a first resilient binge and a second resilient hinge coupling said upper member and said lower member for allowing physiological movements of the lower jaw in the sagittal plane;
    said first resilient hinge having a first incrementally adjustment member;
    said second resilient hinge having a second incrementally adjustment member;
    said first incrementally adjustment member and said second incrementally adjustment member allowing incrementally adjustments of said upper member relative to said lower member;
    said incrementally adjustments defining multiple retaining forward positions of the lower jaw relative to the upper jaw and thereby keeping the airway passage in the nasopharynx, the oropharynx and the hypopharynx substantially free of occlusion;
    said first incrementally adjustment member and said second incrementally adjustment member include multiple stepwise snap-on snap-off members;
    said multiple stepwise snap-on snap-off members include a positive structure and a negative structure;
    said positive structure having a cross-section shape selected from the group consisting of a circle, square and a hexagon; and
    said negative structure having an aperture shape selected from the group consisting of a circle, square and a hexagon.

20. An successive mandibular advancement anti-snoring and obstructive sleep apnea preventing device for a human, the human having an upper jaw and a lower jaw, the upper jaw supporting a maxillary dentition, the lower jaw supporting a mandibulary dentition, the human having a nasopharynx, a oropharynx and a hypopharynx defining a airway passage, the device comprising;
    an upper member adapted to engage the maxillary dentition of the human;
    a lower member adapted to engage the mandibulary dentition of the human;
    a first resilient hinge and a second resilient hinge coupling said upper member and said lower member for allowing physiological movements of the lower jaw in the sagittal plane;
    said first resilient hinge having a first successive adjustment member;
    said second resilient hinge having a second successive adjustment member;
    said first successive adjustment member and said second successive adjustment member allowing successive adjustments of said upper member relative to said lower member;
    said successive adjustments defining multiple retaining forward positions of the lower jaw relative to the upper jaw and thereby keeping the airway passage in the nasopharynx, the oropharynx and the hypopharynx substantially free of occlusion; and said first successive adjustment member and said second successive adjustment member include telescopic system having a positive structure and a negative structure.

21. A successive mandibular advancement anti-snoring and obstructive sleep apnea preventing device for a human, the human having an upper jaw and a lower jaw, the upper jaw supporting a maxillary dentition, the lower jaw supporting a mandibulary dentition, the human having a nasopharynx, a oropharynx and a hypopharynx defining a airway passage, the device comprising;

an upper member adapted to engage the maxillary dentition of the human;

a lower member adapted to engage the mandibulary dentition of the human;

a first resilient hinge and a second resilient hinge coupling said upper member and said lower member for allowing physiological movements of the lower jaw in the sagittal plane;

said first resilient hinge having a first successive adjustment member;

said second resilient hinge having a second successive adjustment member;

said first successive adjustment member and said second successive adjustment member allowing successive adjustments of said upper member relative to said lower member; and said successive adjustments defining multiple retaining forward positions of the lower jaw relative to the upper jaw and thereby keeping the airway passage in the nasopharynx, the oropharynx and the hypopharynx substantially free of occlusion.

\* \* \* \* \*